US012033063B2

(12) United States Patent
Ben-Avi et al.

(10) Patent No.: US 12,033,063 B2
(45) Date of Patent: *Jul. 9, 2024

(54) SCHEDULING CONFIGURATION FOR DEEP LEARNING NETWORKS

(71) Applicant: Intel Corporation, Santa Clara, CA (US)

(72) Inventors: Eran Ben-Avi, Haifa (IL); Neta Zmora, Tzur Moshe (IL); Guy Jacob, Netanya (IL); Lev Faivishevsky, Kfar Saba (IL); Jeremie Dreyfuss, Tel-Aviv (IL); Tomer Bar-On, Petah Tikva (IL); Jacob Subag, Kiryat Haim (IL); Yaniv Fais, Tel-Aviv (IL); Shira Hirsch, Jerusalem (IL); Orly Weisel, Elazar (IL); Zigi Walter, Haifa (IL); Yarden Oren, Jerusalem (IL)

(73) Assignee: Intel Corporation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/174,275

(22) Filed: Feb. 24, 2023

(65) Prior Publication Data
US 2023/0281435 A1 Sep. 7, 2023

Related U.S. Application Data

(63) Continuation of application No. 15/499,900, filed on Apr. 28, 2017, now Pat. No. 11,599,777.

(51) Int. Cl.
*G06N 3/06* (2006.01)
*G06N 3/044* (2023.01)
(Continued)

(52) U.S. Cl.
CPC ............ *G06N 3/063* (2013.01); *G06N 3/044* (2023.01); *G06N 3/045* (2023.01); *G06N 3/084* (2013.01)

(58) Field of Classification Search
CPC .... G06N 3/063; G06N 3/0445; G06N 3/0454; G06N 3/084; G06N 3/08; G06N 3/04; G06N 3/044; G06N 3/045
(Continued)

(56) References Cited

U.S. PATENT DOCUMENTS 5,179,631 A * 1/1993 Guddanti .................. G06J 1/00
706/41
7,873,812 B1 1/2011 Mimar
(Continued)

OTHER PUBLICATIONS

Lindholm et al., "Nvidia Tesla: a Unified Graphics and Computing Architecture", IEEE Computer Society, 2008. (Previously supplied). (Year: 2008).*
(Continued)

*Primary Examiner* — Dave Misir
(74) *Attorney, Agent, or Firm* — Jaffery Watson Mendonsa & Hamilton LLP

(57) ABSTRACT

In an example, an apparatus comprises a plurality of execution units comprising and logic, at least partially including hardware logic, to traverse a solution space, score a plurality of solutions to a scheduling deep learning network execution, and select a preferred solution from the plurality of solutions to implement the deep learning network. Other embodiments are also disclosed and claimed.

20 Claims, 37 Drawing Sheets

(51) Int. Cl.
  *G06N 3/045* (2023.01)
  *G06N 3/063* (2023.01)
  *G06N 3/084* (2023.01)

(58) Field of Classification Search
  USPC .......................................................... 706/25
  See application file for complete search history.

(56) References Cited

U.S. PATENT DOCUMENTS

| | | | |
|---|---|---|---|
| 10,528,864 B2 | 1/2020 | Dally et al. | |
| 10,860,922 B2 | 12/2020 | Dally et al. | |
| 10,891,538 B2 | 1/2021 | Dally et al. | |
| 2014/0259016 A1* | 9/2014 | Lottes | G06F 9/4881 718/102 |
| 2016/0062947 A1* | 3/2016 | Chetlur | G06F 17/153 708/420 |
| 2016/0321776 A1* | 11/2016 | Zou | G06T 1/20 |
| 2017/0039396 A1* | 2/2017 | Sharp | G06F 21/74 |
| 2018/0046906 A1 | 2/2018 | Dally et al. | |
| 2018/0278588 A1* | 9/2018 | Cela | H04L 69/12 |

OTHER PUBLICATIONS

Hegde et al., "CaffePresso: An Optimized Library for Deep Learning on Embedded Accelerator-based platforms", CASES '16, Oct. 1-7, 2016, Pittsburgh, PA, USA. (Previously supplied). (Year: 2016).*

Yazdanbakhsh et al., "Neural Acceleration for GPU Throughput Processors", MICRO-48 , Dec. 5-9, 2015, Waikiki, HI, USA. (Previously supplied). (Year: 2015).*

Luo et al., "DaDianNao: A Neural Network Supercomputer", IEEE Transactions on Computers, vol. 66, No. 1, Jan. 2017. (Previously supplied). (Year: 2017).*

Li et al., "Large Scale Recurrent Neural Network on GPU", 2014 International Joint Conference on Neural Networks (IJCNN) Jul. 6-11, 2014, Beijing, China. (Previously supplied). (Year: 2014).*

Kim et al., "Neurocube: A Programmable Digital Neuromorphic Architecture with High-Density 3D Memory", 2016 ACM/IEEE 43rd Annual International Symposium on Computer Architecture. (Previously supplied). (Year: 2016).*

Ben-Nun et al., "Memory Access Patterns: The Missing Piece of the Multi-GPU Puzzle", SC '15, Nov. 15-20, 2015, Austin, TX, USA. (Previously supplied). (Year: 2015).*

Bakhoda et al., "Analyzing CUDA Workloads Using a Detailed GPU Simulator", IEEE, 2009. (Previously supplied). (Year: 2009).*

Goodfellow, et al. "Adaptive Computation and Machine Learning Series", Book, Nov. 18, 2016, pp. 98-165, Chapter 5, The MIT Press, Cambridge, MA.

Ross, et al. "Intel Processor Graphics: Architecture & Programming", Power Point Presentation, Aug. 2015, 78 pages, Intel Corporation, Santa Clara, CA.

Shane Cook, "CUDA Programming", Book, 2013, pp. 37-52, Chapter 3, Elsevier Inc., Amsterdam Netherlands.

Nicholas Wilt, "The CUDA Handbook; A Comprehensive Guide to GPU Programming", Book, Jun. 22, 2013, pp. 41-57, Addison-Wesley Professional, Boston, MA.

Stephen Junkins, "The Compute Architecture of Intel Processor Graphics Gen9", paper, Aug. 14, 2015, 22 pages, Version 1.0, Intel Corporation, Santa Clara, CA.

* cited by examiner

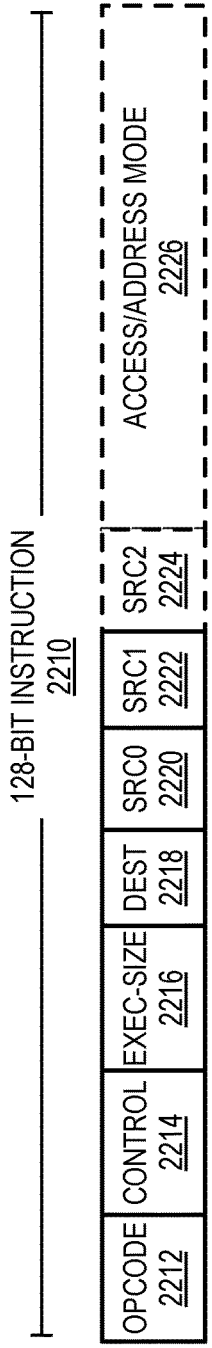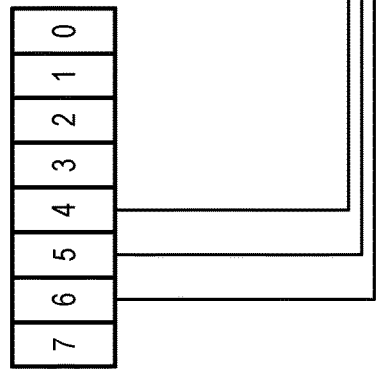
FIG. 22

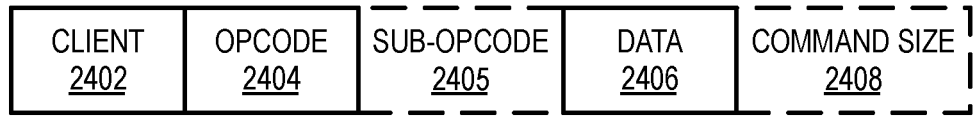
FIG. 24A  GRAPHICS PROCESSOR COMMAND FORMAT
2400
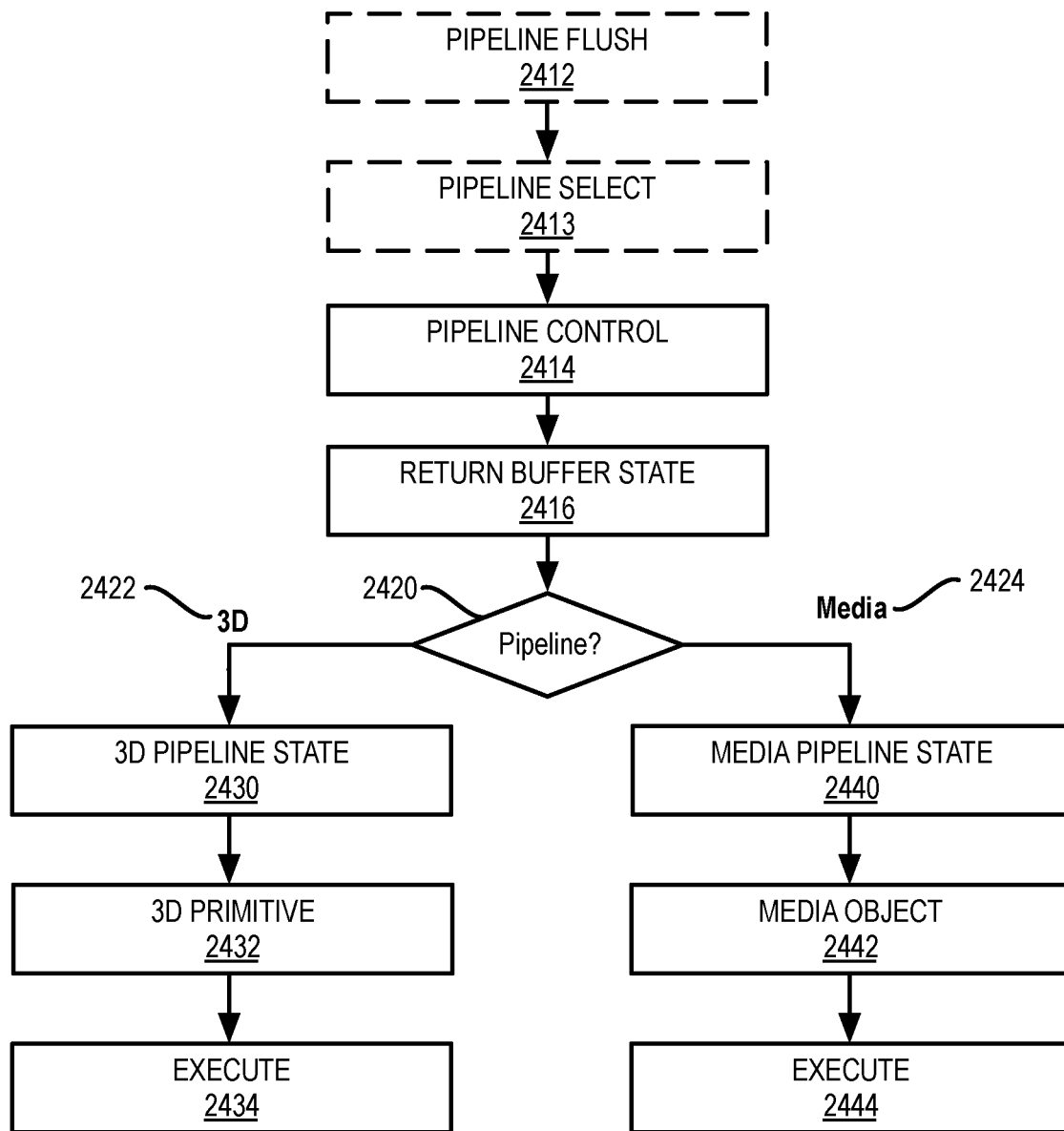
FIG. 24B  GRAPHICS PROCESSOR COMMAND SEQUENCE
2410

SCHEDULING CONFIGURATION FOR DEEP LEARNING NETWORKS

CROSS-REFERENCE

This application is a continuation of U.S. application Ser. No. 15/499,900 filed on Apr. 28, 2017, and is hereby incorporated by reference in its entirety.

FIELD

Embodiments relate generally to data processing and more particularly to machine learning processing via a general-purpose graphics processing unit.

BACKGROUND

Machine learning has been successful at solving many kinds of tasks. The computations that arise when training and using machine learning algorithms (e.g., neural networks) lend themselves naturally to efficient parallel implementations. Accordingly, parallel processors such as general-purpose graphic processing units (GPGPUs) have played a significant role in the practical implementation of deep neural networks. Parallel graphics processors with single instruction, multiple thread (SIMT) architectures are designed to maximize the amount of parallel processing in the graphics pipeline. In an SIMT architecture, groups of parallel threads attempt to execute program instructions synchronously together as often as possible to increase processing efficiency. The efficiency provided by parallel machine learning algorithm implementations allows the use of high capacity networks and enables those networks to be trained on larger datasets.

BRIEF DESCRIPTION OF THE DRAWINGS

So that the manner in which the features of the present embodiments can be understood in detail, a more particular description of the embodiments may be had by reference to the appended drawings. It is to be noted, however, that the appended drawings illustrate only typical embodiments and are therefore not to be considered limiting of its scope.

FIG. 22 is a block diagram illustrating graphics processor instruction formats according to some embodiments.

FIG. 24A-24B illustrate a graphics processor command format and command sequence, according to some embodiments.

DETAILED DESCRIPTION

In the following description, numerous specific details are set forth in order to provide a thorough understanding of various embodiments. However, various embodiments may be practiced without the specific details. In other instances, well-known methods, procedures, components, and circuits have not been described in detail so as not to obscure the particular embodiments. Further, various aspects of embodiments may be performed using various means, such as integrated semiconductor circuits ("hardware"), computer-readable instructions organized into one or more programs ("software"), or some combination of hardware and software. For the purposes of this disclosure reference to "logic" shall mean either hardware, software, firmware, or some combination thereof.

Some embodiments discussed herein may be applied in any processor (such as GPCPU, CPU, GPU, etc.), graphics controllers, etc. Other embodiments are also disclosed and claimed.

Further, some embodiments may be applied in computing systems that include one or more processors (e.g., with one or more processor cores), such as those discussed herein, including for example mobile computing devices, e.g., a smartphone, tablet, UMPC (Ultra-Mobile Personal Computer), laptop computer, Ultrabook™ computing device, wearable devices (such as a smart watch or smart glasses), etc.

In some embodiments, a graphics processing unit (GPU) is communicatively coupled to host/processor cores to accelerate graphics operations, machine-learning operations, pattern analysis operations, and various general purpose GPU (GPGPU) functions. The GPU may be communicatively coupled to the host processor/cores over a bus or another interconnect (e.g., a high-speed interconnect such as PCIe or NVLink). In other embodiments, the GPU may be integrated on the same package or chip as the cores and communicatively coupled to the cores over an internal processor bus/interconnect (i.e., internal to the package or chip). Regardless of the manner in which the GPU is connected, the processor cores may allocate work to the GPU in the form of sequences of commands/instructions contained in a work descriptor. The GPU then uses dedicated circuitry/logic for efficiently processing these commands/instructions.

In the following description, numerous specific details are set forth to provide a more thorough understanding. However, it will be apparent to one of skill in the art that the embodiments described herein may be practiced without one or more of these specific details. In other instances, well-known features have not been described to avoid obscuring the details of the present embodiments.

System Overview

Figure 1:
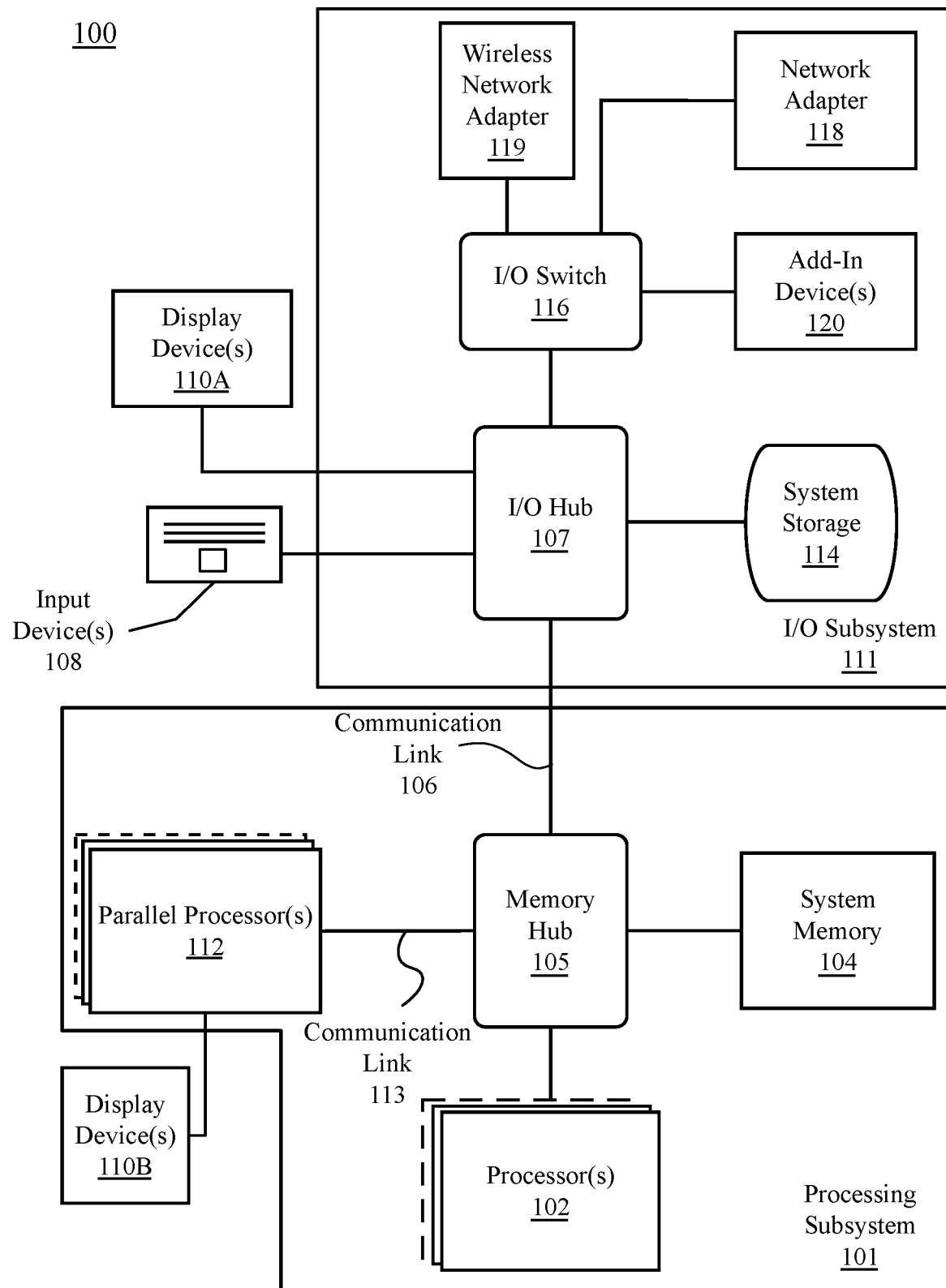
FIG. 1 is a block diagram illustrating a computer system configured to implement one or more aspects of the embodiments described herein.

FIG. 1 is a block diagram illustrating a computing system 100 configured to implement one or more aspects of the embodiments described herein. The computing system 100 includes a processing subsystem 101 having one or more processor(s) 102 and a system memory 104 communicating via an interconnection path that may include a memory hub 105. The memory hub 105 may be a separate component within a chipset component or may be integrated within the one or more processor(s) 102. The memory hub 105 couples with an I/O subsystem 111 via a communication link 106. The I/O subsystem 111 includes an I/O hub 107 that can enable the computing system 100 to receive input from one or more input device(s) 108. Additionally, the I/O hub 107 can enable a display controller, which may be included in the one or more processor(s) 102, to provide outputs to one or more display device(s) 110A. In one embodiment the one or more display device(s) 110A coupled with the I/O hub 107 can include a local, internal, or embedded display device.

In one embodiment the processing subsystem 101 includes one or more parallel processor(s) 112 coupled to memory hub 105 via a bus or other communication link 113. The communication link 113 may be one of any number of standards based communication link technologies or protocols, such as, but not limited to PCI Express, or may be a vendor specific communications interface or communications fabric. In one embodiment the one or more parallel processor(s) 112 form a computationally focused parallel or vector processing system that an include a large number of processing cores and/or processing clusters, such as a many integrated core (MIC) processor. In one embodiment the one or more parallel processor(s) 112 form a graphics processing subsystem that can output pixels to one of the one or more display device(s) 110A coupled via the I/O hub 107. The one or more parallel processor(s) 112 can also include a display controller and display interface (not shown) to enable a direct connection to one or more display device(s) 110B.

Within the I/O subsystem 111, a system storage unit 114 can connect to the I/O hub 107 to provide a storage mechanism for the computing system 100. An I/O switch 116 can be used to provide an interface mechanism to enable connections between the I/O hub 107 and other components, such as a network adapter 118 and/or wireless network adapter 119 that may be integrated into the platform, and various other devices that can be added via one or more add-in device(s) 120. The network adapter 118 can be an Ethernet adapter or another wired network adapter. The wireless network adapter 119 can include one or more of a Wi-Fi, Bluetooth, near field communication (NFC), or other network device that includes one or more wireless radios.

The computing system 100 can include other components not explicitly shown, including USB or other port connections, optical storage drives, video capture devices, and the like, may also be connected to the I/O hub 107. Communication paths interconnecting the various components in FIG. 1 may be implemented using any suitable protocols, such as PCI (Peripheral Component Interconnect) based protocols (e.g., PCI-Express), or any other bus or point-to-point communication interfaces and/or protocol(s), such as the NV-Link high-speed interconnect, or interconnect protocols known in the art.

In one embodiment, the one or more parallel processor(s) 112 incorporate circuitry optimized for graphics and video processing, including, for example, video output circuitry, and constitutes a graphics processing unit (GPU). In another embodiment, the one or more parallel processor(s) 112 incorporate circuitry optimized for general purpose processing, while preserving the underlying computational architecture, described in greater detail herein. In yet another embodiment, components of the computing system 100 may be integrated with one or more other system elements on a single integrated circuit. For example, the one or more parallel processor(s) 112, memory hub 105, processor(s) 102, and I/O hub 107 can be integrated into a system on chip (SoC) integrated circuit. Alternatively, the components of the computing system 100 can be integrated into a single package to form a system in package (SIP) configuration. In one embodiment at least a portion of the components of the computing system 100 can be integrated into a multi-chip module (MCM), which can be interconnected with other multi-chip modules into a modular computing system.

It will be appreciated that the computing system 100 shown herein is illustrative and that variations and modifications are possible. The connection topology, including the number and arrangement of bridges, the number of processor(s) 102, and the number of parallel processor(s) 112, may be modified as desired. For instance, in some embodiments, system memory 104 is connected to the processor(s) 102 directly rather than through a bridge, while other devices communicate with system memory 104 via the memory hub 105 and the processor(s) 102. In other alternative topologies, the parallel processor(s) 112 are connected to the I/O hub 107 or directly to one of the one or more processor(s) 102, rather than to the memory hub 105. In other embodiments, the I/O hub 107 and memory hub 105 may be integrated into a single chip. Some embodiments may include two or more sets of processor(s) 102 attached via multiple sockets, which can couple with two or more instances of the parallel processor(s) 112.

Some of the particular components shown herein are optional and may not be included in all implementations of the computing system 100. For example, any number of add-in cards or peripherals may be supported, or some components may be eliminated. Furthermore, some architectures may use different terminology for components similar to those illustrated in FIG. 1. For example, the memory hub 105 may be referred to as a Northbridge in some architectures, while the I/O hub 107 may be referred to as a Southbridge.

Figure 2A:
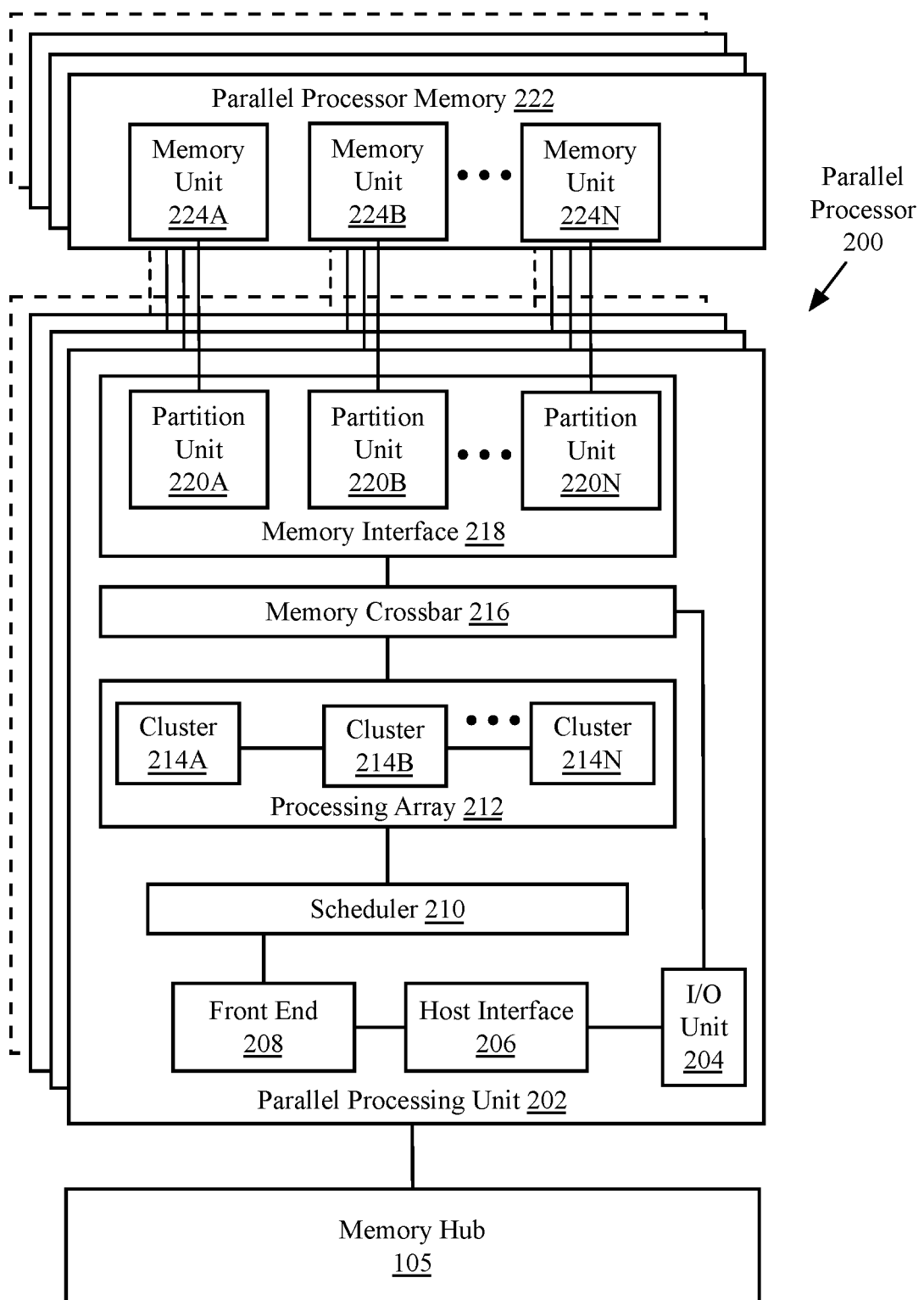
FIG. 2A-2D illustrate a parallel processor components, according to an embodiment.

FIG. 2A illustrates a parallel processor 200, according to an embodiment. The various components of the parallel processor 200 may be implemented using one or more integrated circuit devices, such as programmable processors, application specific integrated circuits (ASICs), or field programmable gate arrays (FPGA). The illustrated parallel processor 200 is a variant of the one or more parallel processor(s) 112 shown in FIG. 1, according to an embodiment.

In one embodiment the parallel processor 200 includes a parallel processing unit 202. The parallel processing unit includes an I/O unit 204 that enables communication with other devices, including other instances of the parallel processing unit 202. The I/O unit 204 may be directly connected to other devices. In one embodiment the I/O unit 204 connects with other devices via the use of a hub or switch interface, such as memory hub 105. The connections between the memory hub 105 and the I/O unit 204 form a communication link 113. Within the parallel processing unit 202, the I/O unit 204 connects with a host interface 206 and a memory crossbar 216, where the host interface 206 receives commands directed to performing processing operations and the memory crossbar 216 receives commands directed to performing memory operations.

When the host interface 206 receives a command buffer via the I/O unit 204, the host interface 206 can direct work operations to perform those commands to a front end 208. In one embodiment the front end 208 couples with a scheduler 210, which is configured to distribute commands or other work items to a processing cluster array 212. In one embodiment the scheduler 210 ensures that the processing cluster array 212 is properly configured and in a valid state before tasks are distributed to the processing clusters of the processing cluster array 212.

The processing cluster array 212 can include up to "N" processing clusters (e.g., cluster 214A, cluster 214B, through cluster 214N). Each cluster 214A-214N of the processing cluster array 212 can execute a large number of concurrent threads. The scheduler 210 can allocate work to the clusters 214A-214N of the processing cluster array 212 using various scheduling and/or work distribution algorithms, which may vary depending on the workload arising for each type of program or computation. The scheduling can be handled dynamically by the scheduler 210, or can be assisted in part by compiler logic during compilation of program logic configured for execution by the processing cluster array 212. In one embodiment, different clusters 214A-214N of the processing cluster array 212 can be allocated for processing different types of programs or for performing different types of computations.

The processing cluster array 212 can be configured to perform various types of parallel processing operations. In one embodiment the processing cluster array 212 is configured to perform general-purpose parallel compute operations. For example, the processing cluster array 212 can include logic to execute processing tasks including filtering of video and/or audio data, performing modeling operations, including physics operations, and performing data transformations.

In one embodiment the processing cluster array 212 is configured to perform parallel graphics processing operations. In embodiments in which the parallel processor 200 is configured to perform graphics processing operations, the processing cluster array 212 can include additional logic to support the execution of such graphics processing operations, including, but not limited to texture sampling logic to perform texture operations, as well as tessellation logic and other vertex processing logic. Additionally, the processing cluster array 212 can be configured to execute graphics processing related shader programs such as, but not limited to vertex shaders, tessellation shaders, geometry shaders, and pixel shaders. The parallel processing unit 202 can transfer data from system memory via the I/O unit 204 for processing. During processing the transferred data can be stored to on-chip memory (e.g., parallel processor memory 222) during processing, then written back to system memory.

In one embodiment, when the parallel processing unit 202 is used to perform graphics processing, the scheduler 210 can be configured to divide the processing workload into approximately equal sized tasks, to better enable distribution of the graphics processing operations to multiple clusters 214A-214N of the processing cluster array 212. In some embodiments, portions of the processing cluster array 212 can be configured to perform different types of processing. For example a first portion may be configured to perform vertex shading and topology generation, a second portion may be configured to perform tessellation and geometry shading, and a third portion may be configured to perform pixel shading or other screen space operations, to produce a rendered image for display. Intermediate data produced by one or more of the clusters 214A-214N may be stored in buffers to allow the intermediate data to be transmitted between clusters 214A-214N for further processing.

During operation, the processing cluster array 212 can receive processing tasks to be executed via the scheduler 210, which receives commands defining processing tasks from front end 208. For graphics processing operations, processing tasks can include indices of data to be processed, e.g., surface (patch) data, primitive data, vertex data, and/or pixel data, as well as state parameters and commands defining how the data is to be processed (e.g., what program is to be executed). The scheduler 210 may be configured to fetch the indices corresponding to the tasks or may receive the indices from the front end 208. The front end 208 can be configured to ensure the processing cluster array 212 is configured to a valid state before the workload specified by incoming command buffers (e.g., batch-buffers, push buffers, etc.) is initiated.

Each of the one or more instances of the parallel processing unit 202 can couple with parallel processor memory 222. The parallel processor memory 222 can be accessed via the memory crossbar 216, which can receive memory requests from the processing cluster array 212 as well as the I/O unit 204. The memory crossbar 216 can access the parallel processor memory 222 via a memory interface 218. The memory interface 218 can include multiple partition units (e.g., partition unit 220A, partition unit 220B, through partition unit 220N) that can each couple to a portion (e.g., memory unit) of parallel processor memory 222. In one implementation the number of partition units 220A-220N is configured to be equal to the number of memory units, such that a first partition unit 220A has a corresponding first memory unit 224A, a second partition unit 220B has a corresponding memory unit 224B, and an Nth partition unit 220N has a corresponding Nth memory unit 224N. In other embodiments, the number of partition units 220A-220N may not be equal to the number of memory devices.

In various embodiments, the memory units 224A-224N can include various types of memory devices, including dynamic random access memory (DRAM) or graphics random access memory, such as synchronous graphics random access memory (SGRAM), including graphics double data rate (GDDR) memory. In one embodiment, the memory units 224A-224N may also include 3D stacked memory, including but not limited to high bandwidth memory (HBM). Persons skilled in the art will appreciate that the specific implementation of the memory units 224A-224N can vary, and can be selected from one of various conventional designs. Render targets, such as frame buffers or texture maps may be stored across the memory units 224A-224N, allowing partition units 220A-220N to write portions of each render target in parallel to efficiently use the available bandwidth of parallel processor memory 222. In some embodiments, a local instance of the parallel processor memory 222 may be excluded in favor of a unified memory design that utilizes system memory in conjunction with local cache memory.

In one embodiment, any one of the clusters 214A-214N of the processing cluster array 212 can process data that will be written to any of the memory units 224A-224N within parallel processor memory 222. The memory crossbar 216 can be configured to transfer the output of each cluster 214A-214N to any partition unit 220A-220N or to another cluster 214A-214N, which can perform additional processing operations on the output. Each cluster 214A-214N can communicate with the memory interface 218 through the memory crossbar 216 to read from or write to various external memory devices. In one embodiment the memory crossbar 216 has a connection to the memory interface 218 to communicate with the I/O unit 204, as well as a connection to a local instance of the parallel processor memory 222, enabling the processing units within the different processing clusters 214A-214N to communicate with system memory or other memory that is not local to the parallel processing unit 202. In one embodiment the memory crossbar 216 can use virtual channels to separate traffic streams between the clusters 214A-214N and the partition units 220A-220N.

While a single instance of the parallel processing unit 202 is illustrated within the parallel processor 200, any number of instances of the parallel processing unit 202 can be included. For example, multiple instances of the parallel processing unit 202 can be provided on a single add-in card, or multiple add-in cards can be interconnected. The different instances of the parallel processing unit 202 can be configured to inter-operate even if the different instances have different numbers of processing cores, different amounts of local parallel processor memory, and/or other configuration differences. For example and in one embodiment, some instances of the parallel processing unit 202 can include higher precision floating point units relative to other instances. Systems incorporating one or more instances of the parallel processing unit 202 or the parallel processor 200 can be implemented in a variety of configurations and form factors, including but not limited to desktop, laptop, or handheld personal computers, servers, workstations, game consoles, and/or embedded systems.

Figure 2B:
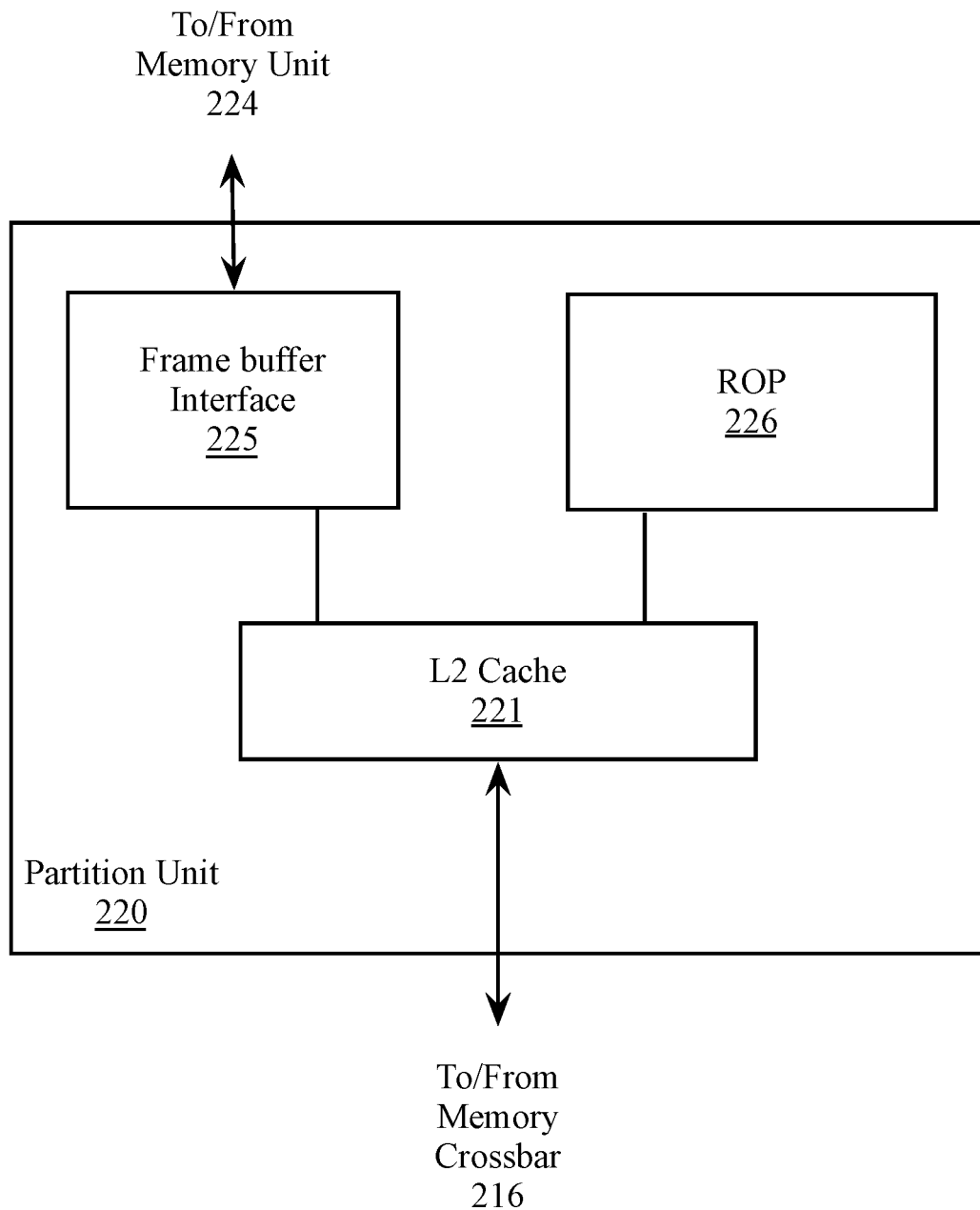

FIG. 2B is a block diagram of a partition unit 220, according to an embodiment. In one embodiment the partition unit 220 is an instance of one of the partition units 220A-220N of FIG. 2A. As illustrated, the partition unit 220 includes an L2 cache 221, a frame buffer interface 225, and a ROP 226 (raster operations unit). The L2 cache 221 is a read/write cache that is configured to perform load and store operations received from the memory crossbar 216 and ROP 226. Read misses and urgent write-back requests are output by L2 cache 221 to frame buffer interface 225 for processing. Dirty updates can also be sent to the frame buffer via the frame buffer interface 225 for opportunistic processing. In one embodiment the frame buffer interface 225 interfaces with one of the memory units in parallel processor memory, such as the memory units 224A-224N of FIG. 2 (e.g., within parallel processor memory 222).

In graphics applications, the ROP 226 is a processing unit that performs raster operations such as stencil, z test, blending, and the like. The ROP 226 then outputs processed graphics data that is stored in graphics memory. In some embodiments the ROP 226 includes compression logic to compress z or color data that is written to memory and decompress z or color data that is read from memory. In some embodiments, the ROP 226 is included within each processing cluster (e.g., cluster 214A-214N of FIG. 2) instead of within the partition unit 220. In such embodiment, read and write requests for pixel data are transmitted over the memory crossbar 216 instead of pixel fragment data. The processed graphics data may be displayed on a display device, such as one of the one or more display device(s) 110 of FIG. 1, routed for further processing by the processor(s) 102, or routed for further processing by one of the processing entities within the parallel processor 200 of FIG. 2A.

Figure 2C:
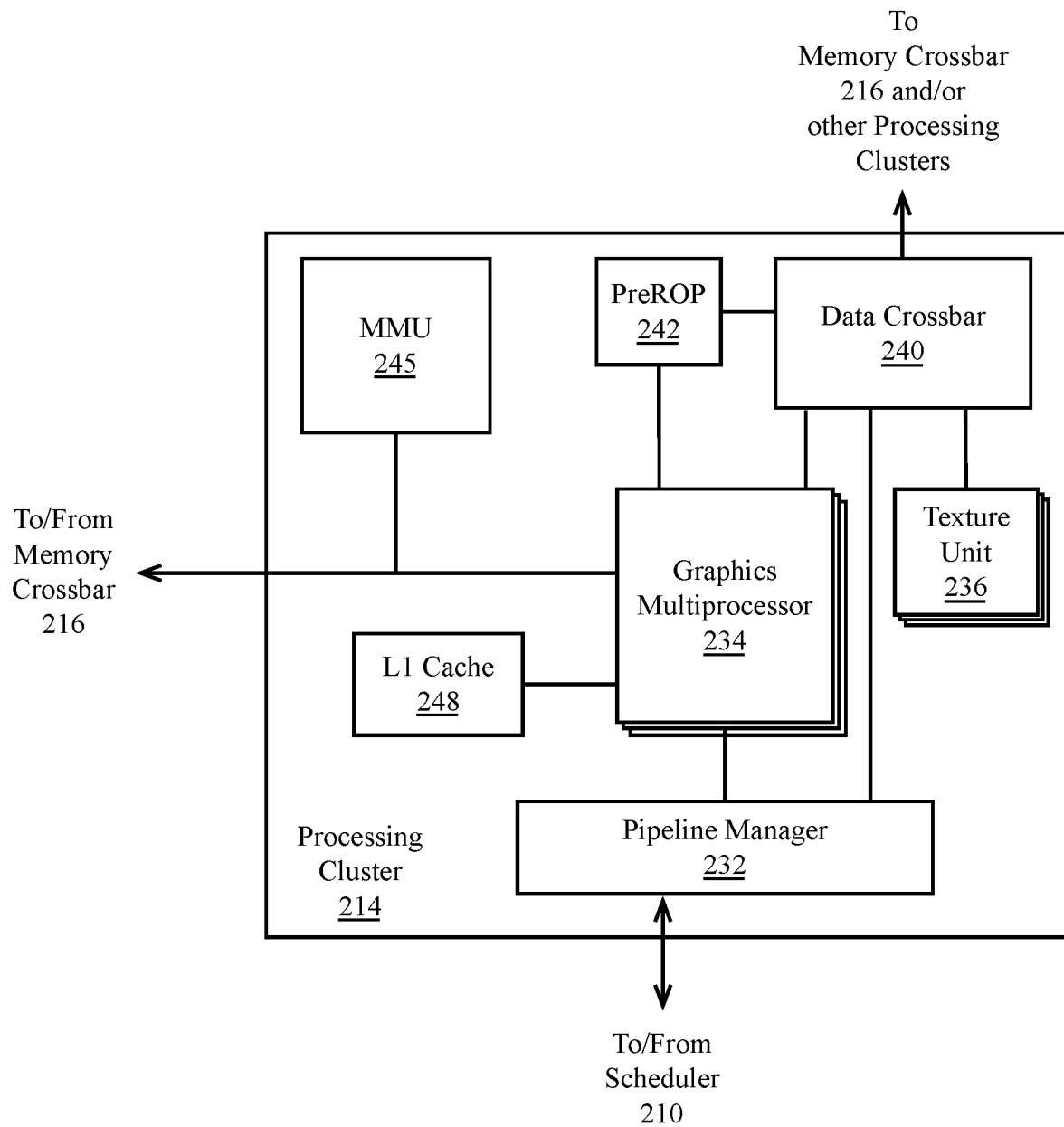

FIG. 2C is a block diagram of a processing cluster 214 within a parallel processing unit, according to an embodiment. In one embodiment the processing cluster is an instance of one of the processing clusters 214A-214N of FIG. 2A. The processing cluster 214 can be configured to execute many threads in parallel, where the term "thread" refers to an instance of a particular program executing on a particular set of input data. In some embodiments, single-instruction, multiple-data (SIMD) instruction issue techniques are used to support parallel execution of a large number of threads without providing multiple independent instruction units. In other embodiments, single-instruction, multiple-thread (SIMT) techniques are used to support parallel execution of a large number of generally synchronized threads, using a common instruction unit configured to issue instructions to a set of processing engines within each one of the processing clusters. Unlike a SIMD execution regime, where all processing engines typically execute identical instructions, SIMT execution allows different threads to more readily follow divergent execution paths through a given thread program. Persons skilled in the art will understand that a SIMD processing regime represents a functional subset of a SIMT processing regime.

Operation of the processing cluster 214 can be controlled via a pipeline manager 232 that distributes processing tasks to SIMT parallel processors. The pipeline manager 232 receives instructions from the scheduler 210 of FIG. 2 and manages execution of those instructions via a graphics multiprocessor 234 and/or a texture unit 236. The illustrated graphics multiprocessor 234 is an exemplary instance of a SIMT parallel processor. However, various types of SIMT parallel processors of differing architectures may be included within the processing cluster 214. One or more instances of the graphics multiprocessor 234 can be included within a processing cluster 214. The graphics multiprocessor 234 can process data and a data crossbar 240 can be used to distribute the processed data to one of multiple possible destinations, including other shader units. The pipeline manager 232 can facilitate the distribution of processed data by specifying destinations for processed data to be distributed vis the data crossbar 240.

Each graphics multiprocessor 234 within the processing cluster 214 can include an identical set of functional execution logic (e.g., arithmetic logic units, load-store units, etc.). The functional execution logic can be configured in a pipelined manner in which new instructions can be issued before previous instructions are complete. The functional execution logic supports a variety of operations including integer and floating point arithmetic, comparison operations, Boolean operations, bit-shifting, and computation of various algebraic functions. In one embodiment the same functional-unit hardware can be leveraged to perform different operations and any combination of functional units may be present.

The instructions transmitted to the processing cluster 214 constitutes a thread. A set of threads executing across the set of parallel processing engines is a thread group. A thread group executes the same program on different input data. Each thread within a thread group can be assigned to a different processing engine within a graphics multiprocessor 234. A thread group may include fewer threads than the number of processing engines within the graphics multiprocessor 234. When a thread group includes fewer threads than the number of processing engines, one or more of the processing engines may be idle during cycles in which that thread group is being processed. A thread group may also include more threads than the number of processing engines within the graphics multiprocessor 234. When the thread group includes more threads than the number of processing engines within the graphics multiprocessor 234, processing can be performed over consecutive clock cycles. In one embodiment multiple thread groups can be executed concurrently on a graphics multiprocessor 234.

In one embodiment the graphics multiprocessor 234 includes an internal cache memory to perform load and store operations. In one embodiment, the graphics multiprocessor 234 can forego an internal cache and use a cache memory (e.g., L1 cache 248) within the processing cluster 214. Each graphics multiprocessor 234 also has access to L2 caches within the partition units (e.g., partition units 220A-220N of FIG. 2) that are shared among all processing clusters 214 and may be used to transfer data between threads. The graphics multiprocessor 234 may also access off-chip global memory, which can include one or more of local parallel processor memory and/or system memory. Any memory external to the parallel processing unit 202 may be used as global memory. Embodiments in which the processing cluster 214 includes multiple instances of the graphics multiprocessor 234 can share common instructions and data, which may be stored in the L1 cache 308.

Each processing cluster 214 may include an MMU 245 (memory management unit) that is configured to map virtual addresses into physical addresses. In other embodiments, one or more instances of the MMU 245 may reside within the memory interface 218 of FIG. 2A. The MMU 245 includes a set of page table entries (PTEs) used to map a virtual address to a physical address of a tile and optionally a cache line index. The MMU 245 may include address translation lookaside buffers (TLB) or caches that may reside within the graphics multiprocessor 234 or the L1 cache or processing cluster 214. The physical address is processed to distribute surface data access locality to allow efficient request interleaving among partition units. The cache line index may be used to determine whether a request for a cache line is a hit or miss.

In graphics and computing applications, a processing cluster 214 may be configured such that each graphics multiprocessor 234 is coupled to a texture unit 236 for performing texture mapping operations, e.g., determining texture sample positions, reading texture data, and filtering the texture data. Texture data is read from an internal texture L1 cache (not shown) or in some embodiments from the L1 cache within graphics multiprocessor 234 and is fetched from an L2 cache, local parallel processor memory, or system memory, as needed. Each graphics multiprocessor 234 outputs processed tasks to the data crossbar 240 to provide the processed task to another processing cluster 214 for further processing or to store the processed task in an L2 cache, local parallel processor memory, or system memory via the memory crossbar 216. A preROP 242 (pre-raster operations unit) is configured to receive data from graphics multiprocessor 234, direct data to ROP units, which may be located with partition units as described herein (e.g., partition units 220A-220N of FIG. 2). The preROP 242 unit can perform optimizations for color blending, organize pixel color data, and perform address translations.

It will be appreciated that the core architecture described herein is illustrative and that variations and modifications are possible. Any number of processing units, e.g., graphics multiprocessor 234, texture units 236, preROPs 242, etc., may be included within a processing cluster 214. Further, while only one processing cluster 214 is shown, a parallel processing unit as described herein may include any number of instances of the processing cluster 214. In one embodiment, each processing cluster 214 can be configured to operate independently of other processing clusters 214 using separate and distinct processing units, L1 caches, etc.

Figure 2D:
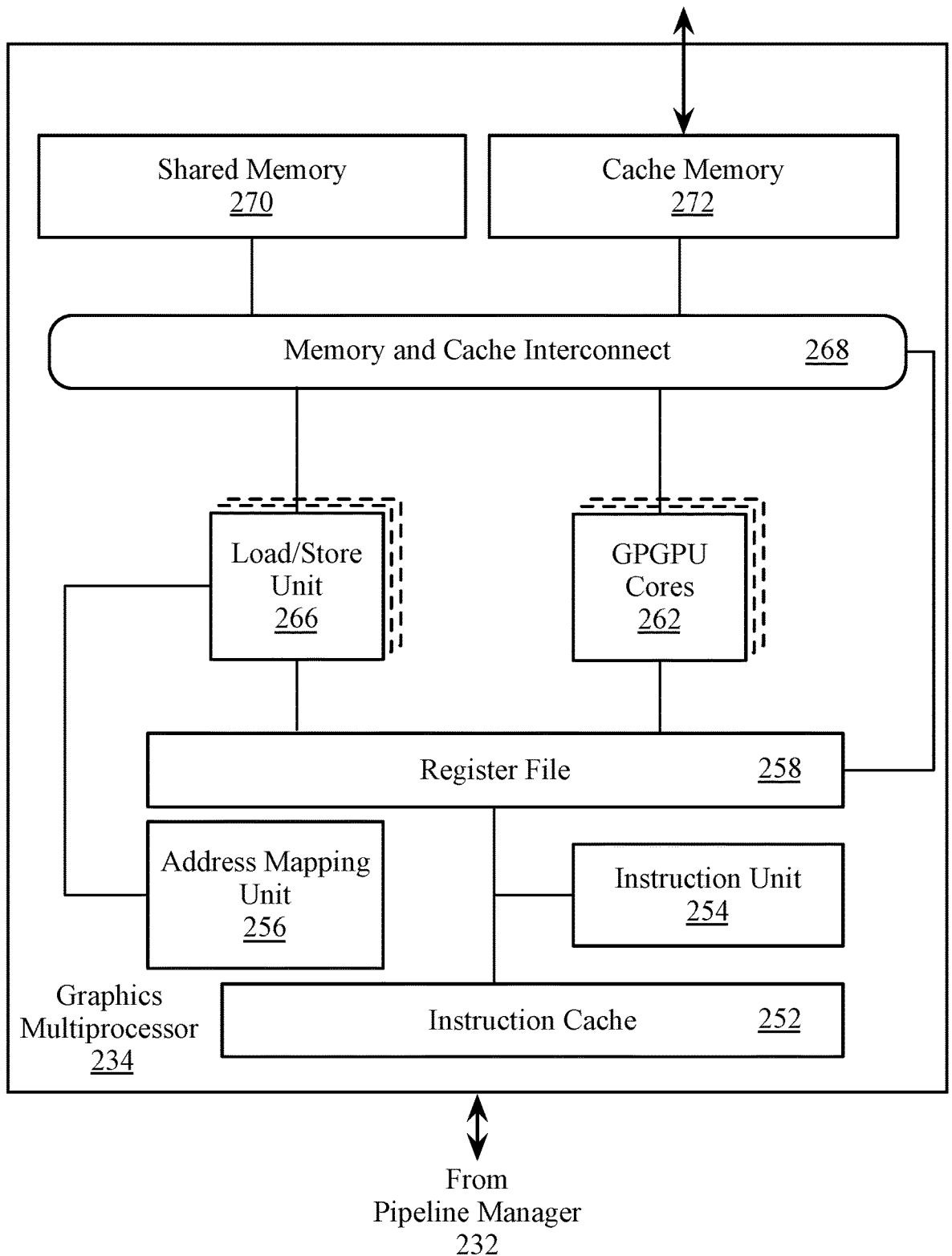

FIG. 2D shows a graphics multiprocessor 234, according to one embodiment. In such embodiment the graphics multiprocessor 234 couples with the pipeline manager 232 of the processing cluster 214. The graphics multiprocessor 234 has an execution pipeline including but not limited to an instruction cache 252, an instruction unit 254, an address mapping unit 256, a register file 258, one or more general purpose graphics processing unit (GPGPU) cores 262, and one or more load/store units 266. The GPGPU cores 262 and load/store units 266 are coupled with cache memory 272 and shared memory 270 via a memory and cache interconnect 268.

In one embodiment, the instruction cache 252 receives a stream of instructions to execute from the pipeline manager 232. The instructions are cached in the instruction cache 252 and dispatched for execution by the instruction unit 254. The instruction unit 254 can dispatch instructions as thread groups (e.g., warps), with each thread of the thread group assigned to a different execution unit within GPGPU core 262. An instruction can access any of a local, shared, or global address space by specifying an address within a unified address space. The address mapping unit 256 can be used to translate addresses in the unified address space into a distinct memory address that can be accessed by the load/store units 266.

The register file 258 provides a set of registers for the functional units of the graphics multiprocessor 234. The register file 258 provides temporary storage for operands connected to the data paths of the functional units (e.g., GPGPU cores 262, load/store units 266) of the graphics multiprocessor 234. In one embodiment, the register file 258 is divided between each of the functional units such that each functional unit is allocated a dedicated portion of the register file 258. In one embodiment, the register file 258 is divided between the different warps being executed by the graphics multiprocessor 234.

The GPGPU cores 262 can each include floating point units (FPUs) and/or integer arithmetic logic units (ALUs) that are used to execute instructions of the graphics multi-processor 234. The GPGPU cores 262 can be similar in architecture or can differ in architecture, according to embodiments. For example and in one embodiment, a first portion of the GPGPU cores 262 include a single precision FPU and an integer ALU while a second portion of the GPGPU cores include a double precision FPU. In one embodiment the FPUs can implement the IEEE 754-2008 standard for floating point arithmetic or enable variable precision floating point arithmetic. The graphics multiprocessor 234 can additionally include one or more fixed function or special function units to perform specific functions such as copy rectangle or pixel blending operations. In one embodiment one or more of the GPGPU cores can also include fixed or special function logic.

The memory and cache interconnect 268 is an interconnect network that connects each of the functional units of the graphics multiprocessor 234 to the register file 258 and to the shared memory 270. In one embodiment, the memory and cache interconnect 268 is a crossbar interconnect that allows the load/store unit 266 to implement load and store operations between the shared memory 270 and the register file 258. The register file 258 can operate at the same frequency as the GPGPU cores 262, thus data transfer between the GPGPU cores 262 and the register file 258 is very low latency. The shared memory 270 can be used to enable communication between threads that execute on the functional units within the graphics multiprocessor 234. The cache memory 272 can be used as a data cache for example, to cache texture data communicated between the functional units and the texture unit 236. The shared memory 270 can also be used as a program managed cached. Threads executing on the GPGPU cores 262 can programmatically store data within the shared memory in addition to the automatically cached data that is stored within the cache memory 272.

Figure 3A:
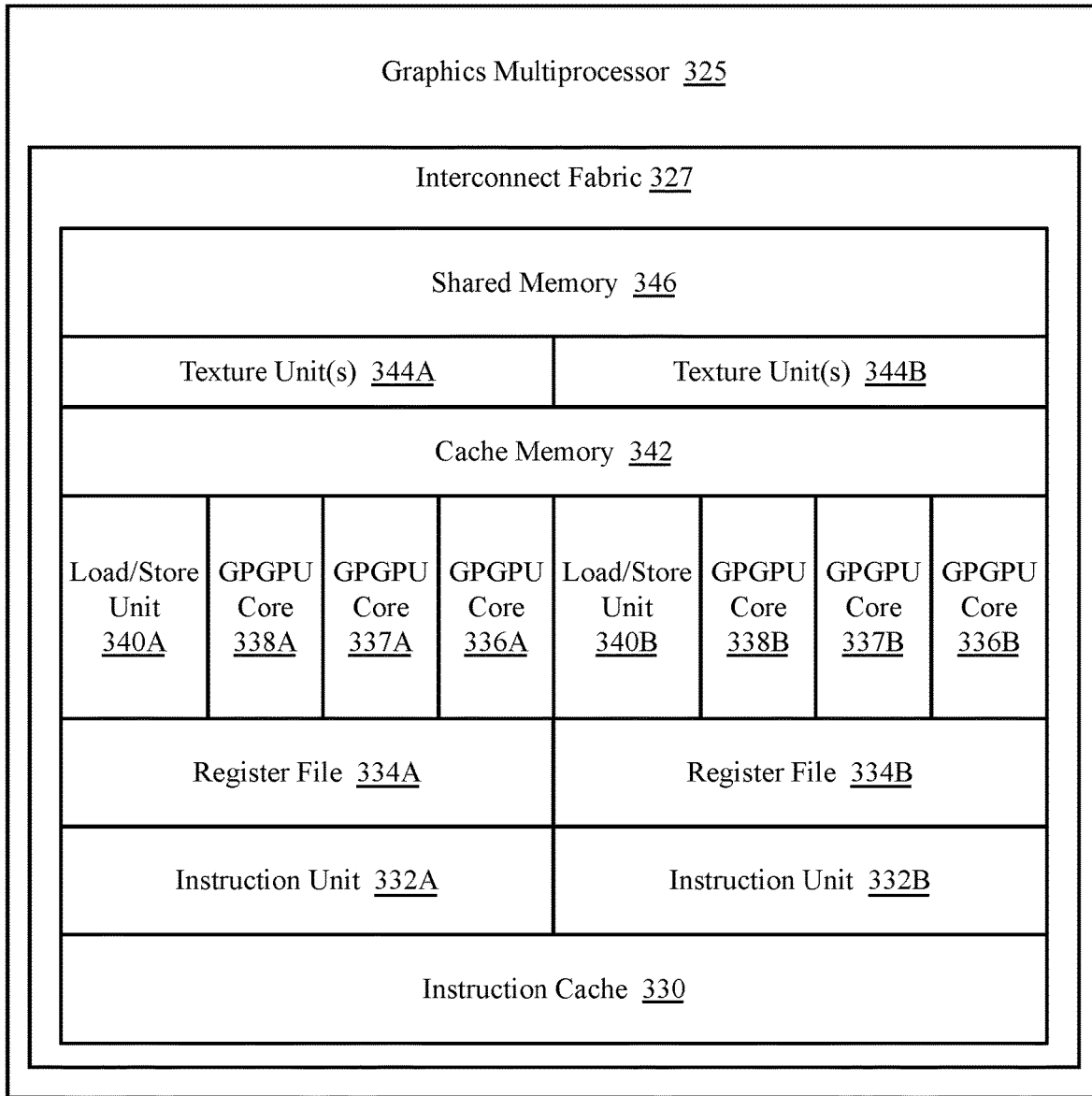
FIGS. 3A-3B are block diagrams of graphics multiprocessors, according to embodiments.
Figure 3B:
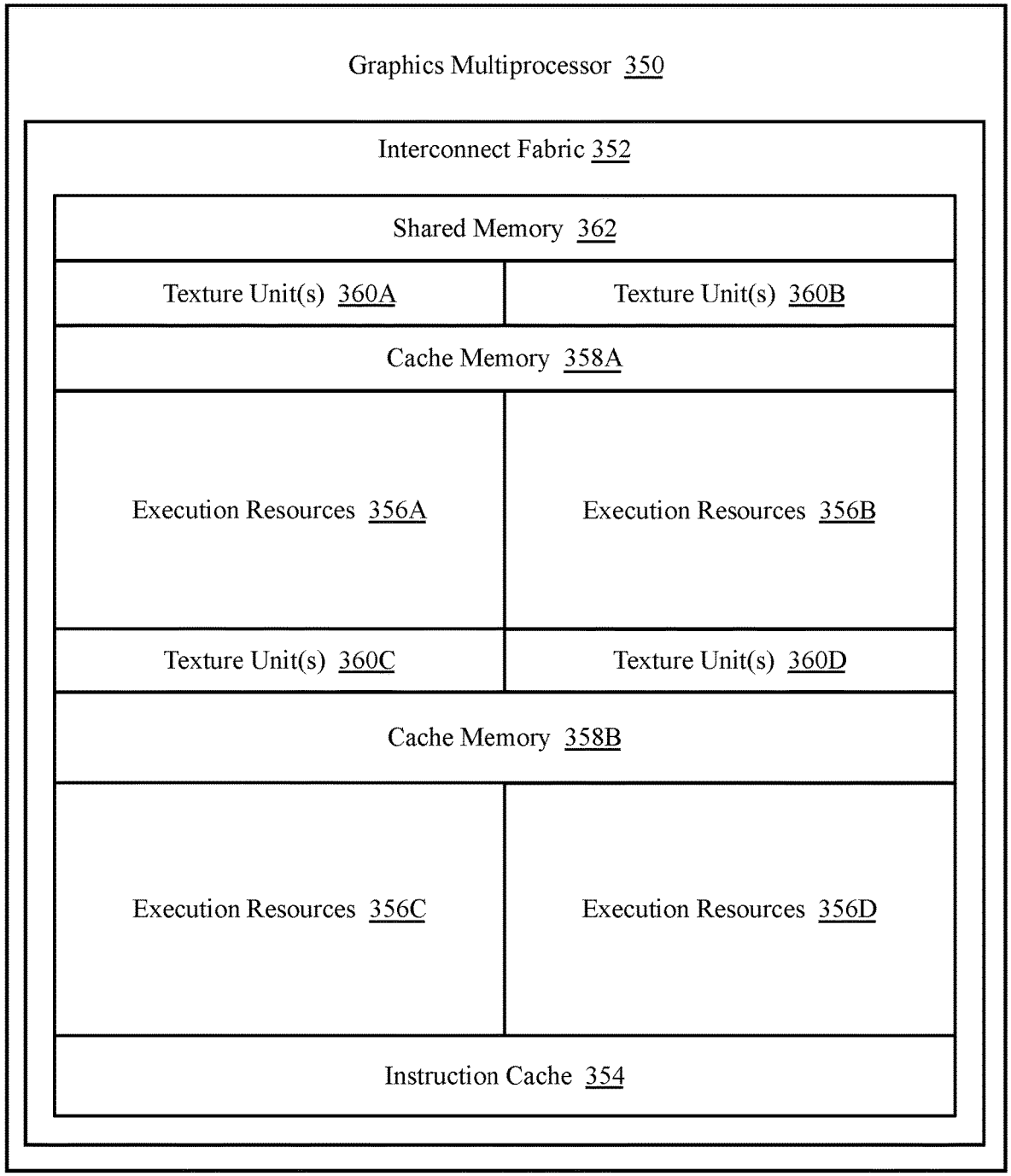

FIGS. 3A-3B illustrate additional graphics multiprocessors, according to embodiments. The illustrated graphics multiprocessors 325, 350 are variants of the graphics multiprocessor 234 of FIG. 2C. The illustrated graphics multiprocessors 325, 350 can be configured as a streaming multiprocessor (SM) capable of simultaneous execution of a large number of execution threads.

FIG. 3A shows a graphics multiprocessor 325 according to an additional embodiment. The graphics multiprocessor 325 includes multiple additional instances of execution resource units relative to the graphics multiprocessor 234 of FIG. 2D. For example, the graphics multiprocessor 325 can include multiple instances of the instruction unit 332A-332B, register file 334A-334B, and texture unit(s) 344A-344B. The graphics multiprocessor 325 also includes multiple sets of graphics or compute execution units (e.g., GPGPU core 336A-336B, GPGPU core 337A-337B, GPGPU core 338A-338B) and multiple sets of load/store units 340A-340B. In one embodiment the execution resource units have a common instruction cache 330, texture and/or data cache memory 342, and shared memory 346. The various components can communicate via an interconnect fabric 327. In one embodiment the interconnect fabric 327 includes one or more crossbar switches to enable communication between the various components of the graphics multiprocessor 325.

FIG. 3B shows a graphics multiprocessor 350 according to an additional embodiment. The graphics processor includes multiple sets of execution resources 356A-356D, where each set of execution resource includes multiple instruction units, register files, GPGPU cores, and load store units, as illustrated in FIG. 2D and FIG. 3A. The execution resources 356A-356D can work in concert with texture unit(s) 360A-360D for texture operations, while sharing an instruction cache 354, and shared memory 362. In one embodiment the execution resources 356A-356D can share an instruction cache 354 and shared memory 362, as well as multiple instances of a texture and/or data cache memory 358A-358B. The various components can communicate via an interconnect fabric 352 similar to the interconnect fabric 327 of FIG. 3A.

Persons skilled in the art will understand that the architecture described in FIGS. 1, 2A-2D, and 3A-3B are descriptive and not limiting as to the scope of the present embodiments. Thus, the techniques described herein may be implemented on any properly configured processing unit, including, without limitation, one or more mobile application processors, one or more desktop or server central processing units (CPUs) including multi-core CPUs, one or more parallel processing units, such as the parallel processing unit 202 of FIG. 2, as well as one or more graphics processors or special purpose processing units, without departure from the scope of the embodiments described herein.

In some embodiments a parallel processor or GPGPU as described herein is communicatively coupled to host/processor cores to accelerate graphics operations, machine-learning operations, pattern analysis operations, and various general purpose GPU (GPGPU) functions. The GPU may be communicatively coupled to the host processor/cores over a bus or other interconnect (e.g., a high speed interconnect such as PCIe or NVLink). In other embodiments, the GPU may be integrated on the same package or chip as the cores and communicatively coupled to the cores over an internal processor bus/interconnect (i.e., internal to the package or chip). Regardless of the manner in which the GPU is connected, the processor cores may allocate work to the GPU in the form of sequences of commands/instructions contained in a work descriptor. The GPU then uses dedicated circuitry/logic for efficiently processing these commands/instructions.

Techniques for GPU to Host Processor Interconnection

Figure 4A:
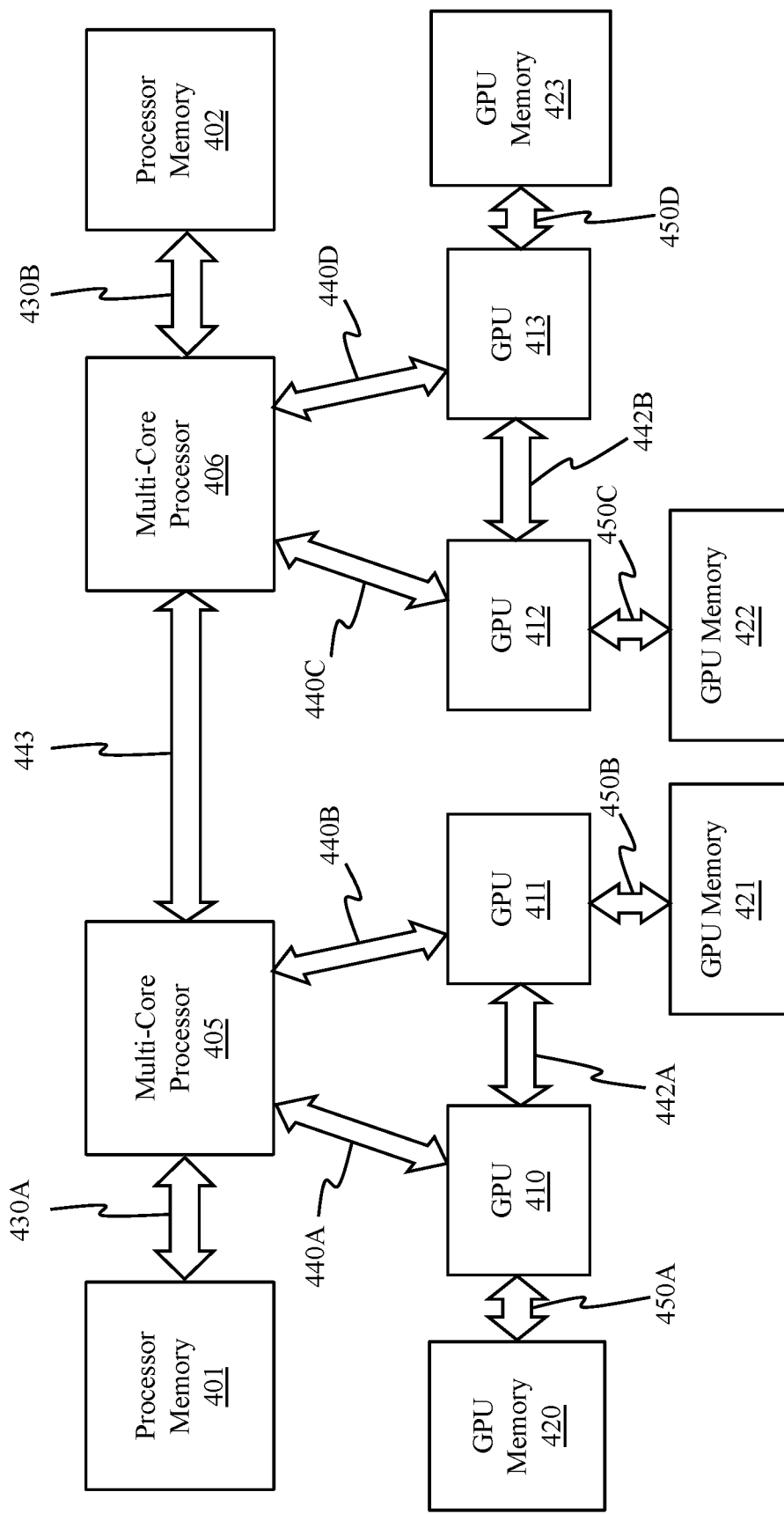
FIG. 4A-4F illustrate an exemplary architecture in which a plurality of GPUs is communicatively coupled to a plurality of multi-core processors.

FIG. 4A illustrates an exemplary architecture in which a plurality of GPUs 410-413 are communicatively coupled to a plurality of multi-core processors 405-406 over high-speed links 440A-440D (e.g., buses, point-to-point interconnects, etc.). In one embodiment, the high-speed links 440A-440D support a communication throughput of 4 GB/s, 30 GB/s, 80 GB/s or higher, depending on the implementation. Various interconnect protocols may be used including, but not limited to, PCIe 4.0 or 5.0 and NVLink 2.0. However, the underlying principles of the invention are not limited to any particular communication protocol or throughput.

In addition, in one embodiment, two or more of the GPUs 410-413 are interconnected over high-speed links 442A-442B, which may be implemented using the same or different protocols/links than those used for high-speed links 440A-440D. Similarly, two or more of the multi-core processors 405-406 may be connected over high speed link 433 which may be symmetric multi-processor (SMP) buses operating at 20 GB/s, 30 GB/s, 120 GB/s or higher. Alternatively, all communication between the various system components shown in FIG. 4A may be accomplished using the same protocols/links (e.g., over a common interconnection fabric). As mentioned, however, the underlying principles of the invention are not limited to any particular type of interconnect technology.

In one embodiment, each multi-core processor 405-406 is communicatively coupled to a processor memory 401-402, via memory interconnects 430A-430B, respectively, and each GPU 410-413 is communicatively coupled to GPU memory 420-423 over GPU memory interconnects 450A-

450D, respectively. The memory interconnects 430A-430B and 450A-450D may utilize the same or different memory access technologies. By way of example, and not limitation, the processor memories 401-402 and GPU memories 420-423 may be volatile memories such as dynamic random access memories (DRAMs) (including stacked DRAMs), Graphics DDR SDRAM (GDDR) (e.g., GDDR5, GDDR6), or High Bandwidth Memory (HBM) and/or may be non-volatile memories such as 3D XPoint or Nano-Ram. In one embodiment, some portion of the memories may be volatile memory and another portion may be non-volatile memory (e.g., using a two-level memory (2LM) hierarchy).

As described below, although the various processors 405-406 and GPUs 410-413 may be physically coupled to a particular memory 401-402, 420-423, respectively, a unified memory architecture may be implemented in which the same virtual system address space (also referred to as the "effective address" space) is distributed among all of the various physical memories. For example, processor memories 401-402 may each comprise 64 GB of the system memory address space and GPU memories 420-423 may each comprise 32 GB of the system memory address space (resulting in a total of 256 GB addressable memory in this example).

Figure 4B:
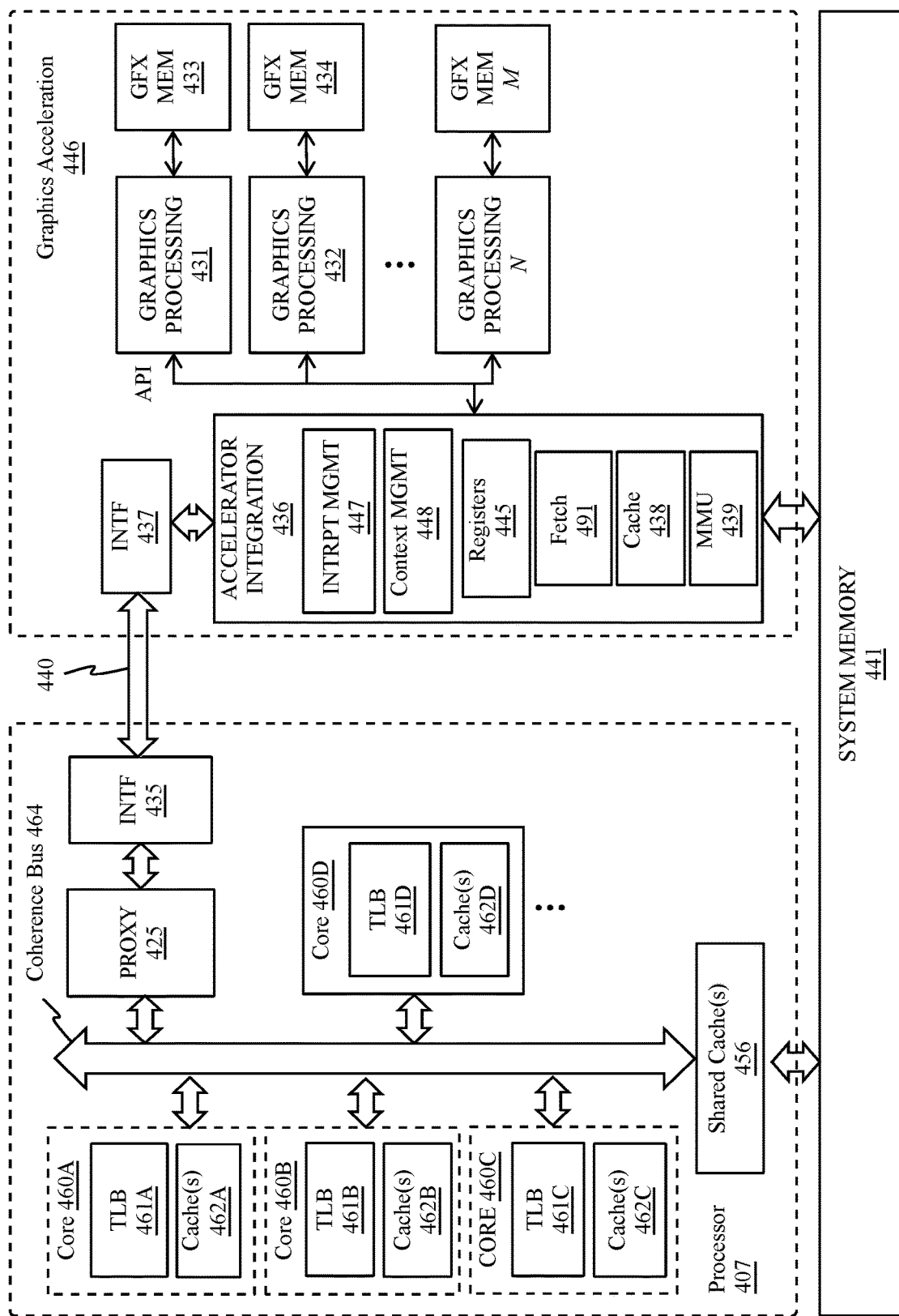

FIG. 4B illustrates additional details for an interconnection between a multi-core processor 407 and a graphics acceleration module 446 in accordance with one embodiment. The graphics acceleration module 446 may include one or more GPU chips integrated on a line card which is coupled to the processor 407 via the high-speed link 440. Alternatively, the graphics acceleration module 446 may be integrated on the same package or chip as the processor 407.

The illustrated processor 407 includes a plurality of cores 460A-460D, each with a translation lookaside buffer 461A-461D and one or more caches 462A-462D. The cores may include various other components for executing instructions and processing data which are not illustrated to avoid obscuring the underlying principles of the invention (e.g., instruction fetch units, branch prediction units, decoders, execution units, reorder buffers, etc.). The caches 462A-462D may comprise level 1 (L1) and level 2 (L2) caches. In addition, one or more shared caches 426 may be included in the caching hierarchy and shared by sets of the cores 460A-460D. For example, one embodiment of the processor 407 includes 24 cores, each with its own L1 cache, twelve shared L2 caches, and twelve shared L3 caches. In this embodiment, one of the L2 and L3 caches are shared by two adjacent cores. The processor 407 and the graphics accelerator integration module 446 connect with system memory 441, which may include processor memories 401-402

Coherency is maintained for data and instructions stored in the various caches 462A-462D, 456 and system memory 441 via inter-core communication over a coherence bus 464. For example, each cache may have cache coherency logic/circuitry associated therewith to communicate to over the coherence bus 464 in response to detected reads or writes to particular cache lines. In one implementation, a cache snooping protocol is implemented over the coherence bus 464 to snoop cache accesses. Cache snooping/coherency techniques are well understood by those of skill in the art and will not be described in detail here to avoid obscuring the underlying principles of the invention.

In one embodiment, a proxy circuit 425 communicatively couples the graphics acceleration module 446 to the coherence bus 464, allowing the graphics acceleration module 446 to participate in the cache coherence protocol as a peer of the cores. In particular, an interface 435 provides connectivity to the proxy circuit 425 over high-speed link 440 (e.g., a PCIe bus, NVLink, etc.) and an interface 437 connects the graphics acceleration module 446 to the link 440.

In one implementation, an accelerator integration circuit 436 provides cache management, memory access, context management, and interrupt management services on behalf of a plurality of graphics processing engines 431, 432, N of the graphics acceleration module 446. The graphics processing engines 431, 432, N may each comprise a separate graphics processing unit (GPU). Alternatively, the graphics processing engines 431, 432, N may comprise different types of graphics processing engines within a GPU such as graphics execution units, media processing engines (e.g., video encoders/decoders), samplers, and blit engines. In other words, the graphics acceleration module may be a GPU with a plurality of graphics processing engines 431-432, N or the graphics processing engines 431-432, N may be individual GPUs integrated on a common package, line card, or chip.

In one embodiment, the accelerator integration circuit 436 includes a memory management unit (MMU) 439 for performing various memory management functions such as virtual-to-physical memory translations (also referred to as effective-to-real memory translations) and memory access protocols for accessing system memory 441. The MMU 439 may also include a translation lookaside buffer (TLB) (not shown) for caching the virtual/effective to physical/real address translations. In one implementation, a cache 438 stores commands and data for efficient access by the graphics processing engines 431-432, N. In one embodiment, the data stored in cache 438 and graphics memories 433-434, N is kept coherent with the core caches 462A-462D, 456 and system memory 411. As mentioned, this may be accomplished via proxy circuit 425 which takes part in the cache coherency mechanism on behalf of cache 438 and memories 433-434, N (e.g., sending updates to the cache 438 related to modifications/accesses of cache lines on processor caches 462A-462D, 456 and receiving updates from the cache 438).

A set of registers 445 store context data for threads executed by the graphics processing engines 431-432, N and a context management circuit 448 manages the thread contexts. For example, the context management circuit 448 may perform save and restore operations to save and restore contexts of the various threads during contexts switches (e.g., where a first thread is saved and a second thread is stored so that the second thread can be execute by a graphics processing engine). For example, on a context switch, the context management circuit 448 may store current register values to a designated region in memory (e.g., identified by a context pointer). It may then restore the register values when returning to the context. In one embodiment, an interrupt management circuit 447 receives and processes interrupts received from system devices.

In one implementation, virtual/effective addresses from a graphics processing engine 431 are translated to real/physical addresses in system memory 411 by the MMU 439. One embodiment of the accelerator integration circuit 436 supports multiple (e.g., 4, 8, 16) graphics accelerator modules 446 and/or other accelerator devices. The graphics accelerator module 446 may be dedicated to a single application executed on the processor 407 or may be shared between multiple applications. In one embodiment, a virtualized graphics execution environment is presented in which the resources of the graphics processing engines 431-432, N are shared with multiple applications or virtual machines (VMs). The resources may be subdivided into "slices" which are allocated to different VMs and/or applications based on the processing requirements and priorities associated with the VMs and/or applications.

Thus, the accelerator integration circuit acts as a bridge to the system for the graphics acceleration module 446 and provides address translation and system memory cache services. In addition, the accelerator integration circuit 436 may provide virtualization facilities for the host processor to manage virtualization of the graphics processing engines, interrupts, and memory management.

Because hardware resources of the graphics processing engines 431-432, N are mapped explicitly to the real address space seen by the host processor 407, any host processor can address these resources directly using an effective address value. One function of the accelerator integration circuit 436, in one embodiment, is the physical separation of the graphics processing engines 431-432, N so that they appear to the system as independent units.

As mentioned, in the illustrated embodiment, one or more graphics memories 433-434, M are coupled to each of the graphics processing engines 431-432, N, respectively. The graphics memories 433-434, M store instructions and data being processed by each of the graphics processing engines 431-432, N. The graphics memories 433-434, M may be volatile memories such as DRAMs (including stacked DRAMs), GDDR memory (e.g., GDDR5, GDDR6), or HBM, and/or may be non-volatile memories such as 3D XPoint or Nano-Ram.

In one embodiment, to reduce data traffic over link 440, biasing techniques are used to ensure that the data stored in graphics memories 433-434, M is data which will be used most frequently by the graphics processing engines 431-432, N and preferably not used by the cores 460A-460D (at least not frequently). Similarly, the biasing mechanism attempts to keep data needed by the cores (and preferably not the graphics processing engines 431-432, N) within the caches 462A-462D, 456 of the cores and system memory 411.

Figure 4C:
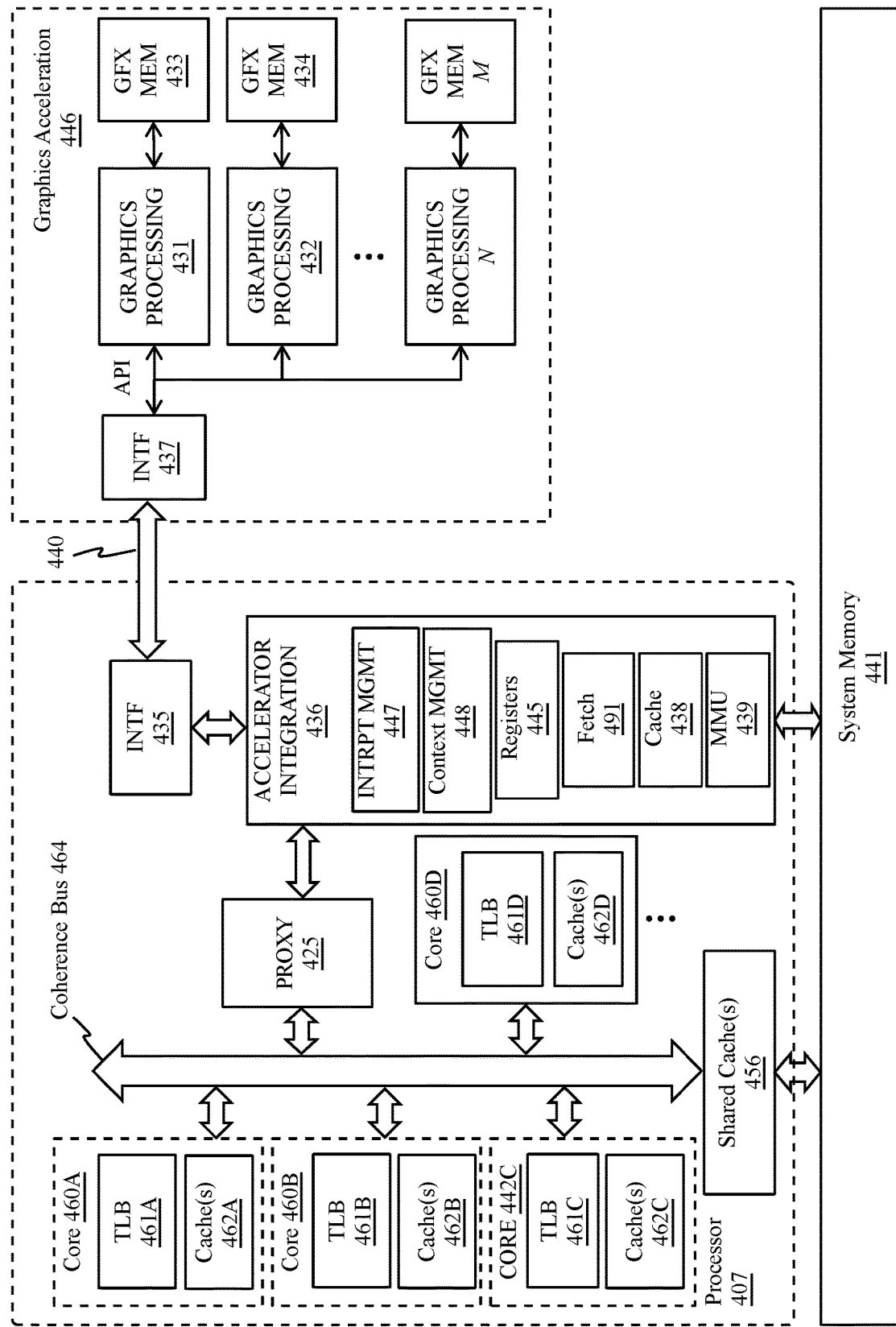

FIG. 4C illustrates another embodiment in which the accelerator integration circuit 436 is integrated within the processor 407. In this embodiment, the graphics processing engines 431-432, N communicate directly over the high-speed link 440 to the accelerator integration circuit 436 via interface 437 and interface 435 (which, again, may be utilize any form of bus or interface protocol). The accelerator integration circuit 436 may perform the same operations as those described with respect to FIG. 4B, but potentially at a higher throughput given its close proximity to the coherency bus 462 and caches 462A-462D, 426.

One embodiment supports different programming models including a dedicated-process programming model (no graphics acceleration module virtualization) and shared programming models (with virtualization). The latter may include programming models which are controlled by the accelerator integration circuit 436 and programming models which are controlled by the graphics acceleration module 446.

In one embodiment of the dedicated process model, graphics processing engines 431-432, N are dedicated to a single application or process under a single operating system. The single application can funnel other application requests to the graphics engines 431-432, N, providing virtualization within a VM/partition.

In the dedicated-process programming models, the graphics processing engines 431-432, N, may be shared by multiple VM/application partitions. The shared models require a system hypervisor to virtualize the graphics processing engines 431-432, N to allow access by each operating system. For single-partition systems without a hypervisor, the graphics processing engines 431-432, N are owned by the operating system. In both cases, the operating system can virtualize the graphics processing engines 431-432, N to provide access to each process or application.

For the shared programming model, the graphics acceleration module 446 or an individual graphics processing engine 431-432, N selects a process element using a process handle. In one embodiment, process elements are stored in system memory 411 and are addressable using the effective address to real address translation techniques described herein. The process handle may be an implementation-specific value provided to the host process when registering its context with the graphics processing engine 431-432, N (that is, calling system software to add the process element to the process element linked list). The lower 16-bits of the process handle may be the offset of the process element within the process element linked list.

Figure 4D:
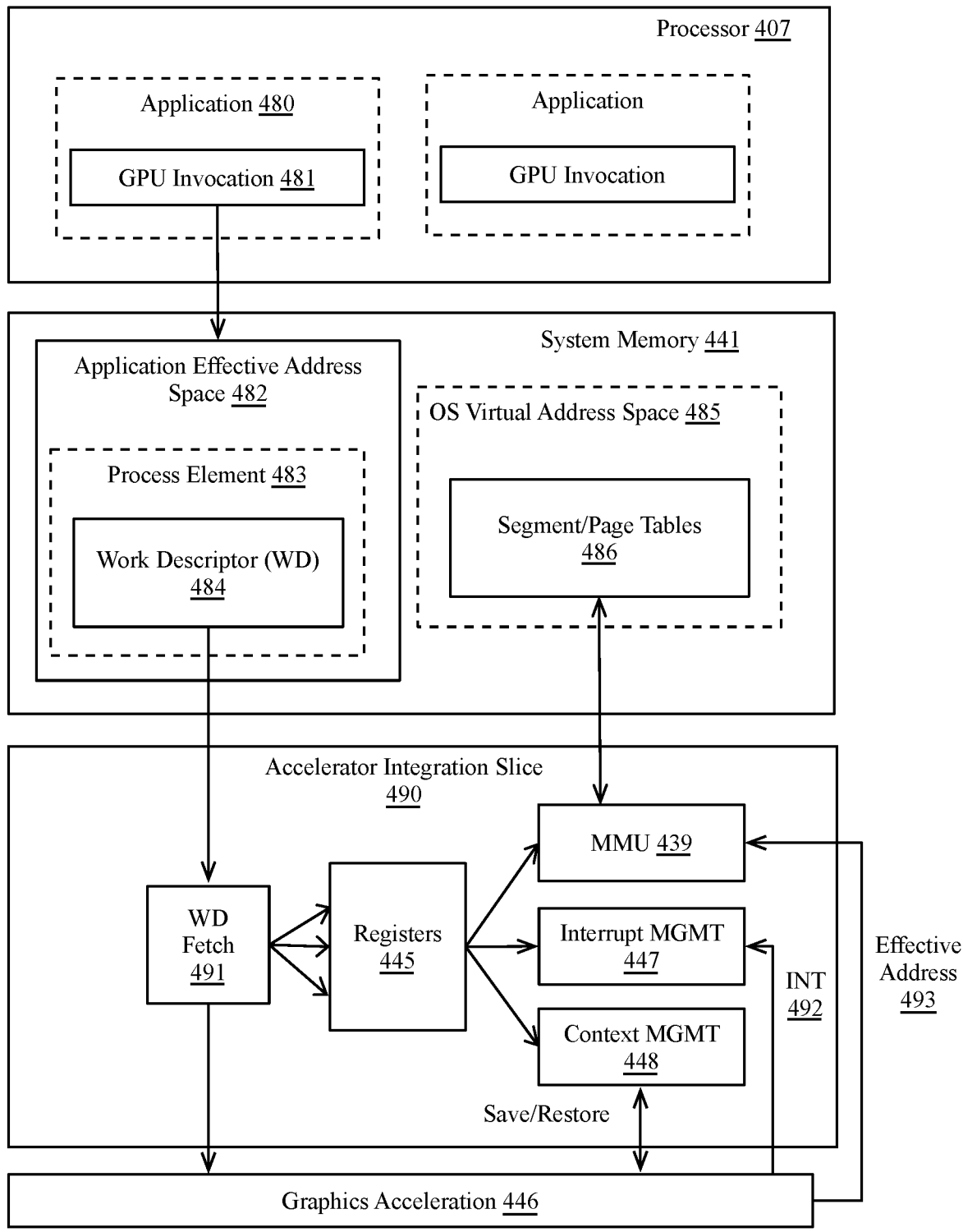

FIG. 4D illustrates an exemplary accelerator integration slice 490. As used herein, a "slice" comprises a specified portion of the processing resources of the accelerator integration circuit 436. Application effective address space 482 within system memory 411 stores process elements 483. In one embodiment, the process elements 483 are stored in response to GPU invocations 481 from applications 480 executed on the processor 407. A process element 483 contains the process state for the corresponding application 480. A work descriptor (WD) 484 contained in the process element 483 can be a single job requested by an application or may contain a pointer to a queue of jobs. In the latter case, the WD 484 is a pointer to the job request queue in the application's address space 482.

The graphics acceleration module 446 and/or the individual graphics processing engines 431-432, N can be shared by all or a subset of the processes in the system. Embodiments of the invention include an infrastructure for setting up the process state and sending a WD 484 to a graphics acceleration module 446 to start a job in a virtualized environment.

In one implementation, the dedicated-process programming model is implementation-specific. In this model, a single process owns the graphics acceleration module 446 or an individual graphics processing engine 431. Because the graphics acceleration module 446 is owned by a single process, the hypervisor initializes the accelerator integration circuit 436 for the owning partition and the operating system initializes the accelerator integration circuit 436 for the owning process at the time when the graphics acceleration module 446 is assigned.

In operation, a WD fetch unit 491 in the accelerator integration slice 490 fetches the next WD 484 which includes an indication of the work to be done by one of the graphics processing engines of the graphics acceleration module 446. Data from the WD 484 may be stored in registers 445 and used by the MMU 439, interrupt management circuit 447 and/or context management circuit 448 as illustrated. For example, one embodiment of the MMU 439 includes segment/page walk circuitry for accessing segment/page tables 486 within the OS virtual address space 485. The interrupt management circuit 447 may process interrupt events 492 received from the graphics acceleration module 446. When performing graphics operations, an effective address 493 generated by a graphics processing engine 431-432, N is translated to a real address by the MMU 439.

In one embodiment, the same set of registers 445 are duplicated for each graphics processing engine 431-432, N and/or graphics acceleration module 446 and may be initialized by the hypervisor or operating system. Each of these duplicated registers may be included in an accelerator integration slice 490. Exemplary registers that may be initialized by the hypervisor are shown in Table 1.

TABLE 1

Hypervisor Initialized Registers

1 Slice Control Register
2 Real Address (RA) Scheduled Processes Area Pointer
3 Authority Mask Override Register
4 Interrupt Vector Table Entry Offset
5 Interrupt Vector Table Entry Limit
6 State Register
7 Logical Partition ID
8 Real address (RA) Hypervisor Accelerator Utilization Record Pointer
9 Storage Description Register Exemplary registers that may be initialized by the operating system are shown in Table 2.

TABLE 2

Operating System Initialized Registers

1 Process and Thread Identification
2 Effective Address (EA) Context Save/Restore Pointer
3 Virtual Address (VA) Accelerator Utilization Record Pointer
4 Virtual Address (VA) Storage Segment Table Pointer
5 Authority Mask
6 Work descriptor In one embodiment, each WD 484 is specific to a particular graphics acceleration module 446 and/or graphics processing engine 431-432, N. It contains all the information a graphics processing engine 431-432, N requires to do its work or it can be a pointer to a memory location where the application has set up a command queue of work to be completed.

Figure 4E:
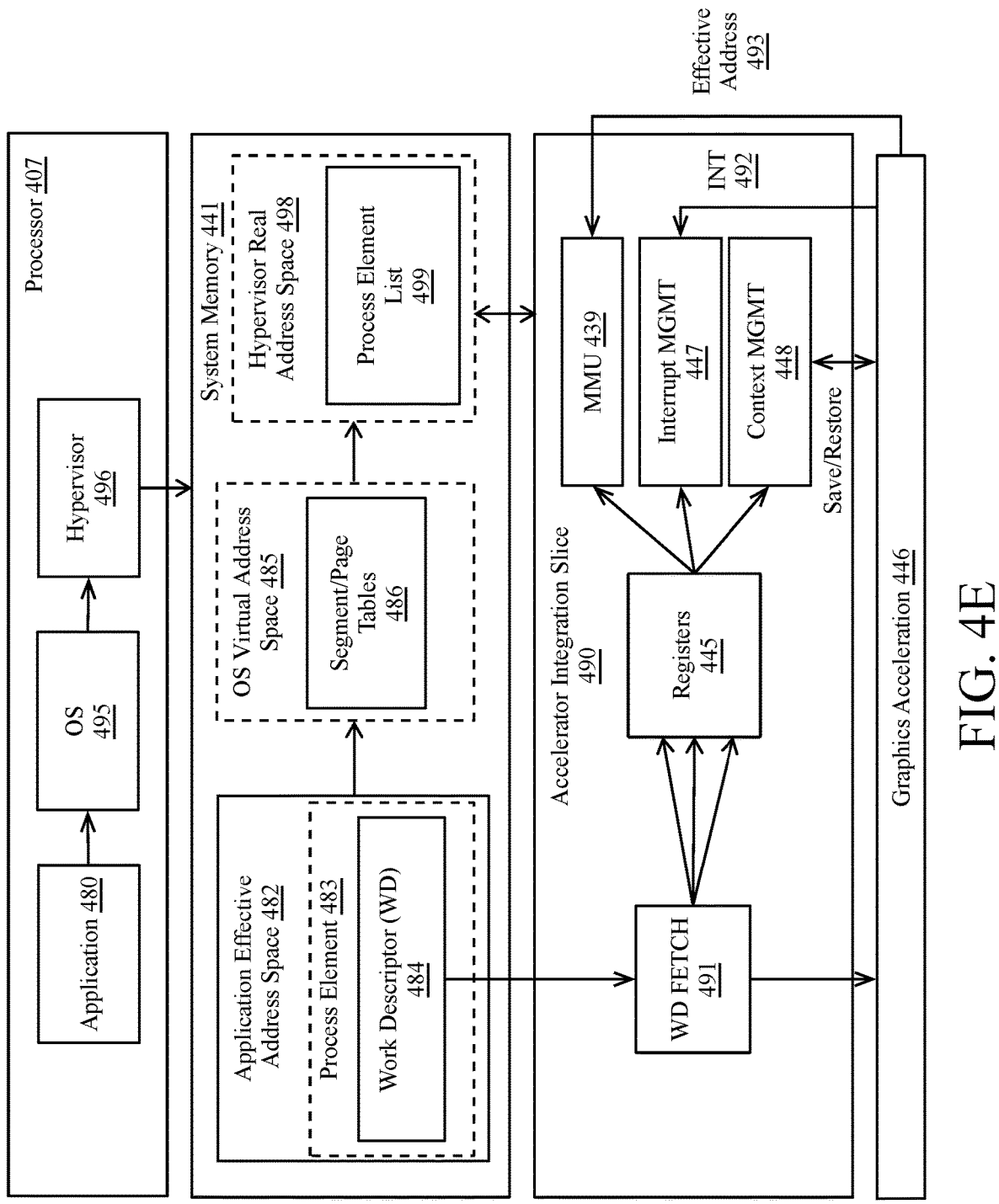

FIG. 4E illustrates additional details for one embodiment of a shared model. This embodiment includes a hypervisor real address space 498 in which a process element list 499 is stored. The hypervisor real address space 498 is accessible via a hypervisor 496 which virtualizes the graphics acceleration module engines for the operating system 495.

The shared programming models allow for all or a subset of processes from all or a subset of partitions in the system to use a graphics acceleration module 446. There are two programming models where the graphics acceleration module 446 is shared by multiple processes and partitions: time-sliced shared and graphics directed shared.

In this model, the system hypervisor 496 owns the graphics acceleration module 446 and makes its function available to all operating systems 495. For a graphics acceleration module 446 to support virtualization by the system hypervisor 496, the graphics acceleration module 446 may adhere to the following requirements: 1) An application's job request must be autonomous (that is, the state does not need to be maintained between jobs), or the graphics acceleration module 446 must provide a context save and restore mechanism. 2) An application's job request is guaranteed by the graphics acceleration module 446 to complete in a specified amount of time, including any translation faults, or the graphics acceleration module 446 provides the ability to preempt the processing of the job. 3) The graphics acceleration module 446 must be guaranteed fairness between processes when operating in the directed shared programming model.

In one embodiment, for the shared model, the application 480 is required to make an operating system 495 system call with a graphics acceleration module 446 type, a work descriptor (WD), an authority mask register (AMR) value, and a context save/restore area pointer (CSRP). The graphics acceleration module 446 type describes the targeted acceleration function for the system call. The graphics acceleration module 446 type may be a system-specific value. The WD is formatted specifically for the graphics acceleration module 446 and can be in the form of a graphics acceleration module 446 command, an effective address pointer to a user-defined structure, an effective address pointer to a queue of commands, or any other data structure to describe the work to be done by the graphics acceleration module 446. In one embodiment, the AMR value is the AMR state to use for the current process. The value passed to the operating system is similar to an application setting the AMR. If the accelerator integration circuit 436 and graphics acceleration module 446 implementations do not support a User Authority Mask Override Register (UAMOR), the operating system may apply the current UAMOR value to the AMR value before passing the AMR in the hypervisor call. The hypervisor 496 may optionally apply the current Authority Mask Override Register (AMOR) value before placing the AMR into the process element 483. In one embodiment, the CSRP is one of the registers 445 containing the effective address of an area in the application's address space 482 for the graphics acceleration module 446 to save and restore the context state. This pointer is optional if no state is required to be saved between jobs or when a job is preempted. The context save/restore area may be pinned system memory.

Upon receiving the system call, the operating system 495 may verify that the application 480 has registered and been given the authority to use the graphics acceleration module 446. The operating system 495 then calls the hypervisor 496 with the information shown in Table 3.

TABLE 3

OS to Hypervisor Call Parameters

1 A work descriptor (WD)
2 An Authority Mask Register (AMR) value (potentially masked).
3 An effective address (EA) Context Save/Restore Area Pointer (CSRP)
4 A process ID (PID) and optional thread ID (TID)
5 A virtual address (VA) accelerator utilization record pointer (AURP)
6 The virtual address of the storage segment table pointer (SSTP)
7 A logical interrupt service number (LISN)

Upon receiving the hypervisor call, the hypervisor 496 verifies that the operating system 495 has registered and been given the authority to use the graphics acceleration module 446. The hypervisor 496 then puts the process element 483 into the process element linked list for the corresponding graphics acceleration module 446 type. The process element may include the information shown in Table 4.

TABLE 4

Process Element Information

1 A work descriptor (WD)
2 An Authority Mask Register (AMR) value (potentially masked).
3 An effective address (EA) Context Save/Restore Area Pointer (CSRP)
4 A process ID (PID) and optional thread ID (TID)
5 A virtual address (VA) accelerator utilization record pointer (AURP)
6 The virtual address of the storage segment table pointer (SSTP)

TABLE 4-continued

Process Element Information

7  A logical interrupt service number (LISN)
8  Interrupt vector table, derived from the hypervisor call parameters.
9  A state register (SR) value
10 A logical partition ID (LPID)
11 A real address (RA) hypervisor accelerator utilization record pointer
12 The Storage Descriptor Register (SDR)

In one embodiment, the hypervisor initializes a plurality of accelerator integration slice 490 registers 445.

Figure 4F:
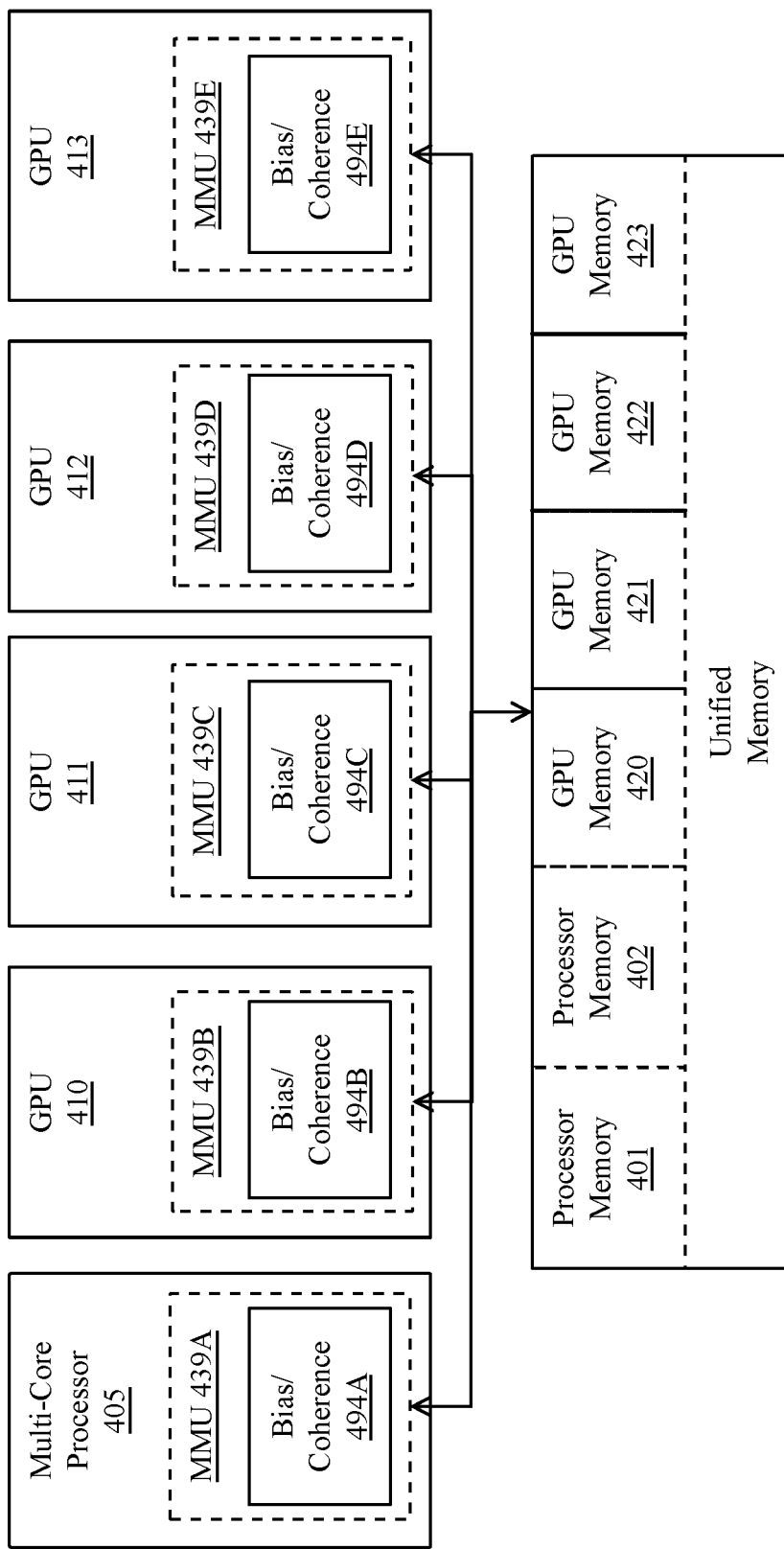

As illustrated in FIG. 4F, one embodiment of the invention employs a unified memory addressable via a common virtual memory address space used to access the physical processor memories 401-402 and GPU memories 420-423. In this implementation, operations executed on the GPUs 410-413 utilize the same virtual/effective memory address space to access the processors memories 401-402 and vice versa, thereby simplifying programmability. In one embodiment, a first portion of the virtual/effective address space is allocated to the processor memory 401, a second portion to the second processor memory 402, a third portion to the GPU memory 420, and so on. The entire virtual/effective memory space (sometimes referred to as the effective address space) is thereby distributed across each of the processor memories 401-402 and GPU memories 420-423, allowing any processor or GPU to access any physical memory with a virtual address mapped to that memory.

In one embodiment, bias/coherence management circuitry 494A-494E within one or more of the MMUs 439A-439E ensures cache coherence between the caches of the host processors (e.g., 405) and the GPUs 410-413 and implements biasing techniques indicating the physical memories in which certain types of data should be stored. While multiple instances of bias/coherence management circuitry 494A-494E are illustrated in FIG. 4F, the bias/coherence circuitry may be implemented within the MMU of one or more host processors 405 and/or within the accelerator integration circuit 436.

One embodiment allows GPU-attached memory 420-423 to be mapped as part of system memory, and accessed using shared virtual memory (SVM) technology, but without suffering the typical performance drawbacks associated with full system cache coherence. The ability to GPU-attached memory 420-423 to be accessed as system memory without onerous cache coherence overhead provides a beneficial operating environment for GPU offload. This arrangement allows the host processor 405 software to setup operands and access computation results, without the overhead of tradition I/O DMA data copies. Such traditional copies involve driver calls, interrupts and memory mapped I/O (MMIO) accesses that are all inefficient relative to simple memory accesses. At the same time, the ability to access GPU attached memory 420-423 without cache coherence overheads can be critical to the execution time of an offloaded computation. In cases with substantial streaming write memory traffic, for example, cache coherence overhead can significantly reduce the effective write bandwidth seen by a GPU 410-413. The efficiency of operand setup, the efficiency of results access, and the efficiency of GPU computation all play a role in determining the effectiveness of GPU offload.

In one implementation, the selection of between GPU bias and host processor bias is driven by a bias tracker data structure. A bias table may be used, for example, which may be a page-granular structure (i.e., controlled at the granularity of a memory page) that includes 1 or 2 bits per GPU-attached memory page. The bias table may be implemented in a stolen memory range of one or more GPU-attached memories 420-423, with or without a bias cache in the GPU 410-413 (e.g., to cache frequently/recently used entries of the bias table). Alternatively, the entire bias table may be maintained within the GPU.

In one implementation, the bias table entry associated with each access to the GPU-attached memory 420-423 is accessed prior the actual access to the GPU memory, causing the following operations. First, local requests from the GPU 410-413 that find their page in GPU bias are forwarded directly to a corresponding GPU memory 420-423. Local requests from the GPU that find their page in host bias are forwarded to the processor 405 (e.g., over a high-speed link as discussed above). In one embodiment, requests from the processor 405 that find the requested page in host processor bias complete the request like a normal memory read. Alternatively, requests directed to a GPU-biased page may be forwarded to the GPU 410-413. The GPU may then transition the page to a host processor bias if it is not currently using the page.

The bias state of a page can be changed either by a software-based mechanism, a hardware-assisted software-based mechanism, or, for a limited set of cases, a purely hardware-based mechanism.

One mechanism for changing the bias state employs an API call (e.g. OpenCL), which, in turn, calls the GPU's device driver which, in turn, sends a message (or enqueues a command descriptor) to the GPU directing it to change the bias state and, for some transitions, perform a cache flushing operation in the host. The cache flushing operation is required for a transition from host processor 405 bias to GPU bias, but is not required for the opposite transition.

In one embodiment, cache coherency is maintained by temporarily rendering GPU-biased pages uncacheable by the host processor 405. To access these pages, the processor 405 may request access from the GPU 410 which may or may not grant access right away, depending on the implementation. Thus, to reduce communication between the processor 405 and GPU 410 it is beneficial to ensure that GPU-biased pages are those which are required by the GPU but not the host processor 405 and vice versa.

Graphics Processing Pipeline

Figure 5:
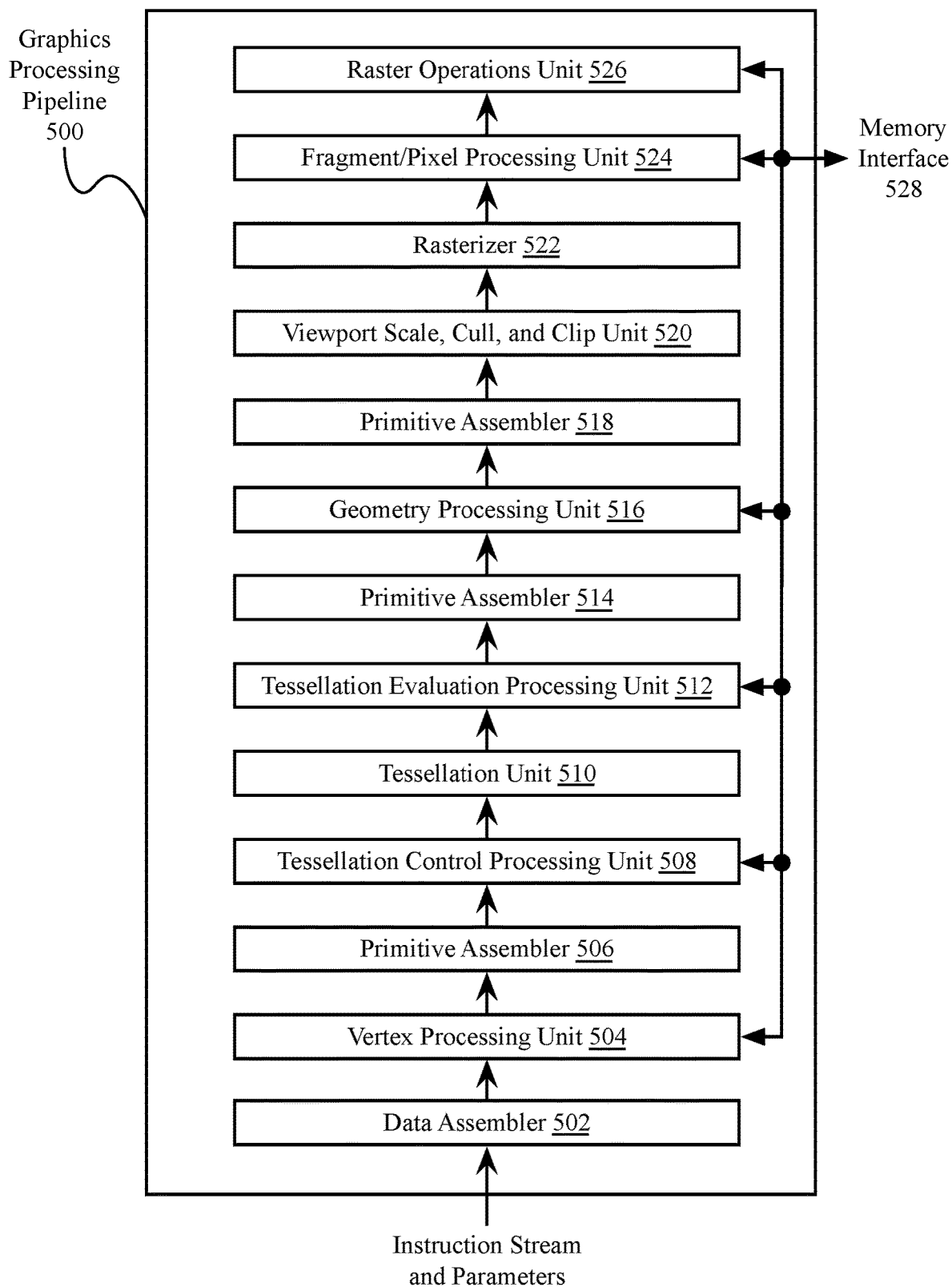
FIG. 5 is a conceptual diagram of a graphics processing pipeline, according to an embodiment.
Figure 7:
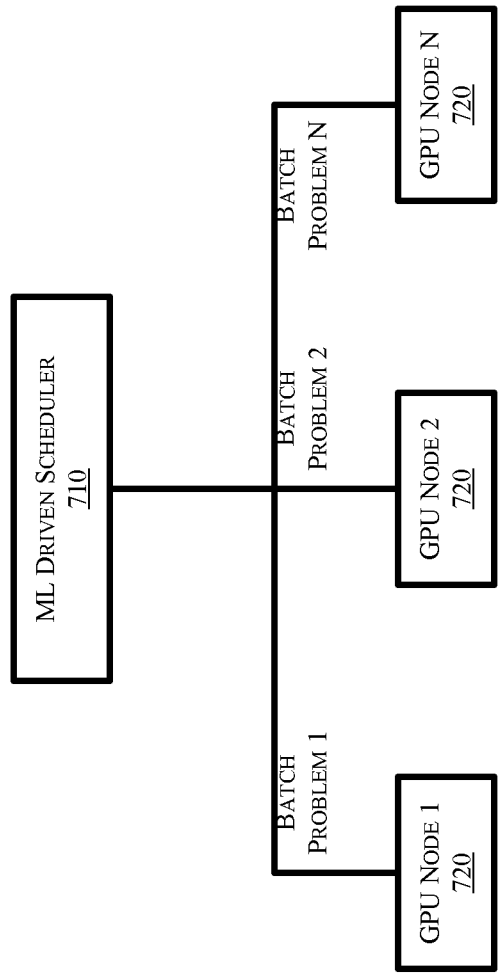
FIGS. 6-7 illustrate exemplary architectures and operations in techniques in accordance with embodiments.
Figure 6:
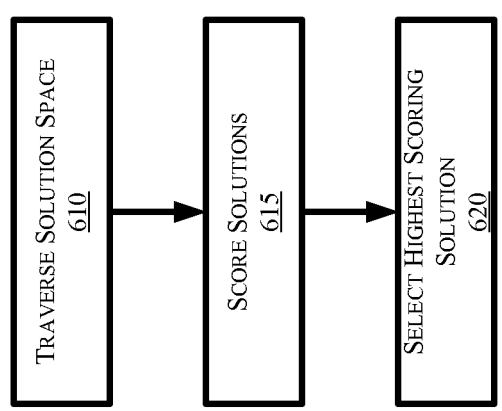

FIG. 5 illustrates a graphics processing pipeline 500, according to an embodiment. In one embodiment a graphics processor can implement the illustrated graphics processing pipeline 500. The graphics processor can be included within the parallel processing subsystems as described herein, such as the parallel processor 200 of FIG. 2, which, in one embodiment, is a variant of the parallel processor(s) 112 of FIG. 1. The various parallel processing systems can implement the graphics processing pipeline 500 via one or more instances of the parallel processing unit (e.g., parallel processing unit 202 of FIG. 2) as described herein. For example, a shader unit (e.g., graphics multiprocessor 234 of FIG. 3) may be configured to perform the functions of one or more of a vertex processing unit 504, a tessellation control processing unit 508, a tessellation evaluation processing unit 512, a geometry processing unit 516, and a fragment/pixel processing unit 524. The functions of data assembler 502, primitive assemblers 506, 514, 518, tessellation unit 510, rasterizer 522, and raster operations unit 526 may also be performed by other processing engines within a processing cluster (e.g., processing cluster 214 of FIG. 3) and a corresponding partition unit (e.g., partition unit 220A-220N of FIG. 2). The graphics processing pipeline 500 may also be implemented using dedicated processing units for one or more functions. In one embodiment, one or more portions of the graphics processing pipeline 500 can be performed by parallel processing logic within a general purpose processor (e.g., CPU). In one embodiment, one or more portions of the graphics processing pipeline 500 can access on-chip memory (e.g., parallel processor memory 222 as in FIG. 2A) via a memory interface 528, which may be an instance of the memory interface 218 of FIG. 2A.

In one embodiment the data assembler 502 is a processing unit that collects vertex data for surfaces and primitives. The data assembler 502 then outputs the vertex data, including the vertex attributes, to the vertex processing unit 504. The vertex processing unit 504 is a programmable execution unit that executes vertex shader programs, lighting and transforming vertex data as specified by the vertex shader programs. The vertex processing unit 504 reads data that is stored in cache, local or system memory for use in processing the vertex data and may be programmed to transform the vertex data from an object-based coordinate representation to a world space coordinate space or a normalized device coordinate space.

A first instance of a primitive assembler 506 receives vertex attributes from the vertex processing unit 504. The primitive assembler 506 readings stored vertex attributes as needed and constructs graphics primitives for processing by tessellation control processing unit 508. The graphics primitives include triangles, line segments, points, patches, and so forth, as supported by various graphics processing application programming interfaces (APIs).

The tessellation control processing unit 508 treats the input vertices as control points for a geometric patch. The control points are transformed from an input representation from the patch (e.g., the patch's bases) to a representation that is suitable for use in surface evaluation by the tessellation evaluation processing unit 512. The tessellation control processing unit 508 can also compute tessellation factors for edges of geometric patches. A tessellation factor applies to a single edge and quantifies a view-dependent level of detail associated with the edge. A tessellation unit 510 is configured to receive the tessellation factors for edges of a patch and to tessellate the patch into multiple geometric primitives such as line, triangle, or quadrilateral primitives, which are transmitted to a tessellation evaluation processing unit 512. The tessellation evaluation processing unit 512 operates on parameterized coordinates of the subdivided patch to generate a surface representation and vertex attributes for each vertex associated with the geometric primitives.

A second instance of a primitive assembler 514 receives vertex attributes from the tessellation evaluation processing unit 512, reading stored vertex attributes as needed, and constructs graphics primitives for processing by the geometry processing unit 516. The geometry processing unit 516 is a programmable execution unit that executes geometry shader programs to transform graphics primitives received from primitive assembler 514 as specified by the geometry shader programs. In one embodiment the geometry processing unit 516 is programmed to subdivide the graphics primitives into one or more new graphics primitives and calculate parameters used to rasterize the new graphics primitives.

In some embodiments the geometry processing unit 516 can add or delete elements in the geometry stream. The geometry processing unit 516 outputs the parameters and vertices specifying new graphics primitives to primitive assembler 518. The primitive assembler 518 receives the parameters and vertices from the geometry processing unit 516 and constructs graphics primitives for processing by a viewport scale, cull, and clip unit 520. The geometry processing unit 516 reads data that is stored in parallel processor memory or system memory for use in processing the geometry data. The viewport scale, cull, and clip unit 520 performs clipping, culling, and viewport scaling and outputs processed graphics primitives to a rasterizer 522.

The rasterizer 522 can perform depth culling and other depth-based optimizations. The rasterizer 522 also performs scan conversion on the new graphics primitives to generate fragments and output those fragments and associated coverage data to the fragment/pixel processing unit 524. The fragment/pixel processing unit 524 is a programmable execution unit that is configured to execute fragment shader programs or pixel shader programs. The fragment/pixel processing unit 524 transforming fragments or pixels received from rasterizer 522, as specified by the fragment or pixel shader programs. For example, the fragment/pixel processing unit 524 may be programmed to perform operations included but not limited to texture mapping, shading, blending, texture correction and perspective correction to produce shaded fragments or pixels that are output to a raster operations unit 526. The fragment/pixel processing unit 524 can read data that is stored in either the parallel processor memory or the system memory for use when processing the fragment data. Fragment or pixel shader programs may be configured to shade at sample, pixel, tile, or other granularities depending on the sampling rate configured for the processing units.

The raster operations unit 526 is a processing unit that performs raster operations including, but not limited to stencil, z test, blending, and the like, and outputs pixel data as processed graphics data to be stored in graphics memory (e.g., parallel processor memory 222 as in FIG. 2A, and/or system memory 104 as in FIG. 1), to be displayed on the one or more display device(s) 110 or for further processing by one of the one or more processor(s) 102 or parallel processor(s) 112. In some embodiments the raster operations unit 526 is configured to compress z or color data that is written to memory and decompress z or color data that is read from memory.

Many modern graphics processing units (GPUs) and use synchronous, wide buses to carry texture data, color data, and SIMD instructions' execution data, and transcode data. These buses can travel very long distance on-die, in the range of 2000 um, from a source to a destination, e.g., by utilizing upper layer of metal interconnect layers and intermediate flop-based repeaters. This on-die data transport consumes significant amount of application power for a given workload.

In some examples, when scheduling a DL network execution on a compute engine (CE), a rule-based algorithm may be implemented to traverse the entire solution-space (operation 610), score the different solutions (operation 615), and choose the highest scoring solution (operation 620). A solution defines tile sizes in the CE scratchpad memory and the system cache, traversal order, buffering levels, data type and other parameters.

In some examples scoring may be based on heuristics that may be incorrect because the system model may be inadequate to capture a complicated system with many interacting variables acts (e.g., busses, DMA, processing, etc.). To address this and other issues, a DL network may be implemented to study how the system behaves and choose a configuration for different layers (e.g., convolution, FC, GEMM, etc.) under various conditions (e.g., batching, several CVEs working together, etc.).

In some examples, task scheduling for a graphics processing unit (GPU) cluster is difficult due to a tradeoff between the number of nodes to use and an effective batch size that increases with the number of nodes. Increasing the batch size interferes with convergence of the learning process for the task scheduler. To compensate for this a scheduler may implement an optimal workload schedule for a GPU cluster to execute several tasks together based on machine learning processing of historical data.

In some examples, deep learning (DL) networks may use large, multi-dimensional inputs (e.g., input feature maps (IFMs) and filter weights) and outputs which can be traversed following various traversal strategies. For example, one strategy may take advantage of input-reuse, while another strategy may take advantage of weights-reuse. In some contexts, these traversal strategies are referred to as "scheduling policies."

In some examples, a scheduler component 710 determines a DL traversal strategy which is conveyed to a dispatcher component, which then dispatches the data and traversal strategy to a DL execution agent on a GPU node 720. In one example a traversal strategy for a 3D object divided into 3D tiles in which each tile is a 3D cube which is read/written from/to memory according to the numbers indicated in the diagram.

Machine Learning Overview

A machine learning algorithm is an algorithm that can learn based on a set of data. Embodiments of machine learning algorithms can be designed to model high-level abstractions within a data set. For example, image recognition algorithms can be used to determine which of several categories to which a given input belong; regression algorithms can output a numerical value given an input; and pattern recognition algorithms can be used to generate translated text or perform text to speech and/or speech recognition.

An exemplary type of machine learning algorithm is a neural network. There are many types of neural networks; a simple type of neural network is a feedforward network. A feedforward network may be implemented as an acyclic graph in which the nodes are arranged in layers. Typically, a feedforward network topology includes an input layer and an output layer that are separated by at least one hidden layer. The hidden layer transforms input received by the input layer into a representation that is useful for generating output in the output layer. The network nodes are fully connected via edges to the nodes in adjacent layers, but there are no edges between nodes within each layer. Data received at the nodes of an input layer of a feedforward network are propagated (i.e., "fed forward") to the nodes of the output layer via an activation function that calculates the states of the nodes of each successive layer in the network based on coefficients ("weights") respectively associated with each of the edges connecting the layers. Depending on the specific model being represented by the algorithm being executed, the output from the neural network algorithm can take various forms.

Before a machine learning algorithm can be used to model a particular problem, the algorithm is trained using a training data set. Training a neural network involves selecting a network topology, using a set of training data representing a problem being modeled by the network, and adjusting the weights until the network model performs with a minimal error for all instances of the training data set. For example, during a supervised learning training process for a neural network, the output produced by the network in response to the input representing an instance in a training data set is compared to the "correct" labeled output for that instance, an error signal representing the difference between the output and the labeled output is calculated, and the weights associated with the connections are adjusted to minimize that error as the error signal is backward propagated through the layers of the network. The network is considered "trained" when the errors for each of the outputs generated from the instances of the training data set are minimized.

The accuracy of a machine learning algorithm can be affected significantly by the quality of the data set used to train the algorithm. The training process can be computationally intensive and may require a significant amount of time on a conventional general-purpose processor. Accordingly, parallel processing hardware is used to train many types of machine learning algorithms. This is particularly useful for optimizing the training of neural networks, as the computations performed in adjusting the coefficients in neural networks lend themselves naturally to parallel implementations. Specifically, many machine learning algorithms and software applications have been adapted to make use of the parallel processing hardware within general-purpose graphics processing devices.

Figure 8:
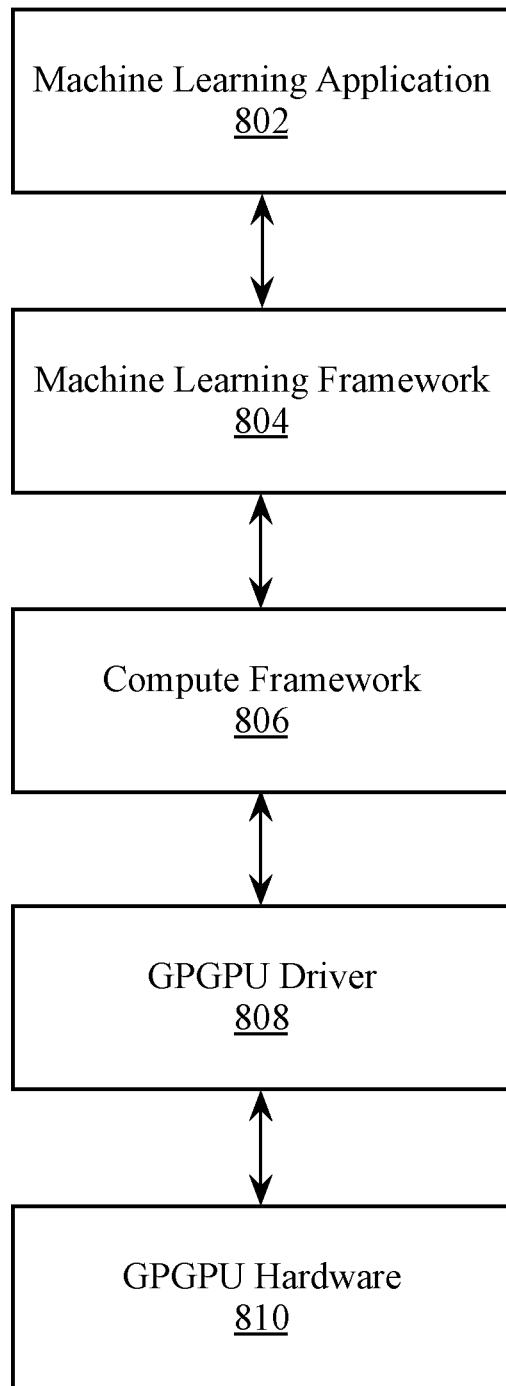
FIG. 8 illustrates a machine learning software stack, according to an embodiment.

FIG. 8 is a generalized diagram of a machine learning software stack 800. A machine learning application 802 can be configured to train a neural network using a training dataset or to use a trained deep neural network to implement machine intelligence. The machine learning application 802 can include training and inference functionality for a neural network and/or specialized software that can be used to train a neural network before deployment. The machine learning application 802 can implement any type of machine intelligence including but not limited to image recognition, mapping and localization, autonomous navigation, speech synthesis, medical imaging, or language translation.

Hardware acceleration for the machine learning application 802 can be enabled via a machine learning framework 804. The machine learning framework 804 can provide a library of machine learning primitives. Machine learning primitives are basic operations that are commonly performed by machine learning algorithms. Without the machine learning framework 804, developers of machine learning algorithms would be required to create and optimize the main computational logic associated with the machine learning algorithm, then re-optimize the computational logic as new parallel processors are developed. Instead, the machine learning application can be configured to perform the necessary computations using the primitives provided by the machine learning framework 804. Exemplary primitives include tensor convolutions, activation functions, and pooling, which are computational operations that are performed while training a convolutional neural network (CNN). The machine learning framework 804 can also provide primitives to implement basic linear algebra subprograms performed by many machine-learning algorithms, such as matrix and vector operations.

The machine learning framework 804 can process input data received from the machine learning application 802 and generate the appropriate input to a compute framework 806. The compute framework 806 can abstract the underlying instructions provided to the GPGPU driver 808 to enable the machine learning framework 804 to take advantage of hardware acceleration via the GPGPU hardware 810 without requiring the machine learning framework 804 to have intimate knowledge of the architecture of the GPGPU hardware 810. Additionally, the compute framework 806 can enable hardware acceleration for the machine learning framework 804 across a variety of types and generations of the GPGPU hardware 810.

GPGPU Machine Learning Acceleration

Figure 9:
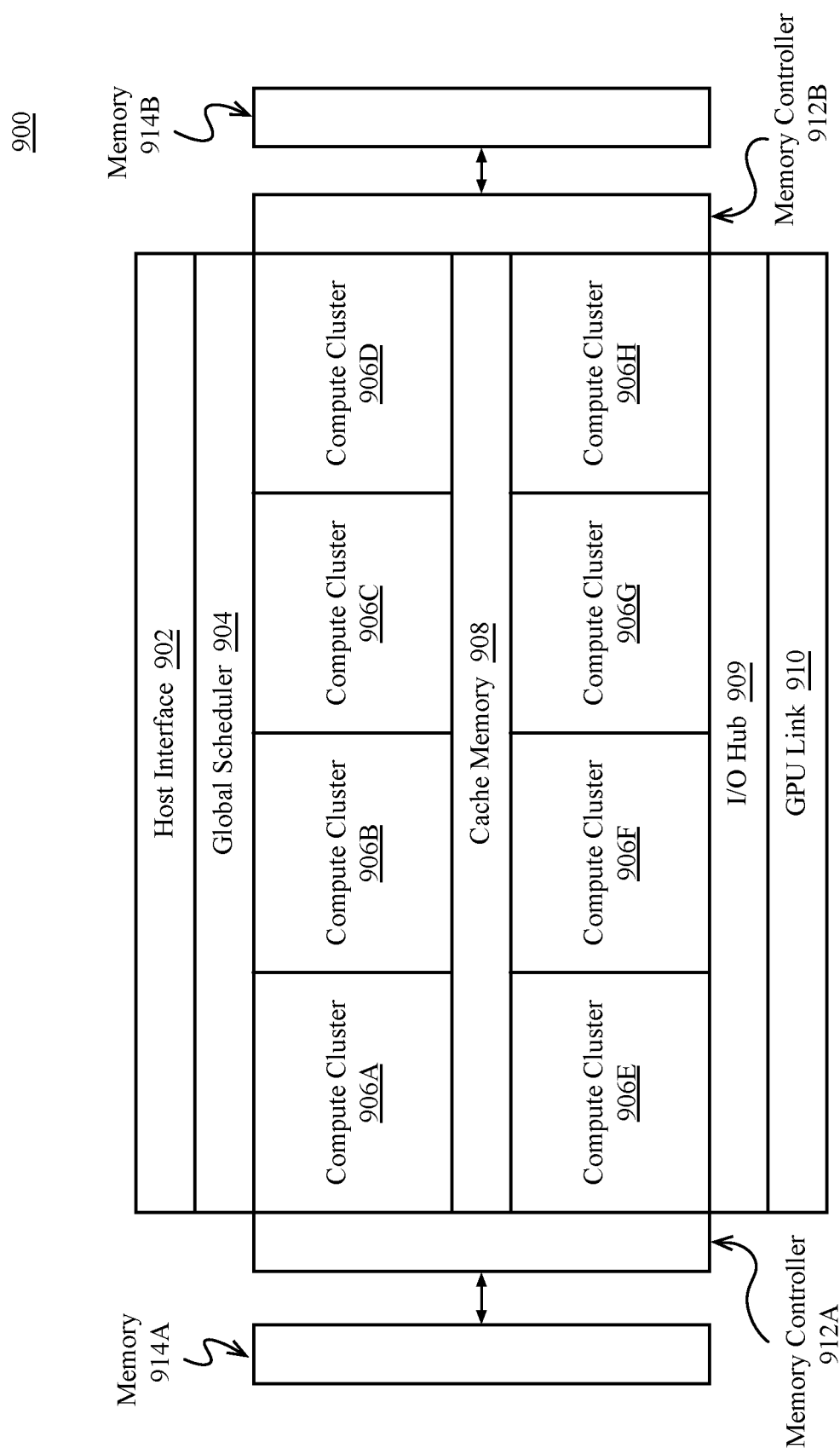
FIG. 9 illustrates a highly-parallel general-purpose graphics processing unit, according to an embodiment.

FIG. 9 illustrates a highly-parallel general-purpose graphics processing unit 900, according to an embodiment. In one embodiment the general-purpose processing unit (GPGPU) 900 can be configured to be particularly efficient in processing the type of computational workloads associated with training deep neural networks. Additionally, the GPGPU 900 can be linked directly to other instances of the GPGPU to create a multi-GPU cluster to improve training speed for particularly deep neural networks.

The GPGPU 900 includes a host interface 902 to enable a connection with a host processor. In one embodiment the host interface 902 is a PCI Express interface. However, the host interface can also be a vendor specific communications interface or communications fabric. The GPGPU 900 receives commands from the host processor and uses a global scheduler 904 to distribute execution threads associated with those commands to a set of compute clusters 906A-H. The compute clusters 906A-H share a cache memory 908. The cache memory 908 can serve as a higher-level cache for cache memories within the compute clusters 906A-H.

The GPGPU 900 includes memory 914A-B coupled with the compute clusters 906A-H via a set of memory controllers 912A-B. In various embodiments, the memory 914A-B can include various types of memory devices including dynamic random access memory (DRAM) or graphics random access memory, such as synchronous graphics random access memory (SGRAM), including graphics double data rate (GDDR) memory. In one embodiment, the memory units 224A-N may also include 3D stacked memory, including but not limited to high bandwidth memory (HBM).

In one embodiment each compute cluster 906A-H includes a set of graphics multiprocessors, such as the graphics multiprocessor 234 of FIG. 2D. The graphics multiprocessors of the compute cluster multiple types of integer and floating point logic units that can perform computational operations at a range of precisions including suited for machine learning computations. For example and in one embodiment at least a subset of the floating point units in each of the compute clusters 906A-H can be configured to perform 16-bit or 32-bit floating point operations, while a different subset of the floating point units can be configured to perform 64-bit floating point operations.

Multiple instances of the GPGPU 900 can be configured to operate as a compute cluster. The communication mechanism used by the compute cluster for synchronization and data exchange varies across embodiments. In one embodiment the multiple instances of the GPGPU 900 communicate over the host interface 902. In one embodiment the GPGPU 900 includes an I/O hub 909 that couples the GPGPU 900 with a GPU link 910 that enables a direct connection to other instances of the GPGPU. In one embodiment the GPU link 910 is coupled to a dedicated GPU-to-GPU bridge that enables communication and synchronization between multiple instances of the GPGPU 900. In one embodiment the GPU link 910 couples with a high speed interconnect to transmit and receive data to other GPGPUs or parallel processors. In one embodiment the multiple instances of the GPGPU 900 are located in separate data processing systems and communicate via a network device that is accessible via the host interface 902. In one embodiment the GPU link 910 can be configured to enable a connection to a host processor in addition to or as an alternative to the host interface 902.

While the illustrated configuration of the GPGPU 900 can be configured to train neural networks, one embodiment provides alternate configuration of the GPGPU 900 that can be configured for deployment within a high performance or low power inferencing platform. In an inferencing configuration the GPGPU 900 includes fewer of the compute clusters 906A-H relative to the training configuration. Additionally memory technology associated with the memory 914A-B may differ between inferencing and training configurations. In one embodiment the inferencing configuration of the GPGPU 900 can support inferencing specific instructions. For example, an inferencing configuration can provide support for one or more 8-bit integer dot product instructions, which are commonly used during inferencing operations for deployed neural networks.

Figure 10:
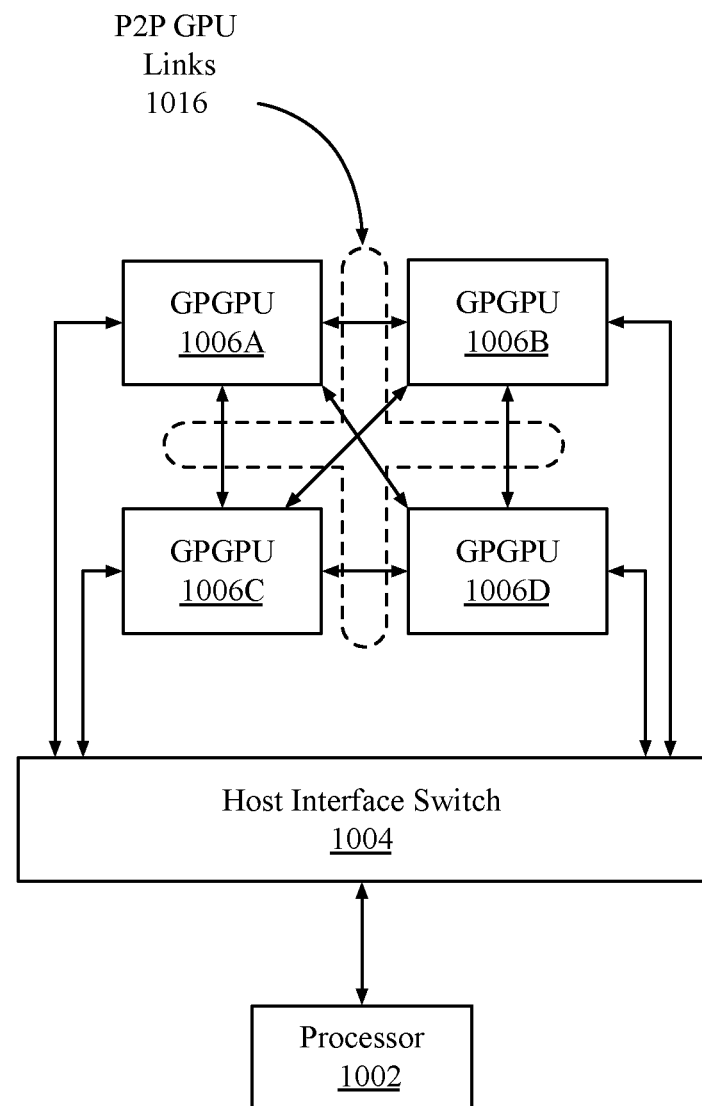
FIG. 10 illustrates a multi-GPU computing system, according to an embodiment.

FIG. 10 illustrates a multi-GPU computing system 1000, according to an embodiment. The multi-GPU computing system 1000 can include a processor 1002 coupled to multiple GPGPUs 1006A-D via a host interface switch 1004. The host interface switch 1004, in one embodiment, is a PCI express switch device that couples the processor 1002 to a PCI express bus over which the processor 1002 can communicate with the set of GPGPUs 1006A-D. Each of the multiple GPGPUs 1006A-D can be an instance of the GPGPU 900 of FIG. 9. The GPGPUs 1006A-D can interconnect via a set of high-speed point to point GPU to GPU links 1016. The high-speed GPU to GPU links can connect to each of the GPGPUs 1006A-D via a dedicated GPU link, such as the GPU link 910 as in FIG. 9. The P2P GPU links 1016 enable direct communication between each of the GPGPUs 1006A-D without requiring communication over the host interface bus to which the processor 1002 is connected. With GPU-to-GPU traffic directed to the P2P GPU links, the host interface bus remains available for system memory access or to communicate with other instances of the multi-GPU computing system 1000, for example, via one or more network devices. While in the illustrated embodiment the GPGPUs 1006A-D connect to the processor 1002 via the host interface switch 1004, in one embodiment the processor 1002 includes direct support for the P2P GPU links 1016 and can connect directly to the GPGPUs 1006A-D.

Machine Learning Neural Network Implementations

The computing architecture provided by embodiments described herein can be configured to perform the types of parallel processing that is particularly suited for training and deploying neural networks for machine learning. A neural network can be generalized as a network of functions having a graph relationship. As is well-known in the art, there are a variety of types of neural network implementations used in machine learning. One exemplary type of neural network is the feedforward network, as previously described.

A second exemplary type of neural network is the Convolutional Neural Network (CNN). A CNN is a specialized feedforward neural network for processing data having a known, grid-like topology, such as image data. Accordingly, CNNs are commonly used for compute vision and image recognition applications, but they also may be used for other types of pattern recognition such as speech and language processing. The nodes in the CNN input layer are organized into a set of "filters" (feature detectors inspired by the receptive fields found in the retina), and the output of each set of filters is propagated to nodes in successive layers of the network. The computations for a CNN include applying the convolution mathematical operation to each filter to produce the output of that filter. Convolution is a specialized kind of mathematical operation performed by two functions to produce a third function that is a modified version of one of the two original functions. In convolutional network terminology, the first function to the convolution can be referred to as the input, while the second function can be referred to as the convolution kernel. The output may be referred to as the feature map. For example, the input to a convolution layer can be a multidimensional array of data that defines the various color components of an input image. The convolution kernel can be a multidimensional array of parameters, where the parameters are adapted by the training process for the neural network.

Recurrent neural networks (RNNs) are a family of feedforward neural networks that include feedback connections between layers. RNNs enable modeling of sequential data by sharing parameter data across different parts of the neural network. The architecture for a RNN includes cycles. The cycles represent the influence of a present value of a variable on its own value at a future time, as at least a portion of the output data from the RNN is used as feedback for processing subsequent input in a sequence. This feature makes RNNs particularly useful for language processing due to the variable nature in which language data can be composed.

The figures described below present exemplary feedforward, CNN, and RNN networks, as well as describe a general process for respectively training and deploying each of those types of networks. It will be understood that these descriptions are exemplary and non-limiting as to any specific embodiment described herein and the concepts illustrated can be applied generally to deep neural networks and machine learning techniques in general.

The exemplary neural networks described above can be used to perform deep learning. Deep learning is machine learning using deep neural networks. The deep neural networks used in deep learning are artificial neural networks composed of multiple hidden layers, as opposed to shallow neural networks that include only a single hidden layer. Deeper neural networks are generally more computationally intensive to train. However, the additional hidden layers of the network enable multistep pattern recognition that results in reduced output error relative to shallow machine learning techniques.

Deep neural networks used in deep learning typically include a front-end network to perform feature recognition coupled to a back-end network which represents a mathematical model that can perform operations (e.g., object classification, speech recognition, etc.) based on the feature representation provided to the model. Deep learning enables machine learning to be performed without requiring hand crafted feature engineering to be performed for the model. Instead, deep neural networks can learn features based on statistical structure or correlation within the input data. The learned features can be provided to a mathematical model that can map detected features to an output. The mathematical model used by the network is generally specialized for the specific task to be performed, and different models will be used to perform different task.

Once the neural network is structured, a learning model can be applied to the network to train the network to perform specific tasks. The learning model describes how to adjust the weights within the model to reduce the output error of the network. Backpropagation of errors is a common method used to train neural networks. An input vector is presented to the network for processing. The output of the network is compared to the desired output using a loss function and an error value is calculated for each of the neurons in the output layer. The error values are then propagated backwards until each neuron has an associated error value which roughly represents its contribution to the original output. The network can then learn from those errors using an algorithm, such as the stochastic gradient descent algorithm, to update the weights of the of the neural network.

Figure 11A:
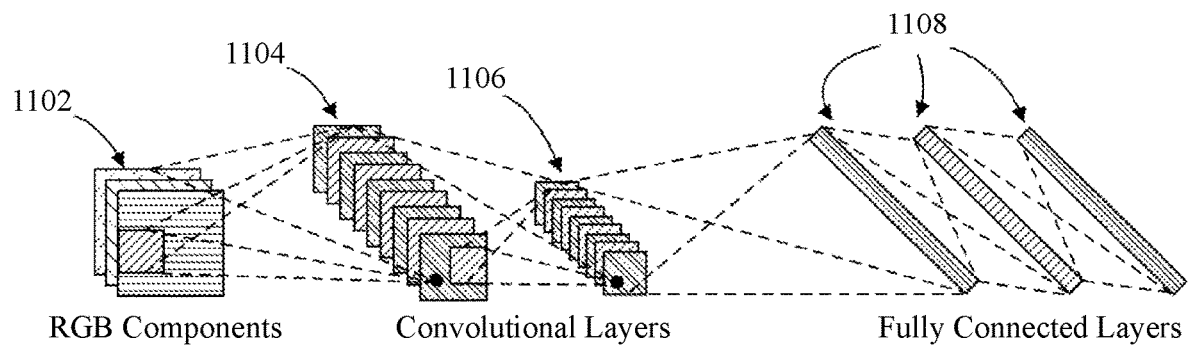
FIG. 11A-B illustrate layers of exemplary deep neural networks.
Figure 11B:
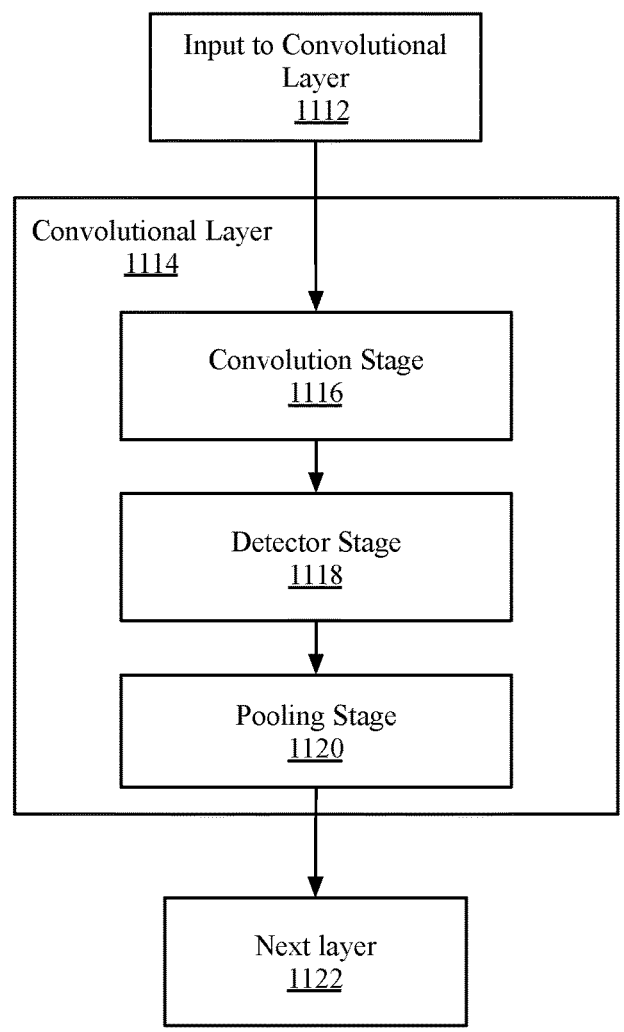

FIG. 11A-B illustrate an exemplary convolutional neural network. FIG. 11A illustrates various layers within a CNN. As shown in FIG. 11A, an exemplary CNN used to model image processing can receive input 1102 describing the red, green, and blue (RGB) components of an input image. The input 1102 can be processed by multiple convolutional layers (e.g., convolutional layer 1104, convolutional layer 1106). The output from the multiple convolutional layers may optionally be processed by a set of fully connected layers 1108. Neurons in a fully connected layer have full connections to all activations in the previous layer, as previously described for a feedforward network. The output from the fully connected layers 1108 can be used to generate an output result from the network. The activations within the fully connected layers 1108 can be computed using matrix multiplication instead of convolution. Not all CNN implementations are make use of fully connected layers 1108. For example, in some implementations the convolutional layer 1106 can generate output for the CNN.

The convolutional layers are sparsely connected, which differs from traditional neural network configuration found in the fully connected layers 1108. Traditional neural network layers are fully connected, such that every output unit interacts with every input unit. However, the convolutional layers are sparsely connected because the output of the convolution of a field is input (instead of the respective state value of each of the nodes in the field) to the nodes of the subsequent layer, as illustrated. The kernels associated with the convolutional layers perform convolution operations, the output of which is sent to the next layer. The dimensionality reduction performed within the convolutional layers is one aspect that enables the CNN to scale to process large images.

FIG. 11B illustrates exemplary computation stages within a convolutional layer of a CNN. Input to a convolutional layer 1112 of a CNN can be processed in three stages of a convolutional layer 1114. The three stages can include a convolution stage 1116, a detector stage 1118, and a pooling stage 1120. The convolutional layer 1114 can then output data to a successive convolutional layer. The final convolutional layer of the network can generate output feature map data or provide input to a fully connected layer, for example, to generate a classification value for the input to the CNN.

In the convolution stage 1116 performs several convolutions in parallel to produce a set of linear activations. The convolution stage 1116 can include an affine transformation, which is any transformation that can be specified as a linear transformation plus a translation. Affine transformations include rotations, translations, scaling, and combinations of these transformations. The convolution stage computes the output of functions (e.g., neurons) that are connected to specific regions in the input, which can be determined as the local region associated with the neuron. The neurons compute a dot product between the weights of the neurons and the region in the local input to which the neurons are connected. The output from the convolution stage 1116 defines a set of linear activations that are processed by successive stages of the convolutional layer 1114.

The linear activations can be processed by a detector stage 1118. In the detector stage 1118, each linear activation is processed by a non-linear activation function. The non-linear activation function increases the nonlinear properties of the overall network without affecting the receptive fields of the convolution layer. Several types of non-linear activation functions may be used. One particular type is the rectified linear unit (ReLU), which uses an activation function defined as $f=\max(0,x)$, such that the activation is thresholded at zero.

The pooling stage 1120 uses a pooling function that replaces the output of the convolutional layer 1106 with a summary statistic of the nearby outputs. The pooling function can be used to introduce translation invariance into the neural network, such that small translations to the input do not change the pooled outputs. Invariance to local translation can be useful in scenarios where the presence of a feature in the input data is more important than the precise location of the feature. Various types of pooling functions can be used during the pooling stage 1120, including max pooling, average pooling, and l2-norm pooling. Additionally, some CNN implementations do not include a pooling stage. Instead, such implementations substitute and additional convolution stage having an increased stride relative to previous convolution stages.

The output from the convolutional layer 1114 can then be processed by the next layer 1122. The next layer 1122 can be an additional convolutional layer or one of the fully connected layers 1108. For example, the first convolutional layer 1104 of FIG. 11A can output to the second convolutional layer 1106, while the second convolutional layer can output to a first layer of the fully connected layers 1108.

Figure 12:
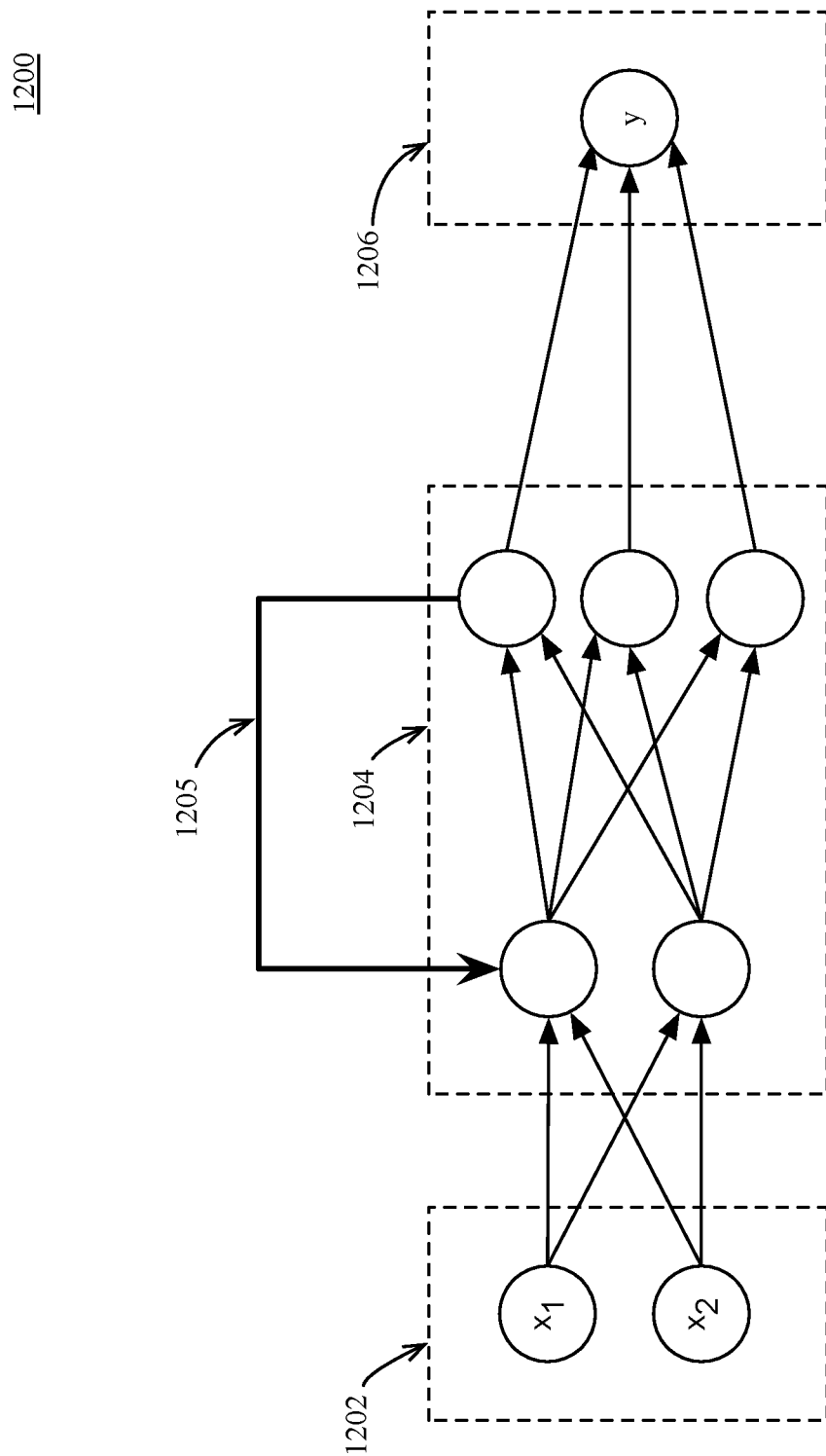
FIG. 12 illustrates an exemplary recurrent neural network.

FIG. 12 illustrates an exemplary recurrent neural network 1200. In a recurrent neural network (RNN), the previous state of the network influences the output of the current state of the network. RNNs can be built in a variety of ways using a variety of functions. The use of RNNs generally revolves around using mathematical models to predict the future based on a prior sequence of inputs. For example, an RNN may be used to perform statistical language modeling to predict an upcoming word given a previous sequence of words. The illustrated RNN 1200 can be described has having an input layer 1202 that receives an input vector, hidden layers 1204 to implement a recurrent function, a feedback mechanism 1205 to enable a 'memory' of previous states, and an output layer 1206 to output a result. The RNN 1200 operates based on time-steps. The state of the RNN at a given time step is influenced based on the previous time step via the feedback mechanism 1205. For a given time step, the state of the hidden layers 1204 is defined by the previous state and the input at the current time step. An initial input ($x_1$) at a first time step can be processed by the hidden layer 1204. A second input ($x_2$) can be processed by the hidden layer 1204 using state information that is determined during the processing of the initial input ($x_1$). A given state can be computed as $s_t=f(Ux_t+Ws_{t-1})$, where U and W are parameter matrices. The function $f$ is generally a non-linearity, such as the hyperbolic tangent function (Tanh) or a variant of the rectifier function $f(x)=\max(0,x)$. However, the specific mathematical function used in the hidden layers 1204 can vary depending on the specific implementation details of the RNN 1200.

In addition to the basic CNN and RNN networks described, variations on those networks may be enabled. One example RNN variant is the long short term memory (LSTM) RNN. LSTM RNNs are capable of learning long-term dependencies that may be necessary for processing longer sequences of language. A variant on the CNN is a convolutional deep belief network, which has a structure similar to a CNN and is trained in a manner similar to a deep belief network. A deep belief network (DBN) is a generative neural network that is composed of multiple layers of stochastic (random) variables. DBNs can be trained layer-by-layer using greedy unsupervised learning. The learned weights of the DBN can then be used to provide pre-train neural networks by determining an optimal initial set of weights for the neural network.

Figure 13:
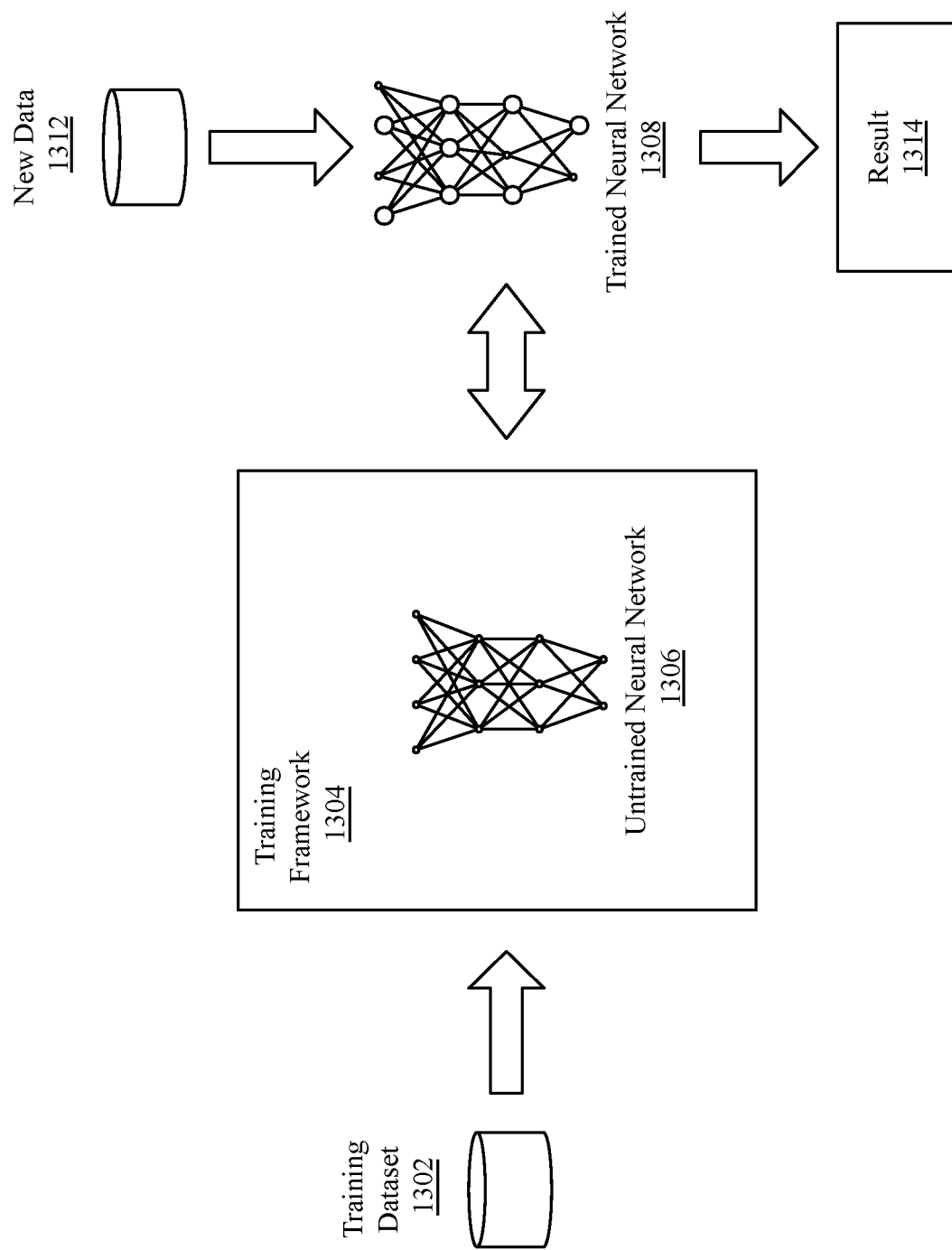
FIG. 13 illustrates training and deployment of a deep neural network.

FIG. 13 illustrates training and deployment of a deep neural network. Once a given network has been structured for a task the neural network is trained using a training dataset 1302. Various training frameworks have been developed to enable hardware acceleration of the training process. For example, the machine learning framework 804 of FIG. 8 may be configured as a training framework 1304. The training framework 1304 can hook into an untrained neural network 1306 and enable the untrained neural net to be trained using the parallel processing resources described herein to generate a trained neural net 1308.

To start the training process the initial weights may be chosen randomly or by pre-training using a deep belief network. The training cycle then be performed in either a supervised or unsupervised manner.

Supervised learning is a learning method in which training is performed as a mediated operation, such as when the training dataset 1302 includes input paired with the desired output for the input, or where the training dataset includes input having known output and the output of the neural network is manually graded. The network processes the inputs and compares the resulting outputs against a set of expected or desired outputs. Errors are then propagated back through the system. The training framework 1304 can adjust to adjust the weights that control the untrained neural network 1306. The training framework 1304 can provide tools to monitor how well the untrained neural network 1306 is converging towards a model suitable to generating correct answers based on known input data. The training process occurs repeatedly as the weights of the network are adjusted to refine the output generated by the neural network. The training process can continue until the neural network reaches a statistically desired accuracy associated with a trained neural net 1308. The trained neural network 1308 can then be deployed to implement any number of machine learning operations.

Unsupervised learning is a learning method in which the network attempts to train itself using unlabeled data. Thus, for unsupervised learning the training dataset 1302 will include input data without any associated output data. The untrained neural network 1306 can learn groupings within the unlabeled input and can determine how individual inputs are related to the overall dataset. Unsupervised training can be used to generate a self-organizing map, which is a type of trained neural network 1307 capable of performing operations useful in reducing the dimensionality of data. Unsupervised training can also be used to perform anomaly detection, which allows the identification of data points in an input dataset that deviate from the normal patterns of the data.

Variations on supervised and unsupervised training may also be employed. Semi-supervised learning is a technique in which in the training dataset 1302 includes a mix of labeled and unlabeled data of the same distribution. Incremental learning is a variant of supervised learning in which input data is continuously used to further train the model. Incremental learning enables the trained neural network 1308 to adapt to the new data 1312 without forgetting the knowledge instilled within the network during initial training.

Whether supervised or unsupervised, the training process for particularly deep neural networks may be too computationally intensive for a single compute node. Instead of using a single compute node, a distributed network of computational nodes can be used to accelerate the training process.

Figure 14:
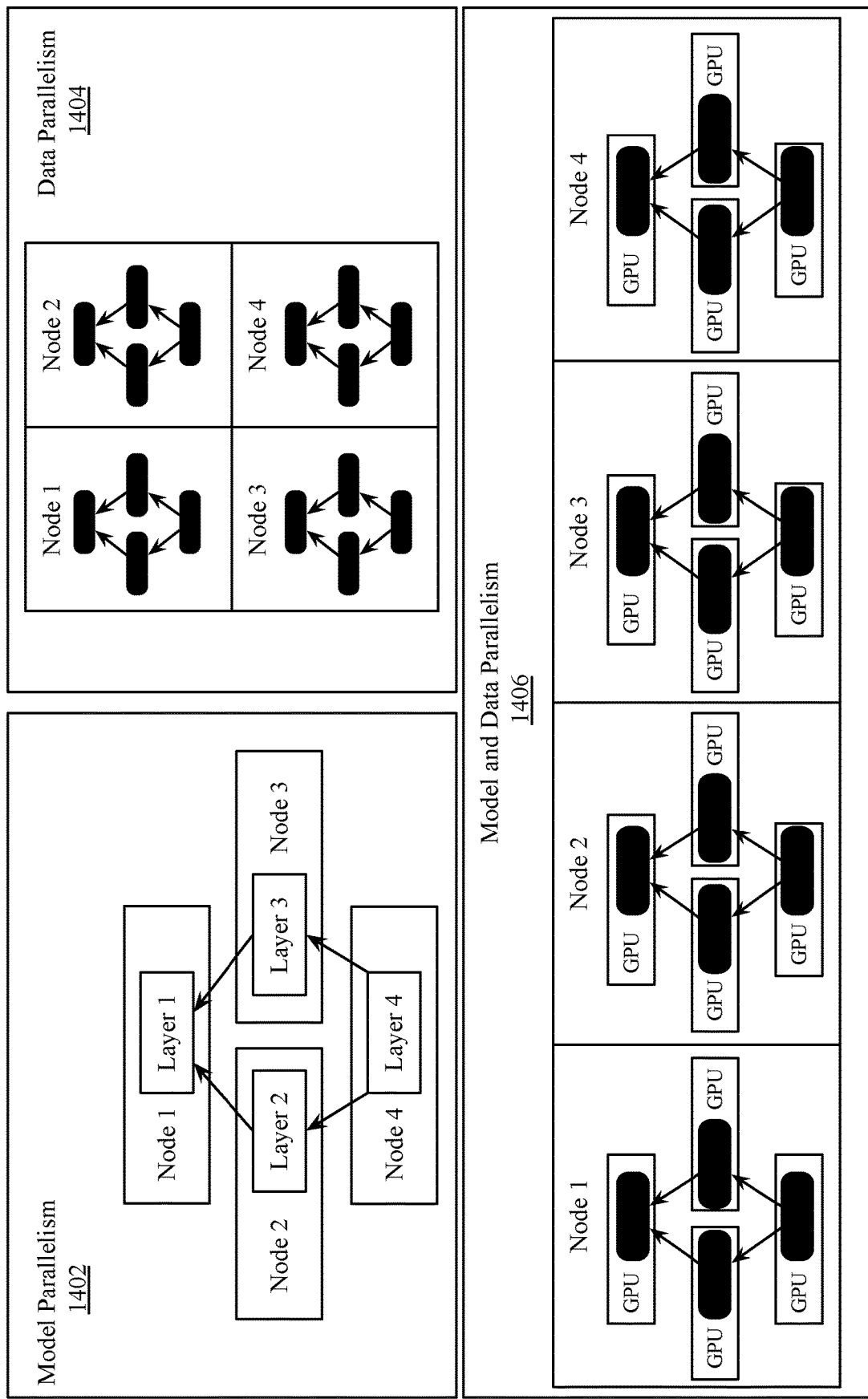
FIG. 14 is a block diagram illustrating distributed learning.

FIG. 14 is a block diagram illustrating distributed learning. Distributed learning is a training model that uses multiple distributed computing nodes to perform supervised or unsupervised training of a neural network. The distributed computational nodes can each include one or more host processors and one or more of the general-purpose processing nodes, such as the highly-parallel general-purpose graphics processing unit 900 as in FIG. 9. As illustrated, distributed learning can be performed model parallelism 1402, data parallelism 1404, or a combination of model and data parallelism 1404.

In model parallelism 1402, different computational nodes in a distributed system can perform training computations for different parts of a single network. For example, each layer of a neural network can be trained by a different processing node of the distributed system. The benefits of model parallelism include the ability to scale to particularly large models. Splitting the computations associated with different layers of the neural network enables the training of very large neural networks in which the weights of all layers would not fit into the memory of a single computational node. In some instances, model parallelism can be particularly useful in performing unsupervised training of large neural networks.

In data parallelism 1404, the different nodes of the distributed network have a complete instance of the model and each node receives a different portion of the data. The results from the different nodes are then combined. While different approaches to data parallelism are possible, data parallel training approaches all require a technique of combining results and synchronizing the model parameters between each node. Exemplary approaches to combining data include parameter averaging and update based data parallelism. Parameter averaging trains each node on a subset of the training data and sets the global parameters (e.g., weights, biases) to the average of the parameters from each node. Parameter averaging uses a central parameter server that maintains the parameter data. Update based data parallelism is similar to parameter averaging except that instead of transferring parameters from the nodes to the parameter server, the updates to the model are transferred. Additionally, update based data parallelism can be performed in a decentralized manner, where the updates are compressed and transferred between nodes.

Combined model and data parallelism 1406 can be implemented, for example, in a distributed system in which each computational node includes multiple GPUs. Each node can have a complete instance of the model with separate GPUs within each node are used to train different portions of the model.

Distributed training has increased overhead relative to training on a single machine. However, the parallel processors and GPGPUs described herein can each implement various techniques to reduce the overhead of distributed training, including techniques to enable high bandwidth GPU-to-GPU data transfer and accelerated remote data synchronization.

Exemplary Machine Learning Applications

Machine learning can be applied to solve a variety of technological problems, including but not limited to computer vision, autonomous driving and navigation, speech recognition, and language processing. Computer vision has traditionally been one of the most active research areas for machine learning applications. Applications of computer vision range from reproducing human visual abilities, such as recognizing faces, to creating new categories of visual abilities. For example, computer vision applications can be configured to recognize sound waves from the vibrations induced in objects visible in a video. Parallel processor accelerated machine learning enables computer vision applications to be trained using significantly larger training dataset than previously feasible and enables inferencing systems to be deployed using low power parallel processors.

Parallel processor accelerated machine learning has autonomous driving applications including lane and road sign recognition, obstacle avoidance, navigation, and driving control. Accelerated machine learning techniques can be used to train driving models based on datasets that define the appropriate responses to specific training input. The parallel processors described herein can enable rapid training of the increasingly complex neural networks used for autonomous driving solutions and enables the deployment of low power inferencing processors in a mobile platform suitable for integration into autonomous vehicles.

Parallel processor accelerated deep neural networks have enabled machine learning approaches to automatic speech recognition (ASR). ASR includes the creation of a function that computes the most probable linguistic sequence given an input acoustic sequence. Accelerated machine learning using deep neural networks have enabled the replacement of the hidden Markov models (HMMs) and Gaussian mixture models (GMMs) previously used for ASR.

Parallel processor accelerated machine learning can also be used to accelerate natural language processing. Automatic learning procedures can make use of statistical inference algorithms to produce models that are robust to erroneous or unfamiliar input. Exemplary natural language processor applications include automatic machine translation between human languages.

The parallel processing platforms used for machine learning can be divided into training platforms and deployment platforms. Training platforms are generally highly parallel and include optimizations to accelerate multi-GPU single node training and multi-node, multi-GPU training. Exemplary parallel processors suited for training include the highly-parallel general-purpose graphics processing unit 900 of FIG. 9 and the multi-GPU computing system 1000 of FIG. 10. On the contrary, deployed machine learning platforms generally include lower power parallel processors suitable for use in products such as cameras, autonomous robots, and autonomous vehicles.

Figure 15:
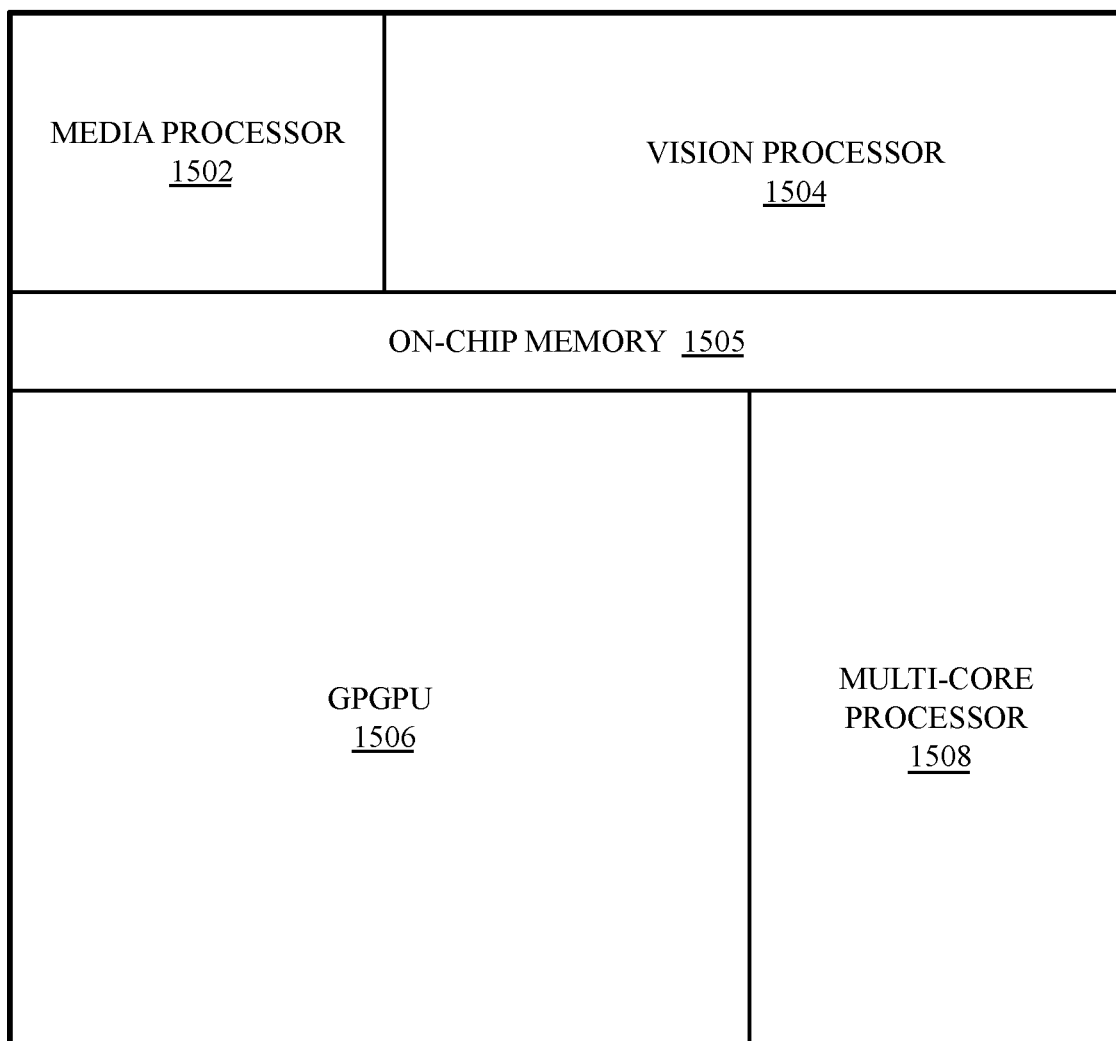
FIG. 15 illustrates an exemplary inferencing system on a chip (SOC) suitable for performing inferencing using a trained model.

FIG. 15 illustrates an exemplary inferencing system on a chip (SOC) 1500 suitable for performing inferencing using a trained model. The SOC 1500 can integrate processing components including a media processor 1502, a vision processor 1504, a GPGPU 1506 and a multi-core processor 1508. The SOC 1500 can additionally include an on-chip memory 1505 that can enable a shared on-chip data pool that is accessible by each of the processing components. The processing components can be optimized for low power operation to enable deployment to a variety of machine learning platforms, including autonomous vehicles and autonomous robots. For example, one implementation of the SOC 1500 can be used as a portion of the main control system for an autonomous vehicle. Where the SOC 1500 is configured for use in autonomous vehicles the SOC is designed and configured for compliance with the relevant functional safety standards of the deployment jurisdiction.

During operation, the media processor 1502 and vision processor 1504 can work in concert to accelerate computer vision operations. The media processor 1502 can enable low latency decode of multiple high-resolution (e.g., 4K, 8K) video streams. The decoded video streams can be written to a buffer in the on-chip memory 1505. The vision processor 1504 can then parse the decoded video and perform preliminary processing operations on the frames of the decoded video in preparation of processing the frames using a trained image recognition model. For example, the vision processor 1504 can accelerate convolution operations for a CNN that is used to perform image recognition on the high-resolution video data, while back end model computations are performed by the GPGPU 1506.

The multi-core processor 1508 can include control logic to assist with sequencing and synchronization of data transfers and shared memory operations performed by the media processor 1502 and the vision processor 1504. The multi-core processor 1508 can also function as an application processor to execute software applications that can make use of the inferencing compute capability of the GPGPU 1506. For example, at least a portion of the navigation and driving logic can be implemented in software executing on the multi-core processor 1508. Such software can directly issue computational workloads to the GPGPU 1506 or the computational workloads can be issued to the multi-core processor 1508, which can offload at least a portion of those operations to the GPGPU 1506.

The GPGPU 1506 can include compute clusters such as a low power configuration of the compute clusters 906A-906H within the highly-parallel general-purpose graphics processing unit 900. The compute clusters within the GPGPU 1506 can support instruction that are specifically optimized to perform inferencing computations on a trained neural network. For example, the GPGPU 1506 can support instructions to perform low precision computations such as 8-bit and 4-bit integer vector operations.

Additional Exemplary Graphics Processing System

Details of the embodiments described above can be incorporated within graphics processing systems and devices described below. The graphics processing system and devices of FIG. 21-29 illustrate alternative systems and graphics processing hardware that can implement any and all of the techniques described above.

Additional Exemplary Graphics Processing System Overview

Figure 16:
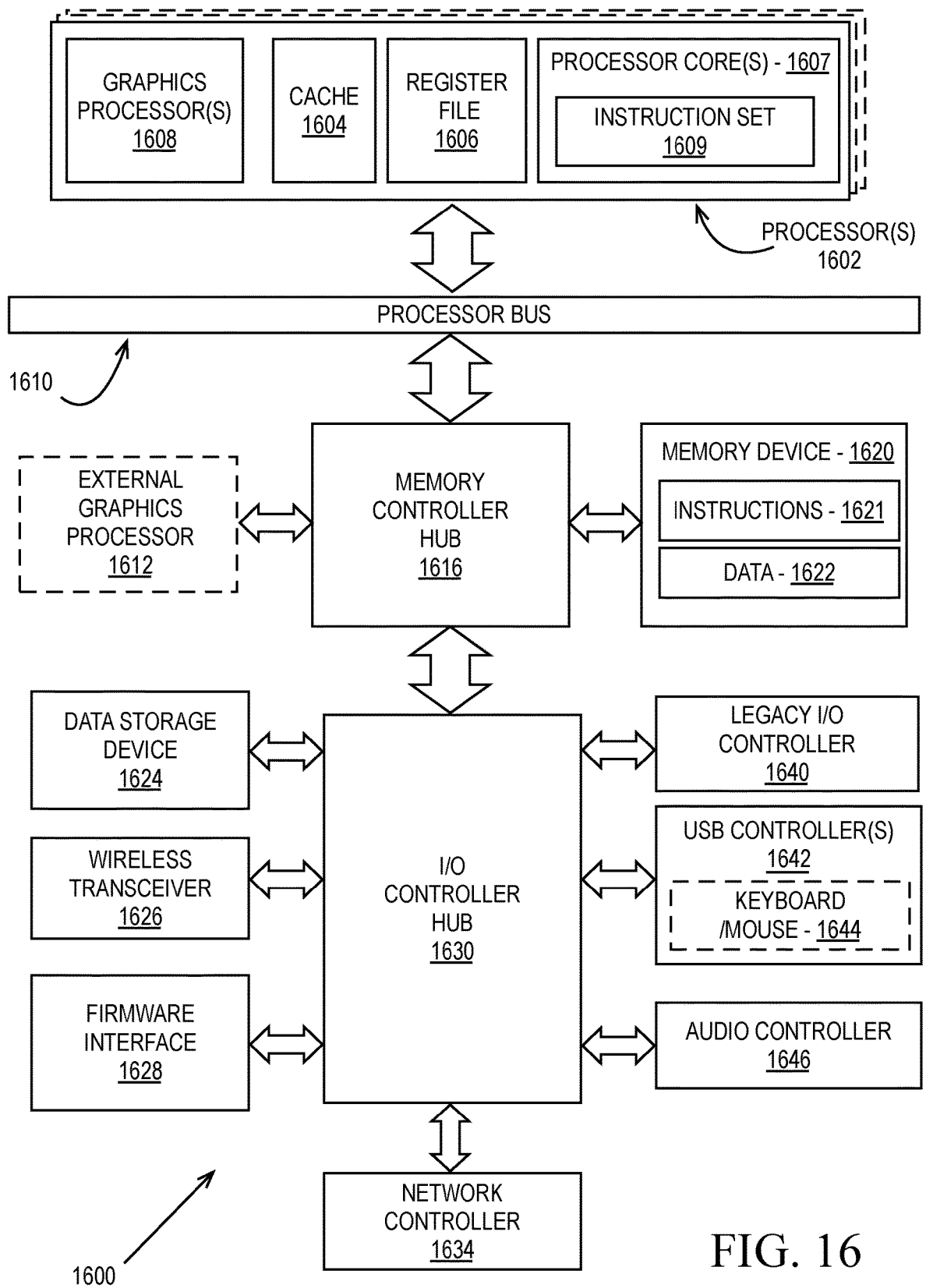
FIG. 16 is a block diagram of a processing system, according to an embodiment.

FIG. 16 is a block diagram of a processing system 1600, according to an embodiment. In various embodiments the system 1600 includes one or more processors 1602 and one or more graphics processors 1608, and may be a single processor desktop system, a multiprocessor workstation system, or a server system having a large number of processors 1602 or processor cores 1607. In one embodiment, the system 1600 is a processing platform incorporated within a system-on-a-chip (SoC) integrated circuit for use in mobile, handheld, or embedded devices.

An embodiment of system 1600 can include, or be incorporated within a server-based gaming platform, a game console, including a game and media console, a mobile gaming console, a handheld game console, or an online game console. In some embodiments system 1600 is a mobile phone, smart phone, tablet computing device or mobile Internet device. Data processing system 1600 can also include, couple with, or be integrated within a wearable device, such as a smart watch wearable device, smart eyewear device, augmented reality device, or virtual reality device. In some embodiments, data processing system 1600 is a television or set top box device having one or more processors 1602 and a graphical interface generated by one or more graphics processors 1608.

In some embodiments, the one or more processors 1602 each include one or more processor cores 1607 to process instructions which, when executed, perform operations for system and user software. In some embodiments, each of the one or more processor cores 1607 is configured to process a specific instruction set 1609. In some embodiments, instruction set 1609 may facilitate Complex Instruction Set Computing (CISC), Reduced Instruction Set Computing (RISC), or computing via a Very Long Instruction Word (VLIW). Multiple processor cores 1607 may each process a different instruction set 1609, which may include instructions to facilitate the emulation of other instruction sets. Processor core 1607 may also include other processing devices, such a Digital Signal Processor (DSP).

In some embodiments, the processor 1602 includes cache memory 1604. Depending on the architecture, the processor 1602 can have a single internal cache or multiple levels of internal cache. In some embodiments, the cache memory is shared among various components of the processor 1602. In some embodiments, the processor 1602 also uses an external cache (e.g., a Level-3 (L3) cache or Last Level Cache (LLC)) (not shown), which may be shared among processor cores 1607 using known cache coherency techniques. A register file 1606 is additionally included in processor 1602 which may include different types of registers for storing different types of data (e.g., integer registers, floating point registers, status registers, and an instruction pointer register). Some registers may be general-purpose registers, while other registers may be specific to the design of the processor 1602.

In some embodiments, processor 1602 is coupled with a processor bus 1610 to transmit communication signals such as address, data, or control signals between processor 1602 and other components in system 1600. In one embodiment the system 1600 uses an exemplary 'hub' system architecture, including a memory controller hub 1616 and an Input Output (I/O) controller hub 1630. A memory controller hub 1616 facilitates communication between a memory device and other components of system 1600, while an I/O Controller Hub (ICH) 1630 provides connections to I/O devices via a local I/O bus. In one embodiment, the logic of the memory controller hub 1616 is integrated within the processor.

Memory device 1620 can be a dynamic random access memory (DRAM) device, a static random access memory (SRAM) device, flash memory device, phase-change memory device, or some other memory device having suitable performance to serve as process memory. In one embodiment the memory device 1620 can operate as system memory for the system 1600, to store data 1622 and instructions 1621 for use when the one or more processors 1602 executes an application or process. Memory controller hub 1616 also couples with an optional external graphics processor 1612, which may communicate with the one or more graphics processors 1608 in processors 1602 to perform graphics and media operations.

In some embodiments, ICH 1630 enables peripherals to connect to memory device 1620 and processor 1602 via a high-speed I/O bus. The I/O peripherals include, but are not limited to, an audio controller 1646, a firmware interface 1628, a wireless transceiver 1626 (e.g., Wi-Fi, Bluetooth), a data storage device 1624 (e.g., hard disk drive, flash memory, etc.), and a legacy I/O controller 1640 for coupling legacy (e.g., Personal System 2 (PS/2)) devices to the system. One or more Universal Serial Bus (USB) controllers 1642 connect input devices, such as keyboard and mouse 1644 combinations. A network controller 1634 may also couple with ICH 1630. In some embodiments, a high-performance network controller (not shown) couples with processor bus 1610. It will be appreciated that the system 1600 shown is exemplary and not limiting, as other types of data processing systems that are differently configured may also be used. For example, the I/O controller hub 1630 may be integrated within the one or more processor 1602, or the memory controller hub 1616 and I/O controller hub 1630 may be integrated into a discreet external graphics processor, such as the external graphics processor 1612.

Figure 17:
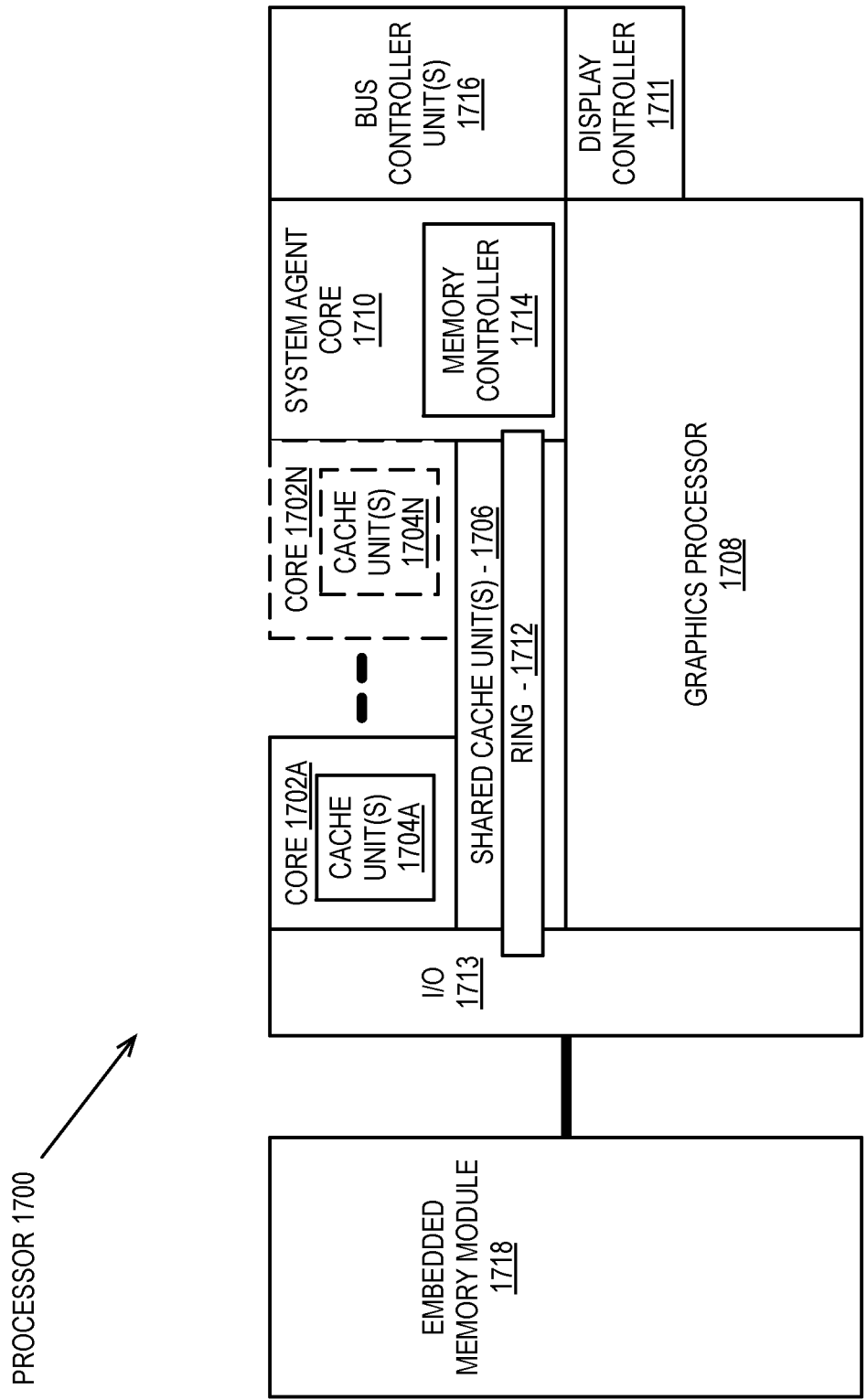
FIG. 17 is a block diagram of a processor according to an embodiment.

FIG. 17 is a block diagram of an embodiment of a processor 1700 having one or more processor cores 1702A-1702N, an integrated memory controller 1714, and an integrated graphics processor 1708. Those elements of FIG. 17 having the same reference numbers (or names) as the elements of any other figure herein can operate or function in any manner similar to that described elsewhere herein, but are not limited to such. Processor 1700 can include additional cores up to and including additional core 1702N represented by the dashed lined boxes. Each of processor cores 1702A-1702N includes one or more internal cache units 1704A-1704N. In some embodiments each processor core also has access to one or more shared cached units 1706.

The internal cache units 1704A-1704N and shared cache units 1706 represent a cache memory hierarchy within the processor 1700. The cache memory hierarchy may include at least one level of instruction and data cache within each processor core and one or more levels of shared mid-level cache, such as a Level 2 (L2), Level 3 (L3), Level 4 (L4), or other levels of cache, where the highest level of cache before external memory is classified as the LLC. In some embodiments, cache coherency logic maintains coherency between the various cache units 1706 and 1704A-1704N.

In some embodiments, processor 1700 may also include a set of one or more bus controller units 1716 and a system agent core 1710. The one or more bus controller units 1716 manage a set of peripheral buses, such as one or more Peripheral Component Interconnect buses (e.g., PCI, PCI Express). System agent core 1710 provides management functionality for the various processor components. In some embodiments, system agent core 1710 includes one or more integrated memory controllers 1714 to manage access to various external memory devices (not shown).

In some embodiments, one or more of the processor cores 1702A-1702N include support for simultaneous multi-threading. In such embodiment, the system agent core 1710 includes components for coordinating and operating processor cores 1702A-1702N during multi-threaded processing. System agent core 1710 may additionally include a power control unit (PCU), which includes logic and components to regulate the power state of processor cores 1702A-1702N and graphics processor 1708.

In some embodiments, processor 1700 additionally includes graphics processor 1708 to execute graphics processing operations. In some embodiments, the graphics processor 1708 couples with the set of shared cache units 1706, and the system agent core 1710, including the one or more integrated memory controllers 1714. In some embodiments, a display controller 1711 is coupled with the graphics processor 1708 to drive graphics processor output to one or more coupled displays. In some embodiments, display controller 1711 may be a separate module coupled with the graphics processor via at least one interconnect, or may be integrated within the graphics processor 1708 or system agent core 1710.

In some embodiments, a ring-based interconnect unit 1712 is used to couple the internal components of the processor 1700. However, an alternative interconnect unit may be used, such as a point-to-point interconnect, a switched interconnect, or other techniques, including techniques well known in the art. In some embodiments, graphics processor 1708 couples with the ring-based interconnect 1712 via an I/O link 1713.

The exemplary I/O link 1713 represents at least one of multiple varieties of I/O interconnects, including an on-package I/O interconnect which facilitates communication between various processor components and a high-performance embedded memory module 1718, such as an eDRAM module. In some embodiments, each of the processor cores 1702A-1702N and graphics processor 1708 use embedded memory modules 1718 as a shared Last Level Cache.

In some embodiments, processor cores 1702A-1702N are homogenous cores executing the same instruction set architecture. In another embodiment, processor cores 1702A-1702N are heterogeneous in terms of instruction set architecture (ISA), where one or more of processor cores 1702A-1702N execute a first instruction set, while at least one of the other cores executes a subset of the first instruction set or a different instruction set. In one embodiment processor cores 1702A-1702N are heterogeneous in terms of microarchitecture, where one or more cores having a relatively higher power consumption couple with one or more power cores having a lower power consumption. Additionally, processor 1700 can be implemented on one or more chips or as an SoC integrated circuit having the illustrated components, in addition to other components.

Figure 18:
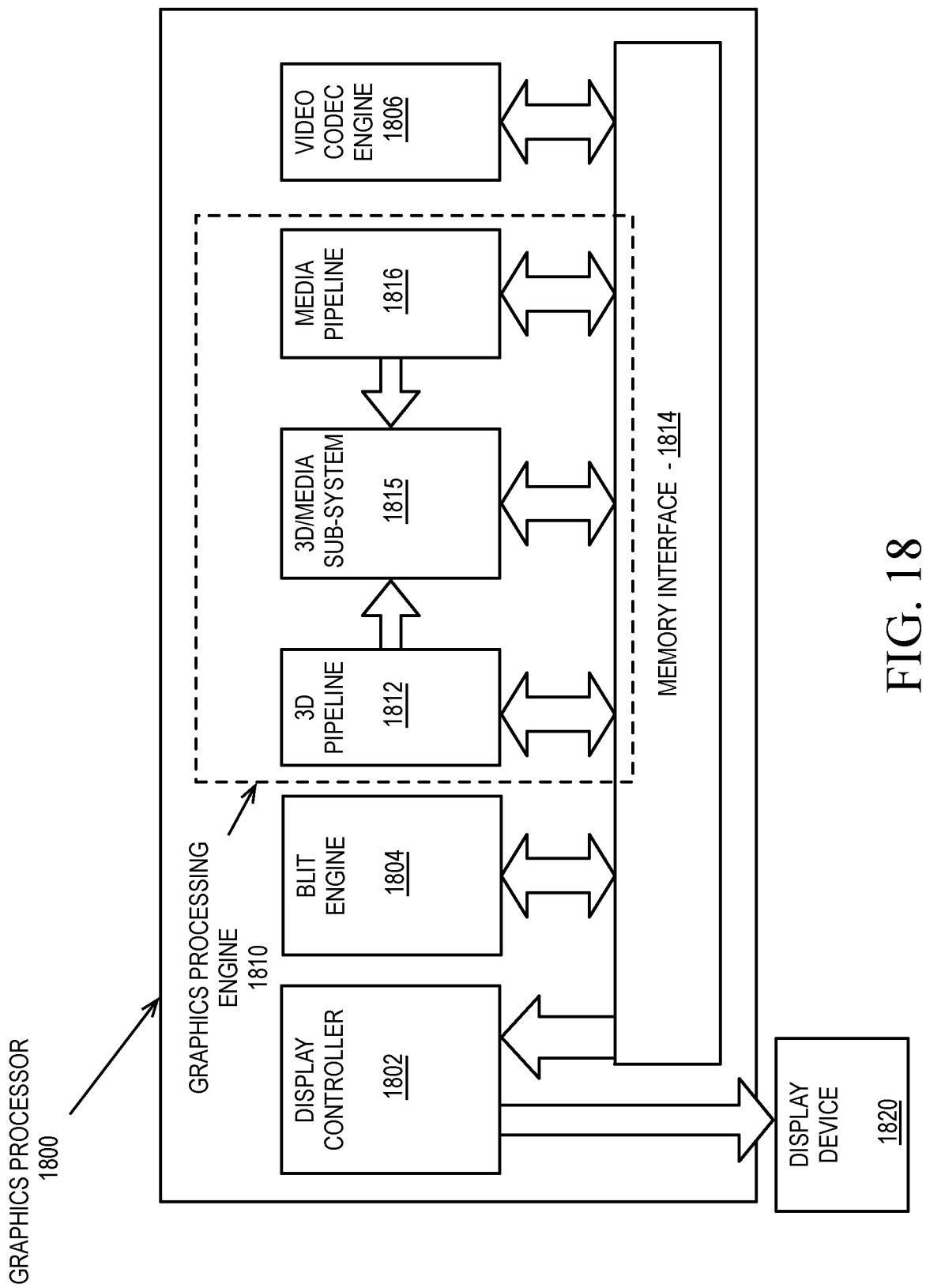
FIG. 18 is a block diagram of a graphics processor, according to an embodiment.

FIG. 18 is a block diagram of a graphics processor 1800, which may be a discrete graphics processing unit, or may be a graphics processor integrated with a plurality of processing cores. In some embodiments, the graphics processor communicates via a memory mapped I/O interface to registers on the graphics processor and with commands placed into the processor memory. In some embodiments, graphics processor 1800 includes a memory interface 1814 to access memory. Memory interface 1814 can be an interface to local memory, one or more internal caches, one or more shared external caches, and/or to system memory.

In some embodiments, graphics processor 1800 also includes a display controller 1802 to drive display output data to a display device 1820. Display controller 1802 includes hardware for one or more overlay planes for the display and composition of multiple layers of video or user interface elements. In some embodiments, graphics processor 1800 includes a video codec engine 1806 to encode, decode, or transcode media to, from, or between one or more media encoding formats, including, but not limited to Moving Picture Experts Group (MPEG) formats such as MPEG-2, Advanced Video Coding (AVC) formats such as H.264/MPEG-4 AVC, as well as the Society of Motion Picture & Television Engineers (SMPTE) 421M/VC-1, and Joint Photographic Experts Group (JPEG) formats such as JPEG, and Motion JPEG (MJPEG) formats.

In some embodiments, graphics processor 1800 includes a block image transfer (BLIT) engine 1804 to perform two-dimensional (2D) rasterizer operations including, for example, bit-boundary block transfers. However, in one embodiment, 2D graphics operations are performed using one or more components of graphics processing engine (GPE) 1810. In some embodiments, GPE 1810 is a compute engine for performing graphics operations, including three-dimensional (3D) graphics operations and media operations.

In some embodiments, GPE 1810 includes a 3D pipeline 1812 for performing 3D operations, such as rendering three-dimensional images and scenes using processing functions that act upon 3D primitive shapes (e.g., rectangle, triangle, etc.). The 3D pipeline 1812 includes programmable and fixed function elements that perform various tasks within the element and/or spawn execution threads to a 3D/Media subsystem 1815. While 3D pipeline 1812 can be used to perform media operations, an embodiment of GPE 1810 also includes a media pipeline 1816 that is specifically used to perform media operations, such as video post-processing and image enhancement.

In some embodiments, media pipeline 1816 includes fixed function or programmable logic units to perform one or more specialized media operations, such as video decode acceleration, video de-interlacing, and video encode acceleration in place of, or on behalf of video codec engine 1806. In some embodiments, media pipeline 1816 additionally includes a thread spawning unit to spawn threads for execution on 3D/Media subsystem 1815. The spawned threads perform computations for the media operations on one or more graphics execution units included in 3D/Media subsystem 1815.

In some embodiments, 3D/Media subsystem 1815 includes logic for executing threads spawned by 3D pipeline 1812 and media pipeline 1816. In one embodiment, the pipelines send thread execution requests to 3D/Media subsystem 1815, which includes thread dispatch logic for arbitrating and dispatching the various requests to available thread execution resources. The execution resources include an array of graphics execution units to process the 3D and media threads. In some embodiments, 3D/Media subsystem 1815 includes one or more internal caches for thread instructions and data. In some embodiments, the subsystem also includes shared memory, including registers and addressable memory, to share data between threads and to store output data.

Graphics Processing Engine

Figure 19:
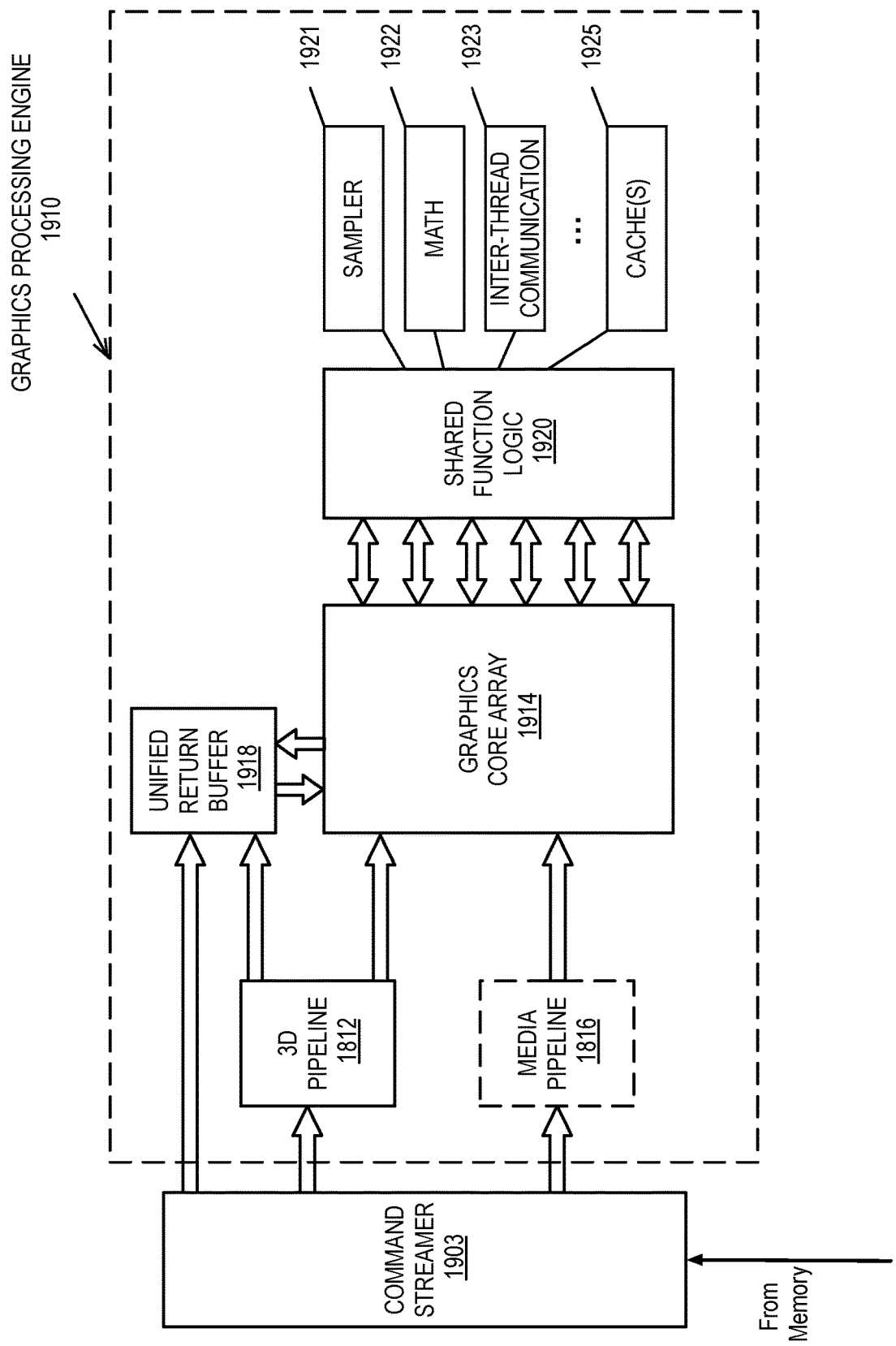
FIG. 19 is a block diagram of a graphics processing engine of a graphics processor in accordance with some embodiments.

FIG. 19 is a block diagram of a graphics processing engine 1910 of a graphics processor in accordance with some embodiments. In one embodiment, the graphics processing engine (GPE) 1910 is a version of the GPE 1810 shown in FIG. 18. Elements of FIG. 19 having the same reference numbers (or names) as the elements of any other figure herein can operate or function in any manner similar to that described elsewhere herein, but are not limited to such. For example, the 3D pipeline 1812 and media pipeline 1816 of FIG. 18 are illustrated. The media pipeline 1816 is optional in some embodiments of the GPE 1910 and may not be explicitly included within the GPE 1910. For example and in at least one embodiment, a separate media and/or image processor is coupled to the GPE 1910.

In some embodiments, GPE 1910 couples with or includes a command streamer 1903, which provides a command stream to the 3D pipeline 1812 and/or media pipelines 1816. In some embodiments, command streamer 1903 is coupled with memory, which can be system memory, or one or more of internal cache memory and shared cache memory. In some embodiments, command streamer 1903 receives commands from the memory and sends the commands to 3D pipeline 1812 and/or media pipeline 1816. The commands are directives fetched from a ring buffer, which stores commands for the 3D pipeline 1812 and media pipeline 1816. In one embodiment, the ring buffer can additionally include batch command buffers storing batches of multiple commands. The commands for the 3D pipeline 1812 can also include references to data stored in memory, such as but not limited to vertex and geometry data for the 3D pipeline 1812 and/or image data and memory objects for the media pipeline 1816. The 3D pipeline 1812 and media pipeline 1816 process the commands and data by performing operations via logic within the respective pipelines or by dispatching one or more execution threads to a graphics core array 1914.

In various embodiments the 3D pipeline 1812 can execute one or more shader programs, such as vertex shaders, geometry shaders, pixel shaders, fragment shaders, compute shaders, or other shader programs, by processing the instructions and dispatching execution threads to the graphics core array 1914. The graphics core array 1914 provides a unified block of execution resources. Multi-purpose execution logic (e.g., execution units) within the graphics core array 1914 includes support for various 3D API shader languages and can execute multiple simultaneous execution threads associated with multiple shaders.

In some embodiments the graphics core array 1914 also includes execution logic to perform media functions, such as video and/or image processing. In one embodiment, the execution units additionally include general-purpose logic that is programmable to perform parallel general purpose computational operations, in addition to graphics processing operations. The general-purpose logic can perform processing operations in parallel or in conjunction with general purpose logic within the processor core(s) 1607 of FIG. 16 or processor core 1702A-1702N as in FIG. 17.

Output data generated by threads executing on the graphics core array 1914 can output data to memory in a unified return buffer (URB) 1918. The URB 1918 can store data for multiple threads. In some embodiments the URB 1918 may be used to send data between different threads executing on the graphics core array 1914. In some embodiments the URB 1918 may additionally be used for synchronization between threads on the graphics core array and fixed function logic within the shared function logic 1920.

In some embodiments, graphics core array 1914 is scalable, such that the array includes a variable number of graphics cores, each having a variable number of execution units based on the target power and performance level of GPE 1910. In one embodiment the execution resources are dynamically scalable, such that execution resources may be enabled or disabled as needed.

The graphics core array 1914 couples with shared function logic 1920 that includes multiple resources that are shared between the graphics cores in the graphics core array. The shared functions within the shared function logic 1920 are hardware logic units that provide specialized supplemental functionality to the graphics core array 1914. In various embodiments, shared function logic 1920 includes but is not limited to sampler 1921, math 1922, and inter-thread communication (ITC) 1923 logic. Additionally, some embodiments implement one or more cache(s) 1925 within the shared function logic 1920. A shared function is implemented where the demand for a given specialized function is insufficient for inclusion within the graphics core array 1914. Instead a single instantiation of that specialized function is implemented as a stand-alone entity in the shared function logic 1920 and shared among the execution resources within the graphics core array 1914. The precise set of functions that are shared between the graphics core array 1914 and included within the graphics core array 1914 varies between embodiments.

Figure 20:
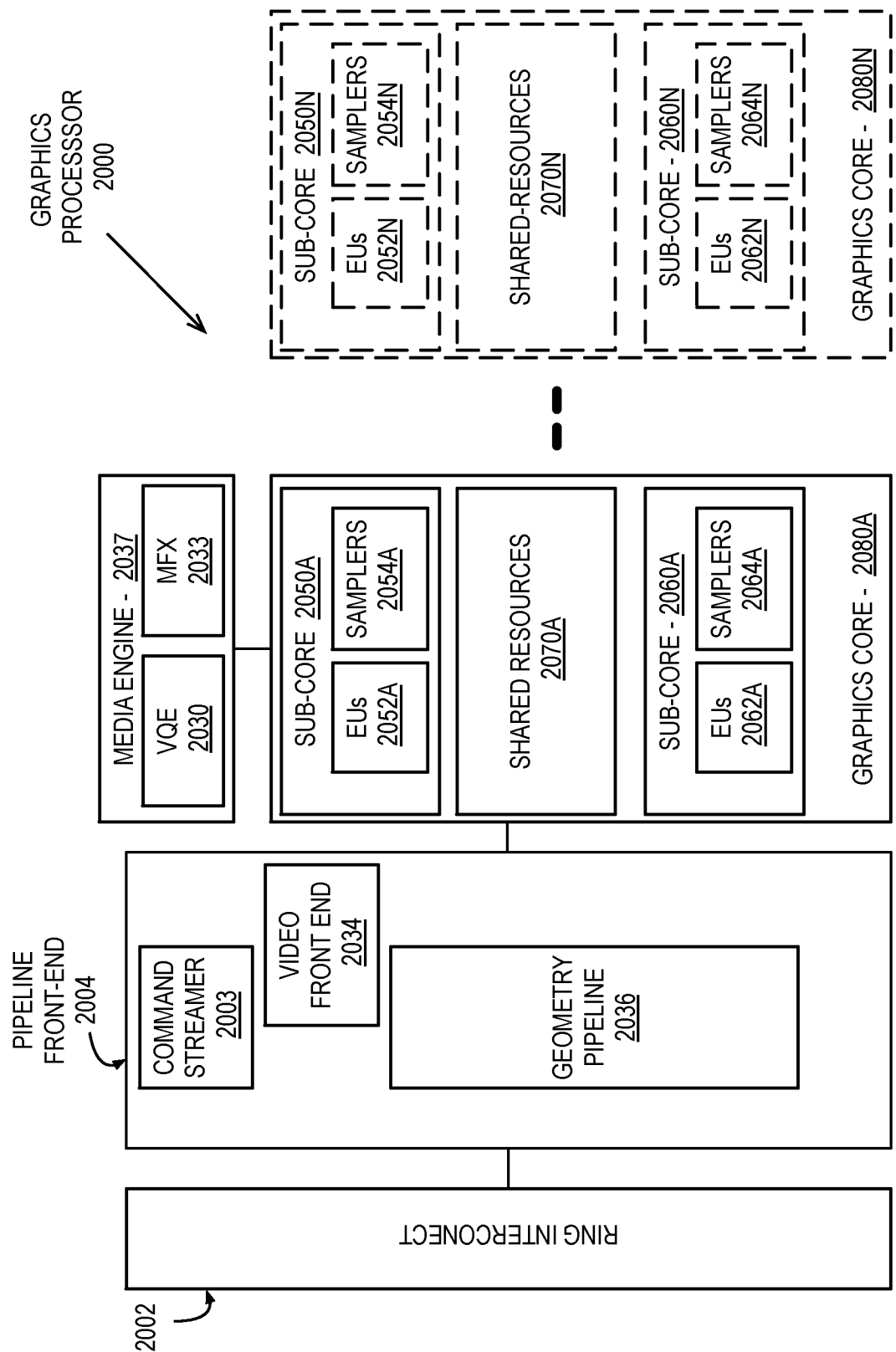
FIG. 20 is a block diagram of a graphics processor provided by an additional embodiment.

FIG. 20 is a block diagram of another embodiment of a graphics processor 2000. Elements of FIG. 20 having the same reference numbers (or names) as the elements of any other figure herein can operate or function in any manner similar to that described elsewhere herein, but are not limited to such.

In some embodiments, graphics processor 2000 includes a ring interconnect 2002, a pipeline front-end 2004, a media engine 2037, and graphics cores 2080A-2080N. In some embodiments, ring interconnect 2002 couples the graphics processor to other processing units, including other graphics processors or one or more general-purpose processor cores. In some embodiments, the graphics processor is one of many processors integrated within a multi-core processing system.

In some embodiments, graphics processor 2000 receives batches of commands via ring interconnect 2002. The incoming commands are interpreted by a command streamer 2003 in the pipeline front-end 2004. In some embodiments, graphics processor 2000 includes scalable execution logic to perform 3D geometry processing and media processing via the graphics core(s) 2080A-2080N. For 3D geometry processing commands, command streamer 2003 supplies commands to geometry pipeline 2036. For at least some media processing commands, command streamer 2003 supplies the commands to a video front end 2034, which couples with a media engine 2037. In some embodiments, media engine 2037 includes a Video Quality Engine (VQE) 2030 for video and image post-processing and a multi-format encode/decode (MFX) 2033 engine to provide hardware-accelerated media data encode and decode. In some embodiments, geometry pipeline 2036 and media engine 2037 each generate execution threads for the thread execution resources provided by at least one graphics core 2080A.

In some embodiments, graphics processor 2000 includes scalable thread execution resources featuring modular cores 2080A-2080N (sometimes referred to as core slices), each having multiple sub-cores 2050A-550N, 2060A-2060N (sometimes referred to as core sub-slices). In some embodiments, graphics processor 2000 can have any number of graphics cores 2080A through 2080N. In some embodiments, graphics processor 2000 includes a graphics core 2080A having at least a first sub-core 2050A and a second sub-core 2060A. In other embodiments, the graphics processor is a low power processor with a single sub-core (e.g., 2050A). In some embodiments, graphics processor 2000 includes multiple graphics cores 2080A-2080N, each including a set of first sub-cores 2050A-2050N and a set of second sub-cores 2060A-2060N. Each sub-core in the set of first sub-cores 2050A-2050N includes at least a first set of execution units 2052A-2052N and media/texture samplers 2054A-2054N. Each sub-core in the set of second sub-cores 2060A-2060N includes at least a second set of execution units 2062A-2062N and samplers 2064A-2064N. In some embodiments, each sub-core 2050A-2050N, 2060A-2060N shares a set of shared resources 2070A-2070N. In some embodiments, the shared resources include shared cache memory and pixel operation logic. Other shared resources may also be included in the various embodiments of the graphics processor.

Execution Units

Figure 21:
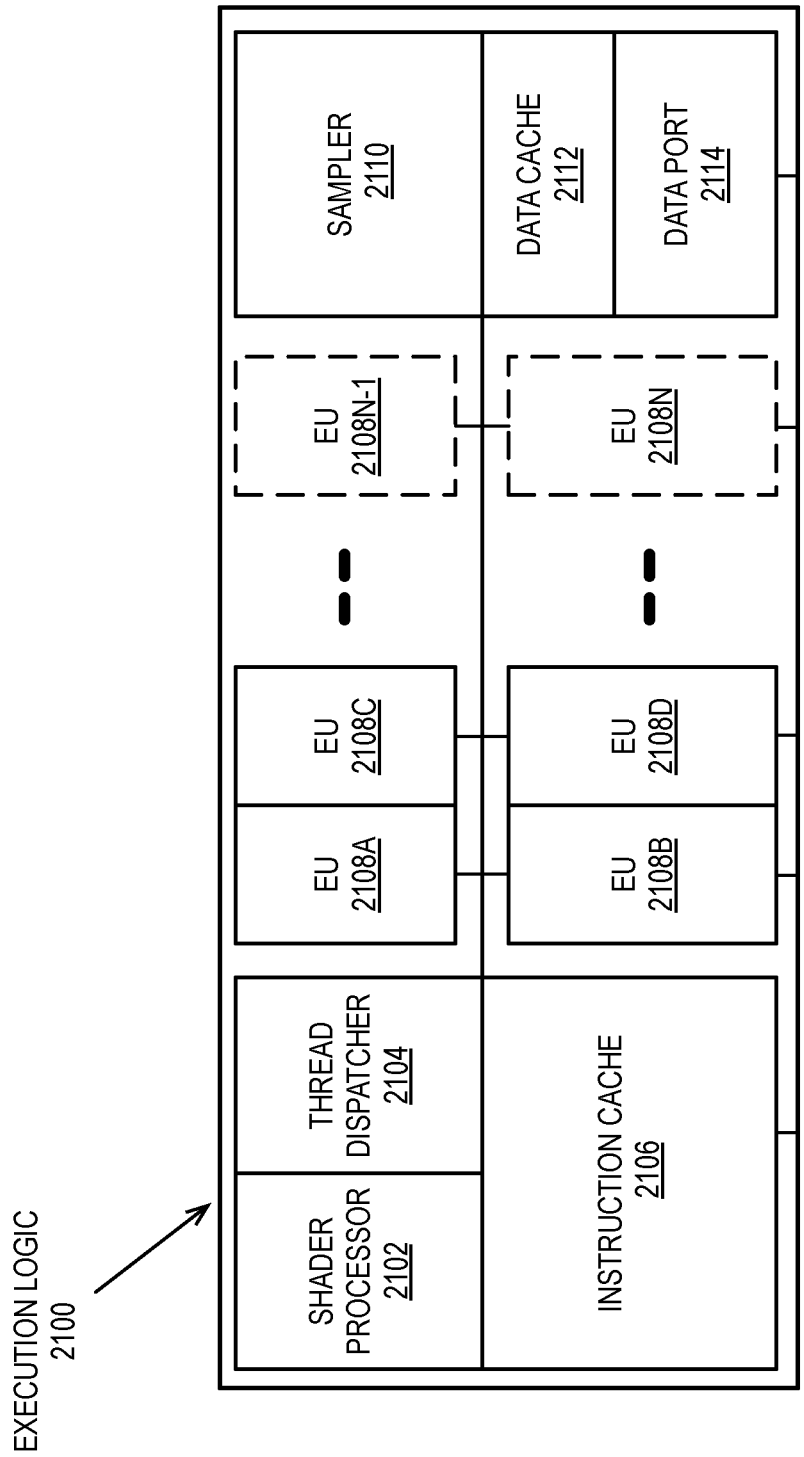
FIG. 21 illustrates thread execution logic including an array of processing elements employed in some embodiments.

FIG. 21 illustrates thread execution logic 2100 including an array of processing elements employed in some embodiments of a GPE. Elements of FIG. 21 having the same reference numbers (or names) as the elements of any other figure herein can operate or function in any manner similar to that described elsewhere herein, but are not limited to such.

In some embodiments, thread execution logic 2100 includes a shader processor 2102, a thread dispatcher 2104, instruction cache 2106, a scalable execution unit array including a plurality of execution units 2108A-2108N, a sampler 2110, a data cache 2112, and a data port 2114. In one embodiment the scalable execution unit array can dynamically scale by enabling or disabling one or more execution units (e.g., any of execution unit 2108A, 2108B, 2108C, 2108D, through 2108N-1 and 2108N) based on the computational requirements of a workload. In one embodiment the included components are interconnected via an interconnect fabric that links to each of the components. In some embodiments, thread execution logic 2100 includes one or more connections to memory, such as system memory or cache memory, through one or more of instruction cache 2106, data port 2114, sampler 2110, and execution units 2108A-2108N. In some embodiments, each execution unit (e.g. 2108A) is a stand-alone programmable general purpose computational unit that is capable of executing multiple simultaneous hardware threads while processing multiple data elements in parallel for each thread. In various embodiments, the array of execution units 2108A-2108N is scalable to include any number individual execution units.

In some embodiments, the execution units 2108A-2108N are primarily used to execute shader programs. A shader processor 2102 can process the various shader programs and dispatch execution threads associated with the shader programs via a thread dispatcher 2104. In one embodiment the thread dispatcher includes logic to arbitrate thread initiation requests from the graphics and media pipelines and instantiate the requested threads on one or more execution unit in the execution units 2108A-2108N. For example, the geometry pipeline (e.g., 2036 of FIG. 20) can dispatch vertex, tessellation, or geometry shaders to the thread execution logic 2100 (FIG. 21) for processing. In some embodiments, thread dispatcher 2104 can also process runtime thread spawning requests from the executing shader programs.

In some embodiments, the execution units 2108A-2108N support an instruction set that includes native support for many standard 3D graphics shader instructions, such that shader programs from graphics libraries (e.g., Direct 3D and OpenGL) are executed with a minimal translation. The execution units support vertex and geometry processing (e.g., vertex programs, geometry programs, vertex shaders), pixel processing (e.g., pixel shaders, fragment shaders) and general-purpose processing (e.g., compute and media shaders). Each of the execution units 2108A-2108N is capable of multi-issue single instruction multiple data (SIMD) execution and multi-threaded operation enables an efficient execution environment in the face of higher latency memory accesses. Each hardware thread within each execution unit has a dedicated high-bandwidth register file and associated independent thread-state. Execution is multi-issue per clock to pipelines capable of integer, single and double precision floating point operations, SIMD branch capability, logical operations, transcendental operations, and other miscellaneous operations. While waiting for data from memory or one of the shared functions, dependency logic within the execution units 2108A-2108N causes a waiting thread to sleep until the requested data has been returned. While the waiting thread is sleeping, hardware resources may be devoted to processing other threads. For example, during a delay associated with a vertex shader operation, an execution unit can perform operations for a pixel shader, fragment shader, or another type of shader program, including a different vertex shader.

Each execution unit in execution units 2108A-2108N operates on arrays of data elements. The number of data elements is the "execution size," or the number of channels for the instruction. An execution channel is a logical unit of execution for data element access, masking, and flow control within instructions. The number of channels may be independent of the number of physical Arithmetic Logic Units (ALUs) or Floating Point Units (FPUs) for a particular graphics processor. In some embodiments, execution units 2108A-2108N support integer and floating-point data types.

The execution unit instruction set includes SIMD instructions. The various data elements can be stored as a packed data type in a register and the execution unit will process the various elements based on the data size of the elements. For example, when operating on a 256-bit wide vector, the 256 bits of the vector are stored in a register and the execution unit operates on the vector as four separate 64-bit packed data elements (Quad-Word (QW) size data elements), eight separate 32-bit packed data elements (Double Word (DW) size data elements), sixteen separate 16-bit packed data elements (Word (W) size data elements), or thirty-two separate 8-bit data elements (byte (B) size data elements). However, different vector widths and register sizes are possible.

One or more internal instruction caches (e.g., 2106) are included in the thread execution logic 2100 to cache thread instructions for the execution units. In some embodiments, one or more data caches (e.g., 2112) are included to cache thread data during thread execution. In some embodiments, a sampler 2110 is included to provide texture sampling for 3D operations and media sampling for media operations. In some embodiments, sampler 2110 includes specialized texture or media sampling functionality to process texture or media data during the sampling process before providing the sampled data to an execution unit.

During execution, the graphics and media pipelines send thread initiation requests to thread execution logic 2100 via thread spawning and dispatch logic. Once a group of geometric objects has been processed and rasterized into pixel data, pixel processor logic (e.g., pixel shader logic, fragment shader logic, etc.) within the shader processor 2102 is invoked to further compute output information and cause results to be written to output surfaces (e.g., color buffers, depth buffers, stencil buffers, etc.). In some embodiments, a pixel shader or fragment shader calculates the values of the various vertex attributes that are to be interpolated across the rasterized object. In some embodiments, pixel processor logic within the shader processor 2102 then executes an application programming interface (API)-supplied pixel or fragment shader program. To execute the shader program, the shader processor 2102 dispatches threads to an execution unit (e.g., 2108A) via thread dispatcher 2104. In some embodiments, shader processor 2102 uses texture sampling logic in the sampler 2110 to access texture data in texture maps stored in memory. Arithmetic operations on the texture data and the input geometry data compute pixel color data for each geometric fragment, or discards one or more pixels from further processing.

In some embodiments, the data port 2114 provides a memory access mechanism for the thread execution logic 2100 output processed data to memory for processing on a graphics processor output pipeline. In some embodiments, the data port 2114 includes or couples to one or more cache memories (e.g., data cache 2112) to cache data for memory access via the data port.

FIG. 22 is a block diagram illustrating graphics processor instruction formats 2200 according to some embodiments. In one or more embodiment, the graphics processor execution units support an instruction set having instructions in multiple formats. The solid lined boxes illustrate the components that are generally included in an execution unit instruction, while the dashed lines include components that are optional or that are only included in a sub-set of the instructions. In some embodiments, instruction format 2200 described and illustrated are macro-instructions, in that they are instructions supplied to the execution unit, as opposed to micro-operations resulting from instruction decode once the instruction is processed.

In some embodiments, the graphics processor execution units natively support instructions in a 128-bit instruction format 2210. A 64-bit compacted instruction format 2230 is available for some instructions based on the selected instruction, instruction options, and number of operands. The native 128-bit instruction format 2210 provides access to all instruction options, while some options and operations are restricted in the 64-bit format 2230. The native instructions available in the 64-bit format 2230 vary by embodiment. In some embodiments, the instruction is compacted in part using a set of index values in an index field 2213. The execution unit hardware references a set of compaction tables based on the index values and uses the compaction table outputs to reconstruct a native instruction in the 128-bit instruction format 2210.

For each format, instruction opcode 2212 defines the operation that the execution unit is to perform. The execution units execute each instruction in parallel across the multiple data elements of each operand. For example, in response to an add instruction the execution unit performs a simultaneous add operation across each color channel representing a texture element or picture element. By default, the execution unit performs each instruction across all data channels of the operands. In some embodiments, instruction control field 2214 enables control over certain execution options, such as channels selection (e.g., predication) and data channel order (e.g., swizzle). For instructions in the 128-bit instruction format 2210 an exec-size field 2216 limits the number of data channels that will be executed in parallel. In some embodiments, exec-size field 2216 is not available for use in the 64-bit compact instruction format 2230.

Some execution unit instructions have up to three operands including two source operands, src0 2220, src1 2222, and one destination 2218. In some embodiments, the execution units support dual destination instructions, where one of the destinations is implied. Data manipulation instructions can have a third source operand (e.g., SRC2 2224), where the instruction opcode 2212 determines the number of source operands. An instruction's last source operand can be an immediate (e.g., hard-coded) value passed with the instruction.

In some embodiments, the 128-bit instruction format 2210 includes an access/address mode field 2226 specifying, for example, whether direct register addressing mode or indirect register addressing mode is used. When direct register addressing mode is used, the register address of one or more operands is directly provided by bits in the instruction.

In some embodiments, the 128-bit instruction format 2210 includes an access/address mode field 2226, which specifies an address mode and/or an access mode for the instruction. In one embodiment the access mode is used to define a data access alignment for the instruction. Some embodiments support access modes including a 16-byte aligned access mode and a 1-byte aligned access mode, where the byte alignment of the access mode determines the access alignment of the instruction operands. For example, when in a first mode, the instruction may use byte-aligned addressing for source and destination operands and when in a second mode, the instruction may use 16-byte-aligned addressing for all source and destination operands.

In one embodiment, the address mode portion of the access/address mode field 2226 determines whether the instruction is to use direct or indirect addressing. When direct register addressing mode is used bits in the instruction directly provide the register address of one or more operands. When indirect register addressing mode is used, the register address of one or more operands may be computed based on an address register value and an address immediate field in the instruction.

In some embodiments instructions are grouped based on opcode 2212 bit-fields to simplify Opcode decode 2240. For an 8-bit opcode, bits 4, 5, and 6 allow the execution unit to determine the type of opcode. The precise opcode grouping shown is merely an example. In some embodiments, a move and logic opcode group 2242 includes data movement and logic instructions (e.g., move (mov), compare (cmp)). In some embodiments, move and logic opcode group 2242 shares the five most significant bits (MSB), where move (mov) instructions are in the form of 0000xxxxb and logic instructions are in the form of 0001xxxxb. A flow control instruction group 2244 (e.g., call, jump (jmp)) includes instructions in the form of 0010xxxxb (e.g., 0x20). A miscellaneous instruction group 2246 includes a mix of instructions, including synchronization instructions (e.g., wait, send) in the form of 0011xxxxb (e.g., 0x30). A parallel math instruction group 2248 includes component-wise arithmetic instructions (e.g., add, multiply (mul)) in the form of 0100xxxxb (e.g., 0x40). The parallel math group 2248 performs the arithmetic operations in parallel across data channels. The vector math group 2250 includes arithmetic instructions (e.g., dp4) in the form of 0101xxxxb (e.g., 0x50). The vector math group performs arithmetic such as dot product calculations on vector operands.

Graphics Pipeline

Figure 23:
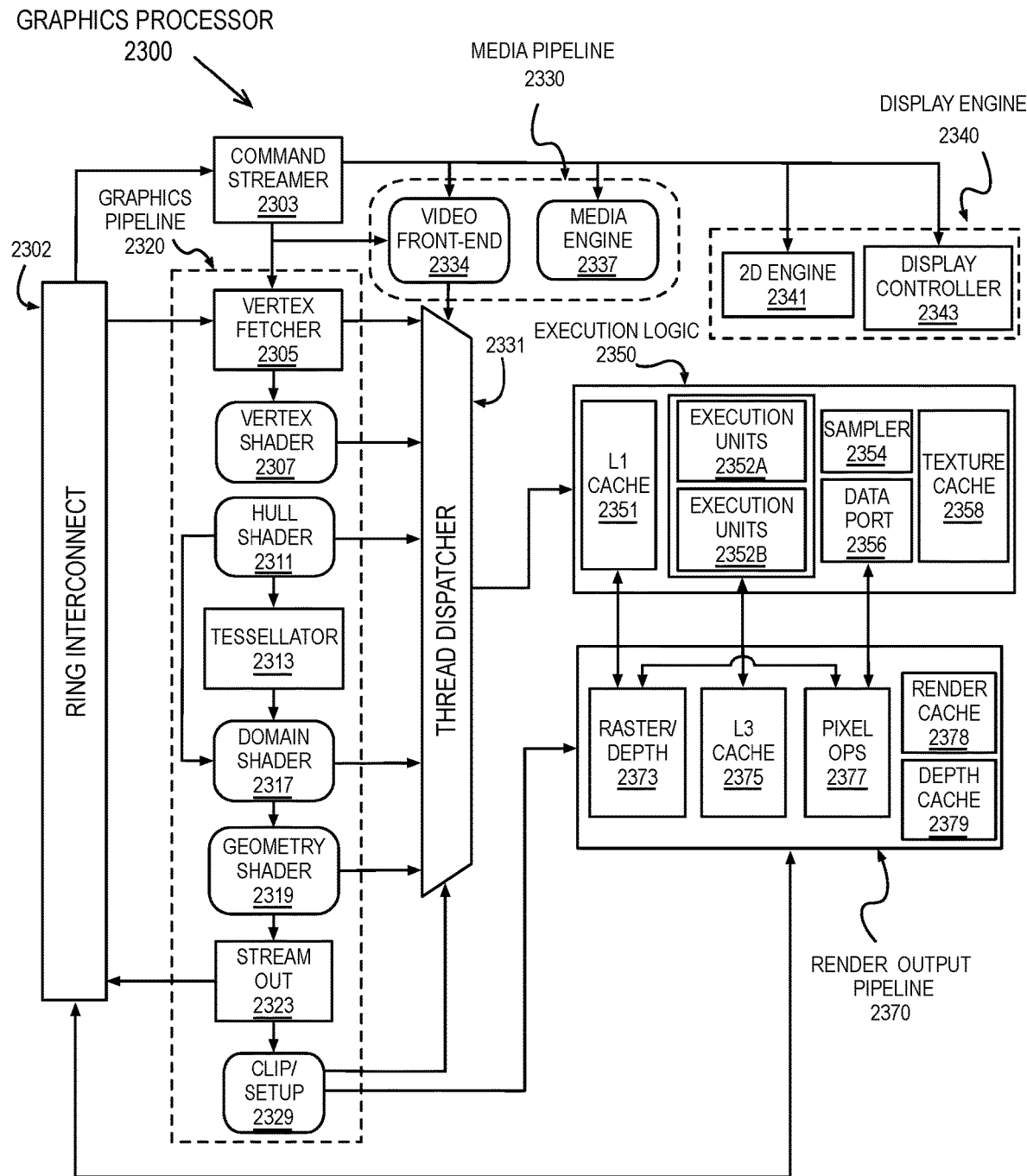
FIG. 23 is a block diagram of a graphics processor according to another embodiment.

FIG. 23 is a block diagram of another embodiment of a graphics processor 2300. Elements of FIG. 23 having the same reference numbers (or names) as the elements of any other figure herein can operate or function in any manner similar to that described elsewhere herein, but are not limited to such.

In some embodiments, graphics processor 2300 includes a graphics pipeline 2320, a media pipeline 2330, a display engine 2340, thread execution logic 2350, and a render output pipeline 2370. In some embodiments, graphics processor 2300 is a graphics processor within a multi-core processing system that includes one or more general purpose processing cores. The graphics processor is controlled by register writes to one or more control registers (not shown) or via commands issued to graphics processor 2300 via a ring interconnect 2302. In some embodiments, ring interconnect 2302 couples graphics processor 2300 to other processing components, such as other graphics processors or general-purpose processors. Commands from ring interconnect 2302 are interpreted by a command streamer 2303, which supplies instructions to individual components of graphics pipeline 2320 or media pipeline 2330.

In some embodiments, command streamer 2303 directs the operation of a vertex fetcher 2305 that reads vertex data from memory and executes vertex-processing commands provided by command streamer 2303. In some embodiments, vertex fetcher 2305 provides vertex data to a vertex shader 2307, which performs coordinate space transformation and lighting operations to each vertex. In some embodiments, vertex fetcher 2305 and vertex shader 2307 execute vertex-processing instructions by dispatching execution threads to execution units 2352A-2352B via a thread dispatcher 2331.

In some embodiments, execution units 2352A-2352B are an array of vector processors having an instruction set for performing graphics and media operations. In some embodiments, execution units 2352A-2352B have an attached L1 cache 2351 that is specific for each array or shared between the arrays. The cache can be configured as a data cache, an instruction cache, or a single cache that is partitioned to contain data and instructions in different partitions.

In some embodiments, graphics pipeline 2320 includes tessellation components to perform hardware-accelerated tessellation of 3D objects. In some embodiments, a programmable hull shader 811 configures the tessellation operations. A programmable domain shader 817 provides back-end evaluation of tessellation output. A tessellator 2313 operates at the direction of hull shader 2311 and contains special purpose logic to generate a set of detailed geometric objects based on a coarse geometric model that is provided as input to graphics pipeline 2320. In some embodiments, if tessellation is not used, tessellation components (e.g., hull shader 2311, tessellator 2313, and domain shader 2317) can be bypassed.

In some embodiments, complete geometric objects can be processed by a geometry shader 2319 via one or more threads dispatched to execution units 2352A-2352B, or can proceed directly to the clipper 2329. In some embodiments, the geometry shader operates on entire geometric objects, rather than vertices or patches of vertices as in previous stages of the graphics pipeline. If the tessellation is disabled the geometry shader 2319 receives input from the vertex shader 2307. In some embodiments, geometry shader 2319 is programmable by a geometry shader program to perform geometry tessellation if the tessellation units are disabled.

Before rasterization, a clipper 2329 processes vertex data. The clipper 2329 may be a fixed function clipper or a programmable clipper having clipping and geometry shader functions. In some embodiments, a rasterizer and depth test component 2373 in the render output pipeline 2370 dispatches pixel shaders to convert the geometric objects into their per pixel representations. In some embodiments, pixel shader logic is included in thread execution logic 2350. In some embodiments, an application can bypass the rasterizer and depth test component 2373 and access un-rasterized vertex data via a stream out unit 2323.

The graphics processor 2300 has an interconnect bus, interconnect fabric, or some other interconnect mechanism that allows data and message passing amongst the major components of the processor. In some embodiments, execution units 2352A-2352B and associated cache(s) 2351, texture and media sampler 2354, and texture/sampler cache 2358 interconnect via a data port 2356 to perform memory access and communicate with render output pipeline components of the processor. In some embodiments, sampler 2354, caches 2351, 2358 and execution units 2352A-2352B each have separate memory access paths.

In some embodiments, render output pipeline 2370 contains a rasterizer and depth test component 2373 that converts vertex-based objects into an associated pixel-based representation. In some embodiments, the rasterizer logic includes a windower/masker unit to perform fixed function triangle and line rasterization. An associated render cache 2378 and depth cache 2379 are also available in some embodiments. A pixel operations component 2377 performs pixel-based operations on the data, though in some instances, pixel operations associated with 2D operations (e.g. bit block image transfers with blending) are performed by the 2D engine 2341, or substituted at display time by the display controller 2343 using overlay display planes. In some embodiments, a shared L3 cache 2375 is available to all graphics components, allowing the sharing of data without the use of main system memory.

In some embodiments, graphics processor media pipeline 2330 includes a media engine 2337 and a video front-end 2334. In some embodiments, video front-end 2334 receives pipeline commands from the command streamer 2303. In some embodiments, media pipeline 2330 includes a separate command streamer. In some embodiments, video front-end 2334 processes media commands before sending the command to the media engine 2337. In some embodiments, media engine 2337 includes thread spawning functionality to spawn threads for dispatch to thread execution logic 2350 via thread dispatcher 2331.

In some embodiments, graphics processor 2300 includes a display engine 2340. In some embodiments, display engine 2340 is external to processor 2300 and couples with the graphics processor via the ring interconnect 2302, or some other interconnect bus or fabric. In some embodiments, display engine 2340 includes a 2D engine 2341 and a display controller 2343. In some embodiments, display engine 2340 contains special purpose logic capable of operating independently of the 3D pipeline. In some embodiments, display controller 2343 couples with a display device (not shown), which may be a system integrated display device, as in a laptop computer, or an external display device attached via a display device connector.

In some embodiments, graphics pipeline 2320 and media pipeline 2330 are configurable to perform operations based on multiple graphics and media programming interfaces and are not specific to any one application programming interface (API). In some embodiments, driver software for the graphics processor translates API calls that are specific to a particular graphics or media library into commands that can be processed by the graphics processor. In some embodiments, support is provided for the Open Graphics Library (OpenGL), Open Computing Language (OpenCL), and/or Vulkan graphics and compute API, all from the Khronos Group. In some embodiments, support may also be provided for the Direct3D library from the Microsoft Corporation. In some embodiments, a combination of these libraries may be supported. Support may also be provided for the Open Source Computer Vision Library (OpenCV). A future API with a compatible 3D pipeline would also be supported if a mapping can be made from the pipeline of the future API to the pipeline of the graphics processor.

Graphics Pipeline Programming

FIG. 24A is a block diagram illustrating a graphics processor command format 2400 according to some embodiments. FIG. 24B is a block diagram illustrating a graphics processor command sequence 2410 according to an embodiment. The solid lined boxes in FIG. 24A illustrate the components that are generally included in a graphics command while the dashed lines include components that are optional or that are only included in a sub-set of the graphics commands. The exemplary graphics processor command format 2400 of FIG. 24A includes data fields to identify a target client 2402 of the command, a command operation code (opcode) 2404, and the relevant data field 2406 for the command. A sub-opcode 2405 and a command size 2408 are also included in some commands.

In some embodiments, client 2402 specifies the client unit of the graphics device that processes the command data. In some embodiments, a graphics processor command parser examines the client field of each command to condition the further processing of the command and route the command data to the appropriate client unit. In some embodiments, the graphics processor client units include a memory interface unit, a render unit, a 2D unit, a 3D unit, and a media unit. Each client unit has a corresponding processing pipeline that processes the commands. Once the command is received by the client unit, the client unit reads the opcode 2404 and, if present, sub-opcode 2405 to determine the operation to perform. The client unit performs the command using information in data field 2406. For some commands an explicit command size 2408 is expected to specify the size of the command. In some embodiments, the command parser automatically determines the size of at least some of the commands based on the command opcode. In some embodiments commands are aligned via multiples of a double word.

The flow diagram in FIG. 24B shows an exemplary graphics processor command sequence 2410. In some embodiments, software or firmware of a data processing system that features an embodiment of a graphics processor uses a version of the command sequence shown to set up, execute, and terminate a set of graphics operations. A sample command sequence is shown and described for purposes of example only as embodiments are not limited to these specific commands or to this command sequence. Moreover, the commands may be issued as batch of commands in a command sequence, such that the graphics processor will process the sequence of commands in at least partially concurrence.

In some embodiments, the graphics processor command sequence 2410 may begin with a pipeline flush command 2412 to cause any active graphics pipeline to complete the currently pending commands for the pipeline. In some embodiments, the 3D pipeline 2422 and the media pipeline 2424 do not operate concurrently. The pipeline flush is performed to cause the active graphics pipeline to complete any pending commands. In response to a pipeline flush, the command parser for the graphics processor will pause command processing until the active drawing engines complete pending operations and the relevant read caches are invalidated. Optionally, any data in the render cache that is marked 'dirty' can be flushed to memory. In some embodiments, pipeline flush command 2412 can be used for pipeline synchronization or before placing the graphics processor into a low power state.

In some embodiments, a pipeline select command 2413 is used when a command sequence requires the graphics processor to explicitly switch between pipelines. In some embodiments, a pipeline select command 2413 is required only once within an execution context before issuing pipeline commands unless the context is to issue commands for both pipelines. In some embodiments, a pipeline flush command 2412 is required immediately before a pipeline switch via the pipeline select command 2413.

In some embodiments, a pipeline control command 2414 configures a graphics pipeline for operation and is used to program the 3D pipeline 2422 and the media pipeline 2424. In some embodiments, pipeline control command 2414 configures the pipeline state for the active pipeline. In one embodiment, the pipeline control command 2414 is used for pipeline synchronization and to clear data from one or more cache memories within the active pipeline before processing a batch of commands.

In some embodiments, return buffer state commands 2416 are used to configure a set of return buffers for the respective pipelines to write data. Some pipeline operations require the allocation, selection, or configuration of one or more return buffers into which the operations write intermediate data during processing. In some embodiments, the graphics processor also uses one or more return buffers to store output data and to perform cross thread communication. In some embodiments, the return buffer state 2416 includes selecting the size and number of return buffers to use for a set of pipeline operations.

The remaining commands in the command sequence differ based on the active pipeline for operations. Based on a pipeline determination 2420, the command sequence is tailored to the 3D pipeline 2422 beginning with the 3D pipeline state 2430 or the media pipeline 2424 beginning at the media pipeline state 2440.

The commands to configure the 3D pipeline state 2430 include 3D state setting commands for vertex buffer state, vertex element state, constant color state, depth buffer state, and other state variables that are to be configured before 3D primitive commands are processed. The values of these commands are determined at least in part based on the particular 3D API in use. In some embodiments, 3D pipeline state 2430 commands are also able to selectively disable or bypass certain pipeline elements if those elements will not be used.

In some embodiments, 3D primitive 2432 command is used to submit 3D primitives to be processed by the 3D pipeline. Commands and associated parameters that are passed to the graphics processor via the 3D primitive 2432 command are forwarded to the vertex fetch function in the graphics pipeline. The vertex fetch function uses the 3D primitive 2432 command data to generate vertex data structures. The vertex data structures are stored in one or more return buffers. In some embodiments, 3D primitive 2432 command is used to perform vertex operations on 3D primitives via vertex shaders. To process vertex shaders, 3D pipeline 2422 dispatches shader execution threads to graphics processor execution units.

In some embodiments, 3D pipeline 2422 is triggered via an execute 2434 command or event. In some embodiments, a register write triggers command execution. In some embodiments execution is triggered via a 'go' or 'kick' command in the command sequence. In one embodiment, command execution is triggered using a pipeline synchronization command to flush the command sequence through the graphics pipeline. The 3D pipeline will perform geometry processing for the 3D primitives. Once operations are complete, the resulting geometric objects are rasterized and the pixel engine colors the resulting pixels. Additional commands to control pixel shading and pixel back end operations may also be included for those operations.

In some embodiments, the graphics processor command sequence 2410 follows the media pipeline 2424 path when performing media operations. In general, the specific use and manner of programming for the media pipeline 2424 depends on the media or compute operations to be performed. Specific media decode operations may be offloaded to the media pipeline during media decode. In some embodiments, the media pipeline can also be bypassed and media decode can be performed in whole or in part using resources provided by one or more general purpose processing cores. In one embodiment, the media pipeline also includes elements for general-purpose graphics processor unit (GPGPU) operations, where the graphics processor is used to perform SIMD vector operations using computational shader programs that are not explicitly related to the rendering of graphics primitives.

In some embodiments, media pipeline 2424 is configured in a similar manner as the 3D pipeline 2422. A set of commands to configure the media pipeline state 2440 are dispatched or placed into a command queue before the media object commands 2442. In some embodiments, the commands for the media pipeline state 2440 include data to configure the media pipeline elements that will be used to process the media objects. This includes data to configure the video decode and video encode logic within the media pipeline, such as encode or decode format. In some embodiments, commands for the media pipeline state 2440 enable support the use of one or more pointers to "indirect" state elements that contain a batch of state settings.

In some embodiments, media object commands 2442 supply pointers to media objects for processing by the media pipeline. The media objects include memory buffers containing video data to be processed. In some embodiments, all media pipeline states must be valid before issuing a media object command 2442. Once the pipeline state is configured and media object commands 2442 are queued, the media pipeline 2424 is triggered via an execute command 2444 or an equivalent execute event (e.g., register write). Output from media pipeline 2424 may then be post processed by operations provided by the 3D pipeline 2422 or the media pipeline 2424. In some embodiments, GPGPU operations are configured and executed in a similar manner as media operations.

Graphics Software Architecture

Figure 25:
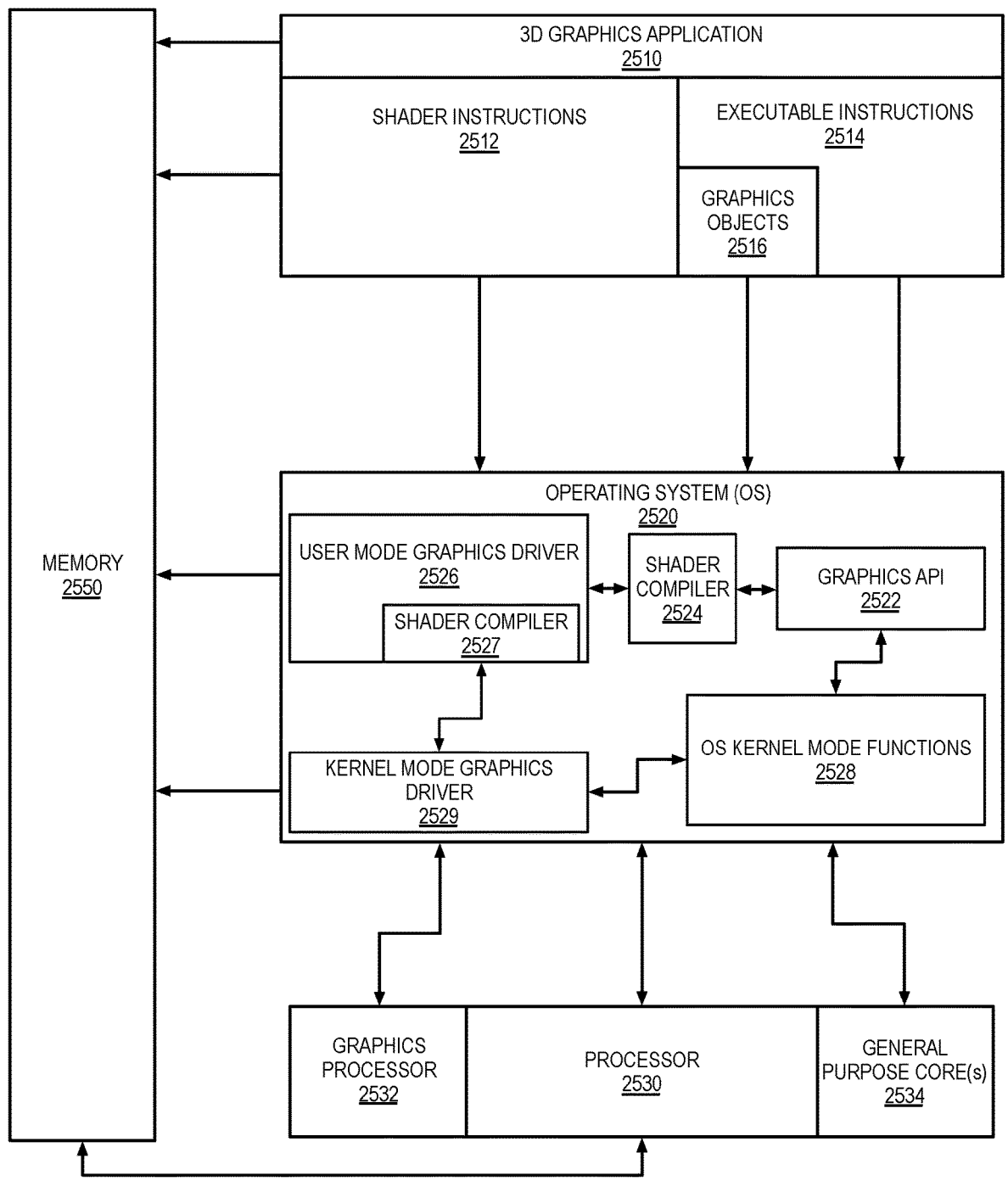
FIG. 25 illustrates exemplary graphics software architecture for a data processing system according to some embodiments.

FIG. 25 illustrates exemplary graphics software architecture for a data processing system 2500 according to some embodiments. In some embodiments, software architecture includes a 3D graphics application 2510, an operating system 2520, and at least one processor 2530. In some embodiments, processor 2530 includes a graphics processor 2532 and one or more general-purpose processor core(s) 2534. The graphics application 2510 and operating system 2520 each execute in the system memory 2550 of the data processing system.

In some embodiments, 3D graphics application 2510 contains one or more shader programs including shader instructions 2512. The shader language instructions may be in a high-level shader language, such as the High Level Shader Language (HLSL) or the OpenGL Shader Language (GLSL). The application also includes executable instructions 2514 in a machine language suitable for execution by the general-purpose processor core(s) 2534. The application also includes graphics objects 2516 defined by vertex data.

In some embodiments, operating system 2520 is a Microsoft® Windows® operating system from the Microsoft Corporation, a proprietary UNIX-like operating system, or an open source UNIX-like operating system using a variant of the Linux kernel. The operating system 2520 can support a graphics API 2522 such as the Direct3D API, the OpenGL API, or the Vulkan API. When the Direct3D API is in use, the operating system 2520 uses a front-end shader compiler 2524 to compile any shader instructions 2512 in HLSL into a lower-level shader language. The compilation may be a just-in-time (JIT) compilation or the application can perform shader pre-compilation. In some embodiments, high-level shaders are compiled into low-level shaders during the compilation of the 3D graphics application 2510. In some embodiments, the shader instructions 2512 are provided in an intermediate form, such as a version of the Standard Portable Intermediate Representation (SPIR) used by the Vulkan API.

In some embodiments, user mode graphics driver 2526 contains a back-end shader compiler 2527 to convert the shader instructions 2512 into a hardware specific representation. When the OpenGL API is in use, shader instructions 2512 in the GLSL high-level language are passed to a user mode graphics driver 2526 for compilation. In some embodiments, user mode graphics driver 2526 uses operating system kernel mode functions 2528 to communicate with a kernel mode graphics driver 2529. In some embodiments, kernel mode graphics driver 2529 communicates with graphics processor 2532 to dispatch commands and instructions.

IP Core Implementations

One or more aspects of at least one embodiment may be implemented by representative code stored on a machine-readable medium which represents and/or defines logic within an integrated circuit such as a processor. For example, the machine-readable medium may include instructions which represent various logic within the processor. When read by a machine, the instructions may cause the machine to fabricate the logic to perform the techniques described herein. Such representations, known as "IP cores," are reusable units of logic for an integrated circuit that may be stored on a tangible, machine-readable medium as a hardware model that describes the structure of the integrated circuit. The hardware model may be supplied to various customers or manufacturing facilities, which load the hardware model on fabrication machines that manufacture the integrated circuit. The integrated circuit may be fabricated such that the circuit performs operations described in association with any of the embodiments described herein.

Figure 26:
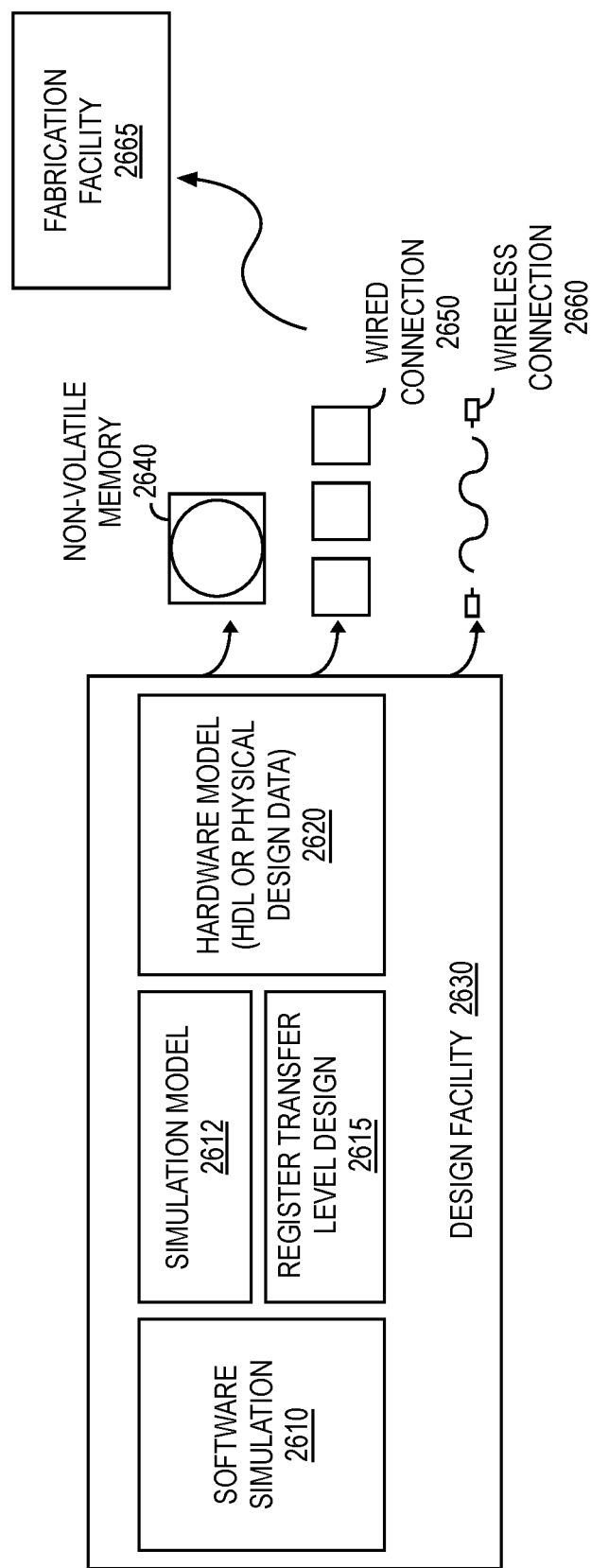
FIG. 26 is a block diagram illustrating an IP core development system, according to an embodiment.

FIG. 26 is a block diagram illustrating an IP core development system 2600 that may be used to manufacture an integrated circuit to perform operations according to an embodiment. The IP core development system 2600 may be used to generate modular, re-usable designs that can be incorporated into a larger design or used to construct an entire integrated circuit (e.g., an SOC integrated circuit). A design facility 2630 can generate a software simulation 2610 of an IP core design in a high level programming language (e.g., C/C++). The software simulation 2610 can be used to design, test, and verify the behavior of the IP core using a simulation model 2612. The simulation model 2612 may include functional, behavioral, and/or timing simulations. A register transfer level (RTL) design 2615 can then be created or synthesized from the simulation model 2612. The RTL design 2615 is an abstraction of the behavior of the integrated circuit that models the flow of digital signals between hardware registers, including the associated logic performed using the modeled digital signals. In addition to an RTL design 2615, lower-level designs at the logic level or transistor level may also be created, designed, or synthesized. Thus, the particular details of the initial design and simulation may vary.

The RTL design 2615 or equivalent may be further synthesized by the design facility into a hardware model 2620, which may be in a hardware description language (HDL), or some other representation of physical design data. The HDL may be further simulated or tested to verify the IP core design. The IP core design can be stored for delivery to a 3rd party fabrication facility 2665 using non-volatile memory 2640 (e.g., hard disk, flash memory, or any non-volatile storage medium). Alternatively, the IP core design may be transmitted (e.g., via the Internet) over a wired connection 2650 or wireless connection 2660. The fabrication facility 2665 may then fabricate an integrated circuit that is based at least in part on the IP core design. The fabricated integrated circuit can be configured to perform operations in accordance with at least one embodiment described herein.

Exemplary System on a Chip Integrated Circuit

Figure 27:
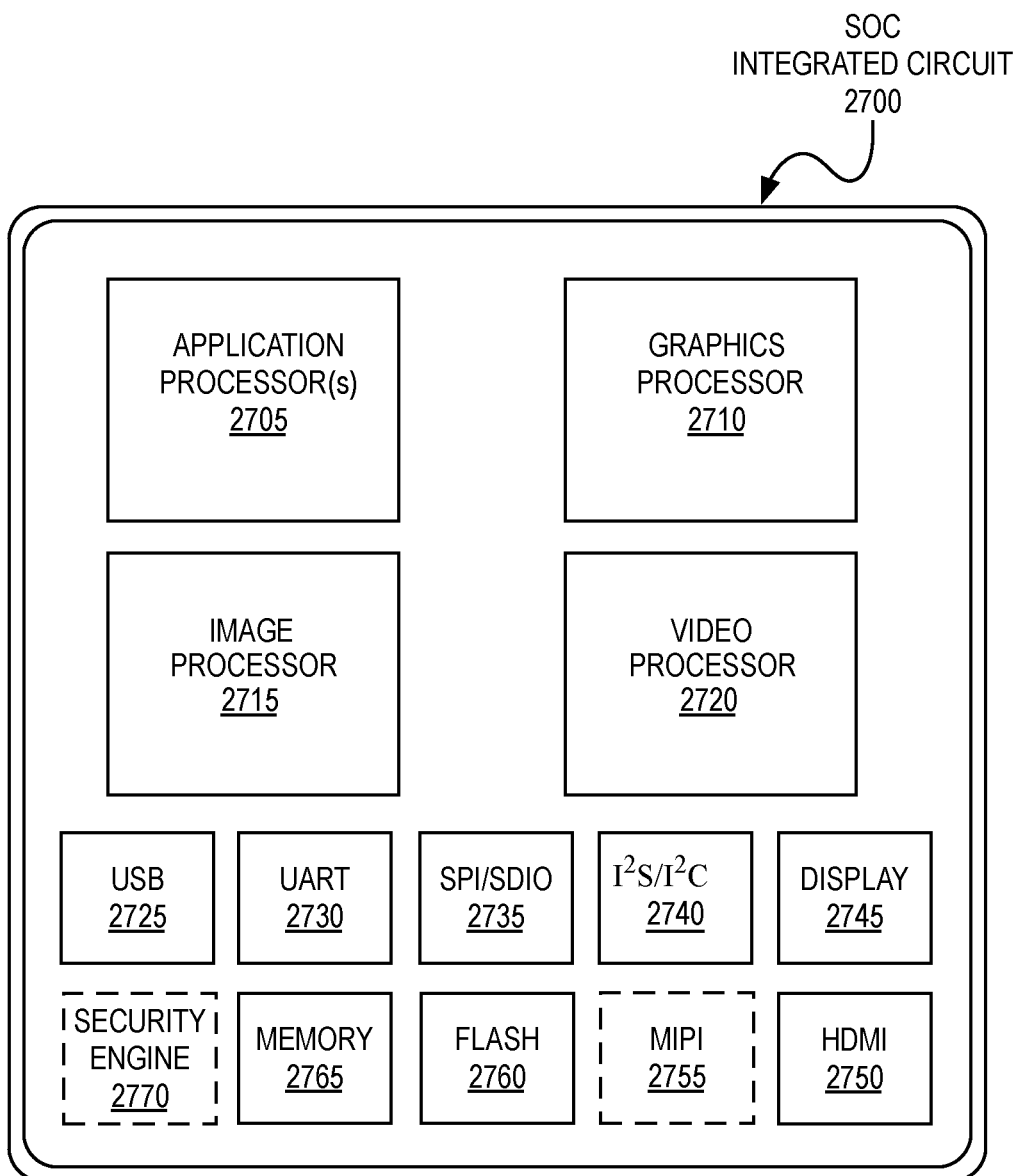
FIG. 27 is a block diagram illustrating an exemplary system on a chip integrated circuit, according to an embodiment.
Figure 28:
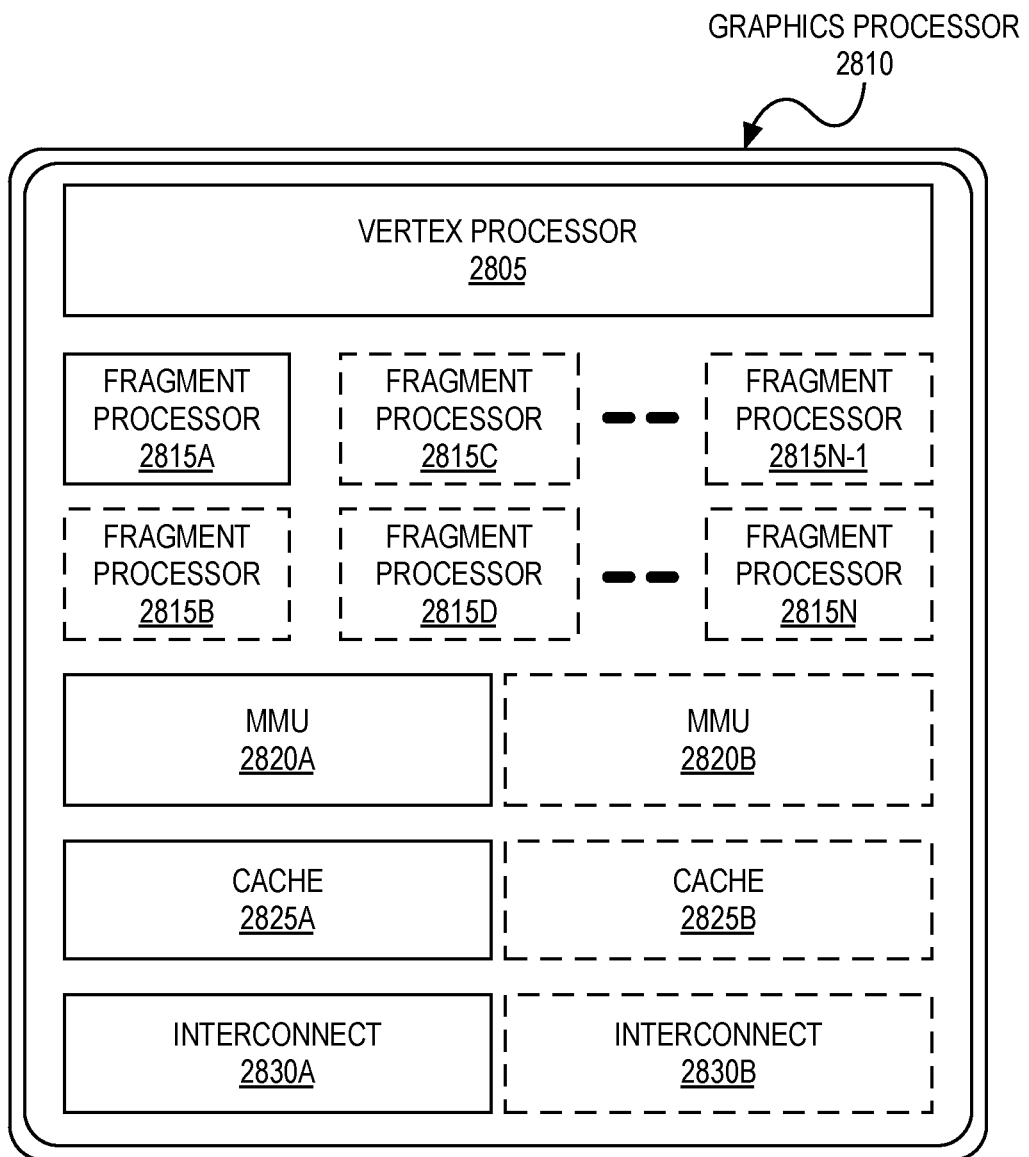
FIG. 28 is a block diagram illustrating an additional exemplary graphics processor.
Figure 29:
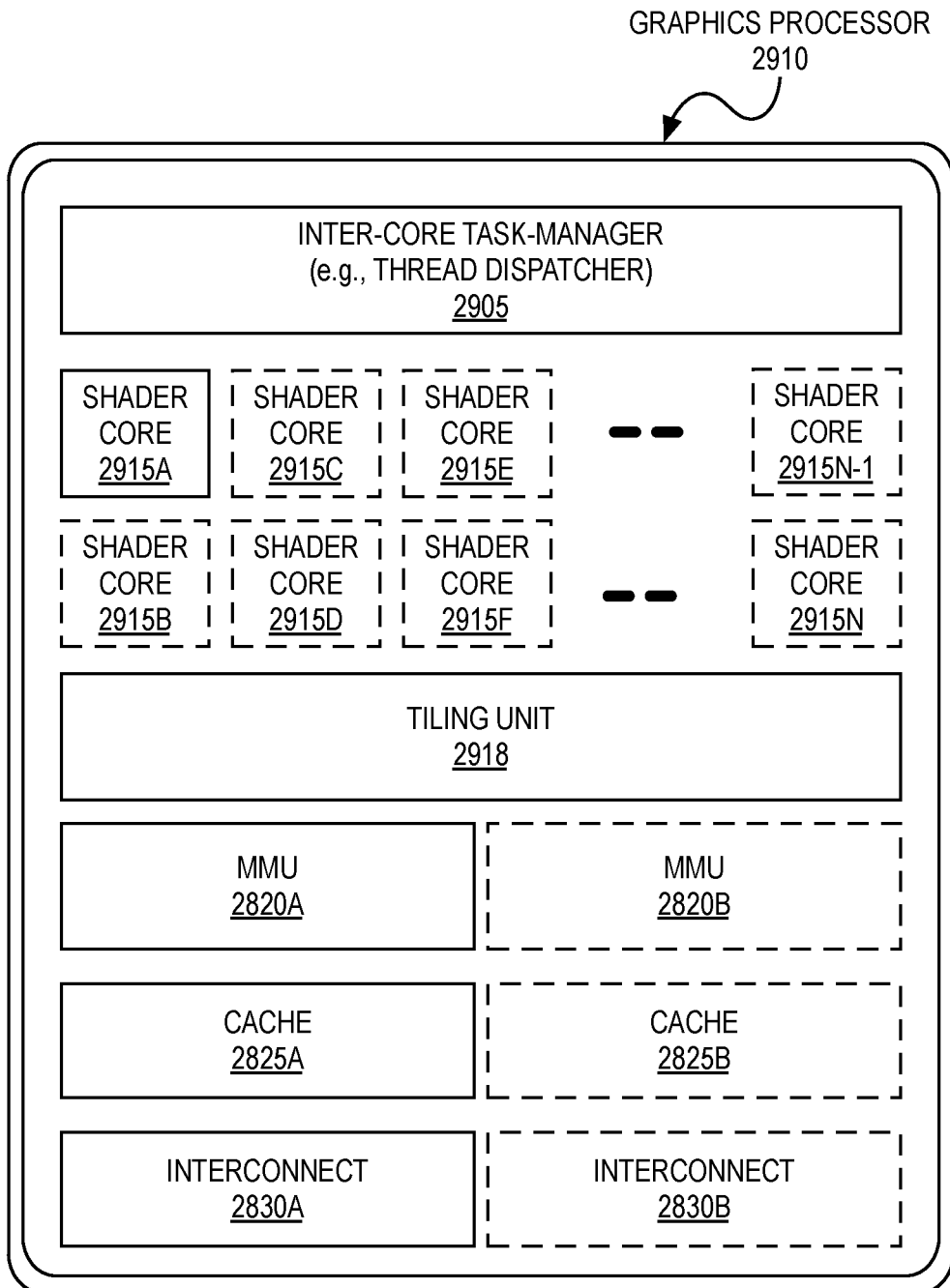
FIG. 29 is a block diagram illustrating an additional exemplary graphics processor of a system on a chip integrated circuit, according to an embodiment.

FIGS. 27-29 illustrated exemplary integrated circuits and associated graphics processors that may be fabricated using one or more IP cores, according to various embodiments described herein. In addition to what is illustrated, other logic and circuits may be included, including additional graphics processors/cores, peripheral interface controllers, or general purpose processor cores.

FIG. 27 is a block diagram illustrating an exemplary system on a chip integrated circuit 2700 that may be fabricated using one or more IP cores, according to an embodiment. Exemplary integrated circuit 2700 includes one or more application processor(s) 2705 (e.g., CPUs), at least one graphics processor 2710, and may additionally include an image processor 2715 and/or a video processor 2720, any of which may be a modular IP core from the same or multiple different design facilities. Integrated circuit 2700 includes peripheral or bus logic including a USB controller 2725, UART controller 2730, an SPI/SDIO controller 2735, and an $I^2S/I^2C$ controller 2740. Additionally, the integrated circuit can include a display device 2745 coupled to one or more of a high-definition multimedia interface (HDMI) controller 2750 and a mobile industry processor interface (MIPI) display interface 2755. Storage may be provided by a flash memory subsystem 2760 including flash memory and a flash memory controller. Memory interface may be provided via a memory controller 2765 for access to SDRAM or SRAM memory devices. Some integrated circuits additionally include an embedded security engine 2770.

FIG. 28 is a block diagram illustrating an exemplary graphics processor 2810 of a system on a chip integrated circuit that may be fabricated using one or more IP cores, according to an embodiment. Graphics processor 2810 can be a variant of the graphics processor 2710 of FIG. 27. Graphics processor 2810 includes a vertex processor 2805 and one or more fragment processor(s) 2815A-2815N (e.g., 2815A, 2815B, 2815C, 2815D, through 2815N-1, and 2815N). Graphics processor 2810 can execute different shader programs via separate logic, such that the vertex processor 2805 is optimized to execute operations for vertex shader programs, while the one or more fragment processor(s) 2815A-2815N execute fragment (e.g., pixel) shading operations for fragment or pixel shader programs. The vertex processor 2805 performs the vertex processing stage of the 3D graphics pipeline and generates primitives and vertex data. The fragment processor(s) 2815A-2815N use the primitive and vertex data generated by the vertex processor 2805 to produce a framebuffer that is displayed on a display device. In one embodiment, the fragment processor(s) 2815A-2815N are optimized to execute fragment shader programs as provided for in the OpenGL API, which may be used to perform similar operations as a pixel shader program as provided for in the Direct 3D API.

Graphics processor 2810 additionally includes one or more memory management units (MMUs) 2820A-2820B, cache(s) 2825A-2825B, and circuit interconnect(s) 2830A-2830B. The one or more MMU(s) 2820A-2820B provide for virtual to physical address mapping for the graphics processor 2810, including for the vertex processor 2805 and/or fragment processor(s) 2815A-2815N, which may reference vertex or image/texture data stored in memory, in addition to vertex or image/texture data stored in the one or more cache(s) 2825A-2825B. In one embodiment the one or more MMU(s) 2820A-2820B may be synchronized with other MMUs within the system, including one or more MMUs associated with the one or more application processor(s) 2705, image processor 2715, and/or video processor 2720 of FIG. 27, such that each processor 2705-2720 can participate in a shared or unified virtual memory system. The one or more circuit interconnect(s) 2830A-2830B enable graphics processor 2810 to interface with other IP cores within the SoC, either via an internal bus of the SoC or via a direct connection, according to embodiments.

FIG. 29 is a block diagram illustrating an additional exemplary graphics processor 2910 of a system on a chip integrated circuit that may be fabricated using one or more IP cores, according to an embodiment. Graphics processor 2910 can be a variant of the graphics processor 2710 of FIG. 27. Graphics processor 2910 includes the one or more MMU(s) 2820A-2820B, cache(s) 2825A-2825B, and circuit interconnect(s) 2830A-2830B of the integrated circuit 2800 of FIG. 28.

Graphics processor 2910 includes one or more shader core(s) 2915A-2915N (e.g., 2915A, 2915B, 2915C, 2915D, 2915E, 2915F, through 2915N-1, and 2915N), which provides for a unified shader core architecture in which a single core or type or core can execute all types of programmable shader code, including shader program code to implement vertex shaders, fragment shaders, and/or compute shaders. The exact number of shader cores present can vary among embodiments and implementations. Additionally, graphics processor 2910 includes an inter-core task manager 2905, which acts as a thread dispatcher to dispatch execution threads to one or more shader core(s) 2915A-2915N and a tiling unit 2918 to accelerate tiling operations for tile-based rendering, in which rendering operations for a scene are subdivided in image space, for example to exploit local spatial coherence within a scene or to optimize use of internal caches.

The following pertains to further examples.

Example 1 may optionally include an apparatus comprising a plurality of execution units; and logic, at least partially including hardware logic, to traverse a solution space; score a plurality of solutions to a scheduling deep learning network execution; and select a preferred solution from the plurality of solutions to implement the deep learning network.

Example 2 may optionally include the subject matter of example 1, wherein the preferred solution defines a tile size for the deep learning network.

Example 3 may optionally include the subject matter of any one of examples 1-2, wherein the preferred solution defines a traversal order for the deep learning network.

Example 4 may optionally include the subject matter of any one of examples 1-3, wherein the preferred solution defines a buffering level for the deep learning network.

Example 5 may optionally include the subject matter of any one of examples 1-4, wherein the preferred solution defines a data type for the deep learning network.

Example 6 may optionally include the subject matter of any one of examples 1-5, wherein a scheduler component determines a traversal strategy for the deep learning neural network execution and forwards the traversal strategy to the plurality of execution units.

Example 7 may optionally include the subject matter of any one of examples 1-6, wherein the plurality of execution units are on a single integrated circuit.

Example 8 may optionally include an electronic device comprising a processor having a plurality of execution units; and logic, at least partially including hardware logic, to traverse a solution space; core a plurality of solutions to a scheduling deep learning network execution; and select a preferred solution from the plurality of solutions to implement the deep learning network.

Example 9 may optionally include the subject matter of example 8, wherein the preferred solution defines a tile size for the deep learning network.

Example 10 may optionally include the subject matter of any one of examples 8-9, wherein the preferred solution defines a traversal order for the deep learning network.

Example 11 may optionally include the subject matter of any one of examples 8-11, wherein the preferred solution defines a buffering level for the deep learning network.

Example 12 may optionally include the subject matter of any one of examples 8-11, wherein the preferred solution defines a data type for the deep learning network.

Example 13 may optionally include the subject matter of any one of examples 8-12, wherein a scheduler component determines a traversal strategy for the deep learning neural network execution and forwards the traversal strategy to the plurality of execution units.

Example 14 may optionally include the subject matter of any one of examples 8-13, wherein the plurality of execution units are on a single integrated circuit.

In various embodiments, the operations discussed herein may be implemented as hardware (e.g., logic circuitry), software, firmware, or combinations thereof, which may be provided as a computer program product, e.g., including a tangible (e.g., non-transitory) machine-readable or computer-readable medium having stored thereon instructions (or software procedures) used to program a computer to perform a process discussed herein. The machine-readable medium may include an information storage device.

Additionally, such computer-readable media may be downloaded as a computer program product, wherein the program may be transferred from a remote computer (e.g., a server) to a requesting computer (e.g., a client) by way of data signals provided in a carrier wave or other propagation medium via a communication link (e.g., a bus, a modem, or a network connection).

Reference in the specification to "one embodiment" or "an embodiment" means that a particular feature, structure, and/or characteristic described in connection with the embodiment may be included in at least an implementation. The appearances of the phrase "in one embodiment" in various places in the specification may or may not be all referring to the same embodiment.

Also, in the description and claims, the terms "coupled" and "connected," along with their derivatives, may be used. In some embodiments, "connected" may be used to indicate that two or more elements are in direct physical or electrical contact with each other. "Coupled" may mean that two or more elements are in direct physical or electrical contact. However, "coupled" may also mean that two or more elements may not be in direct contact with each other, but may still cooperate or interact with each other.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. An apparatus comprising:
a cluster of distinct interconnected graphics processors, each graphics processor including a plurality of processing resources; and
processing circuitry to schedule operations to the cluster of distinct interconnected graphics processors, the processing circuitry configured to:
determine a traversal strategy for a deep learning neural network, the traversal strategy to be implemented via dispatch components of the graphics processors in the cluster of distinct interconnected graphics processors; and
convey the traversal strategy to the dispatch components of the graphics processors, the graphics processors configured to:
receive the traversal strategy and data for the deep learning neural network;
traverse a solution space of the deep learning neural network to score a plurality of solutions to schedule deep learning network execution on the plurality of processing resources of a graphics processor of the cluster of distinct interconnected graphics processors;
select a solution from the plurality of solutions to implement the deep learning network based on scores associated with the plurality of solutions; and
implement a workload schedule to assign tasks to the plurality of processing resources, wherein the workload schedule specifies a batch of grouped operations, the operations of the batch of grouped operations determined via a machine learning model based on historical data associated with the cluster of distinct interconnected graphics processors.

2. The apparatus of claim 1, the solution to define a tile size for the deep learning network and a buffering level for the deep learning network.

3. The apparatus of claim 1, the solution to define a data type for the deep learning network.

4. The apparatus of claim 1, the solution to define a traversal order for the deep learning network.

5. The apparatus of claim 4, wherein a scheduler component is configured to determine the traversal strategy for the deep learning neural network execution and forward the traversal strategy to the plurality of processing resources.

6. The apparatus of claim 5, wherein the plurality of processing resources includes at least a first type of processing resource and a second type of processing resource that is different from the first type of processing resource.

7. The apparatus of claim 1, wherein the plurality of processing resources is on a single integrated circuit.

8. The apparatus of claim 1, wherein the traversal strategy is for a three-dimensional (3D) object divided into 3D tiles, each tile represented as a 3D cube in memory.

9. The apparatus of claim 1, the graphics processors of the cluster of distinct interconnected graphics processors interconnected via first plurality of point-to-point interconnects.

10. The apparatus of claim 9, at least a portion of the graphics processors of the cluster of distinct interconnected graphics processors additionally interconnected via a second plurality of interconnects to a host interface switch.

11. An electronic device, comprising:
a cluster of distinct interconnected graphics processors, each graphics processor including a plurality of processing resources; and
a processor, separate from the plurality of processing resources, to schedule operations to the cluster of distinct interconnected graphics processors, the processor configured to:
determine a traversal strategy for a deep learning neural network, the traversal strategy to be implemented via dispatch components of the graphics processors in the cluster of distinct interconnected graphics processors; and
convey the traversal strategy to the dispatch components of the graphics processors, the graphics processors configured to:
receive the traversal strategy and data for the deep learning neural network;
traverse a solution space of the deep learning neural network to score a plurality of solutions to schedule deep learning network execution on the plurality of processing resources of a graphics processor of the cluster of distinct interconnected graphics processors;
select a solution from the plurality of solutions to implement the deep learning network based on scores associated with the plurality of solutions; and
implement a workload schedule to assign tasks to the plurality of processing resources, wherein the workload schedule specifies a batch of grouped operations, the operations of the batch of grouped operations determined via a machine learning model based on historical data associated with the cluster of distinct interconnected graphics processors.

12. The electronic device of claim 11, the solution to define a tile size for the deep learning network and a buffering level for the deep learning network.

13. The electronic device of claim 11, the solution to define a data type for the deep learning network.

14. The electronic device of claim 11, the solution to define a traversal order for the deep learning network.

15. The electronic device of claim 14, wherein a scheduler component is configured to determine the traversal strategy for the deep learning neural network execution and forward the traversal strategy to the plurality of processing resources.

16. The electronic device of claim 15, wherein the plurality of processing resources includes at least a first type of processing resource and a second type of processing resource that is different from the first type of processing resource.

17. The electronic device of claim 11, wherein the plurality of processing resources is on a single integrated circuit.

18. The electronic device comprising of claim 11, wherein the traversal strategy is for a three-dimensional (3D) object divided into 3D tiles, each tile represented as a 3D cube in memory.

19. The electronic device of claim 11, the graphics processors of the cluster of distinct interconnected graphics processors interconnected via first plurality of point-to-point interconnects.

20. The electronic device of claim 19, at least a portion of the graphics processors of the cluster of distinct interconnected graphics processors additionally interconnected via a second plurality of interconnects to a host interface switch.

* * * * *